United States Patent
Beight et al.

(12) 
(10) Patent No.: US 6,417,200 B1
(45) Date of Patent: *Jul. 9, 2002

(54) ANTITHROMBOTIC AGENTS

(75) Inventors: Douglas Wade Beight; Trelia Joyce Craft; Jeffry Bernard Franciskovich; Theodore Goodson, Jr., all of Indianapolis, IN (US); Steven Edward Hall, Chapel Hill, NC (US); David Kent Herron, Indianapolis, IN (US); Valentine Joseph Klimkowski, Carmel, IN (US); John Joseph Masters, Fishers, IN (US); David Mendel, Indianapolis, IN (US); Guy Milot, Chapel Hill, NC (US); Jason Scott Sawyer, Indianapolis, IN (US); Robert Theodore Shuman, Sedona, AZ (US); Gerald Floyd Smith, Indianapolis, IN (US); Anne Louise Tebbe, Indianapolis, IN (US); Jennifer Marie Tinsley, Martinsville, IN (US); Leonard Crayton Weir, Raleigh, NC (US); James Howard Wikel, Greenwood, IN (US); Michael Robert Wiley, Indianapolis, IN (US); Ying Kwong Yee, Carmel, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/445,970

(22) PCT Filed: Jun. 26, 1998

(86) PCT No.: PCT/US98/13424

§ 371 (c)(1),
(2), (4) Date: May 9, 2000

(87) PCT Pub. No.: WO99/00127

PCT Pub. Date: Jan. 7, 1999

Related U.S. Application Data

(60) Provisional application No. 60/050,885, filed on Jun. 26, 1997.

(51) Int. Cl.[7] ................... A61K 31/445; A61K 31/167; C07D 211/32; C07C 233/64; A61P 7/02
(52) U.S. Cl. ................. 514/330; 514/379; 514/416; 514/616; 514/620; 546/234; 548/241; 548/482; 564/155; 564/157; 564/164; 564/244; 564/246

(58) Field of Search .................... 546/234; 548/241, 548/482; 564/155, 157, 164; 574/330, 379, 416, 616, 620

(56) References Cited

U.S. PATENT DOCUMENTS

| 4,514,415 A | 4/1985 | Fujii et al. |
| 5,518,735 A | 5/1996 | Stürzebecher |

FOREIGN PATENT DOCUMENTS

| WO | WO 97/11693 | 4/1997 |
| WO | WO 97/24135 | 7/1997 |
| WO | WO 97/47299 | 12/1997 |
| WO | WO 98/57951 | 12/1998 |
| WO | WO 99/00121 | 1/1999 |
| WO | WO 99/00126 | 1/1999 |
| WO | WO 99/00128 | 1/1999 |
| WO | WO 99/32477 | 7/1999 |
| WO | WO 99/42439 | 8/1999 |
| WO | WO 99/48878 | 9/1999 |
| WO | WO 00/39092 | 7/2000 |
| WO | WO 00/39111 | 7/2000 |
| WO | WO 00/39117 | 7/2000 |
| WO | WO 00/39118 | 7/2000 |

OTHER PUBLICATIONS

Wallis, R.B. Inhibitors of Coagulation Factor Xa: From Macromolecular Beginnings to Small Molecules. Current Opinion in Therapeutic Patents. 1993, vol. 3, No. 8, pp. 1173–1179.

Edmunds, Jeremy J. and Rapundalo, Stephen T., (Doherty, Annette M. Section Editor), *Annual Reports in Medicinal Chemistry*, (1996), 31, 51–60.

Myers, H. V., et al., *Molecular Diversity*, (1995), 1, 13–20.

Primary Examiner—Evelyn Mei Huang
(74) Attorney, Agent, or Firm—Thomas E. Jackson

(57) ABSTRACT

This application relates to a compound of formula (I), a pharmaceutically acceptable salt of the compound, or a prodrug thereof, as defined herein, pharmaceutical compositions thereof, and its use as an inhibitor of factor Xa, as well as a process for its preparation and intermediates therefor.

I

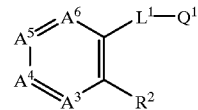

31 Claims, No Drawings

ANTITHROMBOTIC AGENTS

This application is the national phase of PCT/US 98/13424, which claims the benefit of U.S. Provisional Application No. 60/050,885, filed Jun. 26, 1997.

This invention relates to antithrombotic carboximidamide derivatives which demonstrate activity as inhibitors of factor Xa and, accordingly, which are useful anticoagulants in mammals. In particular it relates to carboximidamide derivatives having high anticoagulant activity, and antithrombotic activity. Thus, this invention relates to new inhibitors of factor Xa, pharmaceutical compositions containing the compounds as active ingredients, and the use of the compounds as anticoagulants for prophylaxis and treatment of thromboembolic disorders such as venous thrombosis, pulmonary embolism, arterial thrombosis, in particular myocardial ischemia, myocardial infarction and cerebral thrombosis, general hypercoagulable states and local hypercoagulable states, such as following angioplasty and coronary bypass operations, and generalized tissue injury as it relates to the inflammatory process. In addition, the antithrombotic agents are useful as anticoagulants in in vitro applications.

The process of blood coagulation, thrombosis, is triggered by a complex proteolytic cascade leading to the formation of thrombin. Thrombin proteolytically removes activation peptides from the Aα-chains and the Bβ-chains of fibrinogen, which is soluble in blood plasma, initiating insoluble fibrin formation. The formation of thrombin from prothrombin is catalyzed by factor Xa.

Anticoagulation currently is achieved by the administration of heparins and coumarins. Parenteral pharmacological control of coagulation and thrombosis is based on inhibition of thrombin through the use of heparins. Heparins act indirectly on thrombin by accelerating the inhibitory effect of endogenous antithrombin III (the main physiological inhibitor of thrombin). Because antithrombin III levels vary in plasma and because clot-bound thrombin seems resistant to this indirect mechanism, heparins can be an ineffective treatment. Because coagulation assays are believed to be associated with efficacy and with safety, heparin levels must be monitored with coagulation assays (particularly the activated partial thromboplastin time (APTT) assay). Coumarins impede the generation of thrombin by blocking the posttranslational gamma-carboxylation in the synthesis of prothrombin and other proteins of this type. Because of their mechanism of action, the effect of coumarins can only develop slowly, 6–24 hours after administration. Further, they are not selective anticoagulants. Coumarins also require monitoring with coagulation assays (particularly the prothrombin time (PT) assay).

Recently, interest has grown in small synthetic molecules which demonstrate potent direct inhibition of thrombin and factor Xa. See, Jeremy J. Edmunds and Stephen T. Rapundalo (Annette M. Doherty, Section Editor), *Annual Reports in Medicinal Chemistry*, (1996), 31, 51–60.

Although the heparins and coumarins are effective anticoagulants, no commercial drug has yet emerged from the small synthetic molecules; and despite the continuing promise for this class of compounds, there still exists a need for anticoagulants which act selectively on factor Xa or thrombin, and which, independent of antithrombin III, exert inhibitory action shortly after administration, preferably by an oral route, and do not interfere with lysis of blood clots, as required to maintain hemostasis.

The present invention is directed to the discovery that the compounds of the present invention, as defined below, are potent inhibitors of factor Xa which may have high bioavailability following oral administration.

According to the invention there is provided a method of inhibiting factor Xa comprising using an effective amount of a factor Xa inhibiting compound of formula I

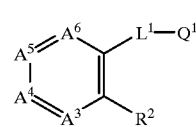

wherein
$A^3$, $A^4$, $A^5$ and $A^6$, together with the two carbons to which they are attached, complete a substituted benzene in which $A^3$ is $CR^3$, $A^4$ is $CR^4$, $A^5$ is $CR^5$, and $A^6$ is $CR^6$;

wherein
$R^3$ is hydrogen, hydroxy, [(1–2C)alkyl]carbonyloxy (which may bear an ω-carboxy substituent), benzoyloxy (which may bear one or more halo, hydroxy methoxy or methyl substitutents), methyl or methoxy;

one of $R^4$ and $R^5$ is hydrogen, methyl, halo, trifluoromethyl, nitro, amino(imino)methyl, amino (hydroxyimino)methyl, $R^fO$—, $R^fO_2C$—, $R^fO_2C$—$CH_2$—, $R^fO_2C$—$CH_2$—O—, 3-methoxycarbonyl-1-oxopropyl, $R^gNH$— or bis(methylsulfonyl)amino;

the other of $R^4$ and $R^5$ is hydrogen, halo or methyl; and
$R^6$ is hydrogen, hydroxy, [(1–2C)alkyl]carbonyloxy (which may bear an (ω-carboxy substituent), benzoyloxy (which may bear one or more halo, hydroxy methoxy or methyl substitutents), methyl or methoxy;

in which $R^f$ is hydrogen, (1–4C)alkyl or benzyl; $R^g$ is hydrogen, acetyl, trifluoroacetyl, phenylalanyl, 2-(t-butoxycarbonylamino)-4-methylsulfinyl-1-oxobutyl or $R^hSO_2$—; and $R^h$ is (1–4C)alkyl, trifluoromethyl, phenyl, 3,5-dimethylisoxazol-4-yl or dimethylamino; or two adjacent residues selected from $R^3$, $R^4$, $R^5$ and $R^6$ together form a benz ring; and the other two are each hydrogen; or $A^3$, $A^4$, $A^5$ and $A^6$, together with the two carbons to which they are attached, complete a substituted heteroaromatic ring in which
(a) one of $A^3$, $A^4$, $A^5$ and $A^6$ is N, and each of the others is $CR^3$, $CR^4$, $CR^5$ or $CR^6$, respectively;
(b) two adjacent residues of $A^3$, $A^4_1$, $A^5$ and $A^6$ together form S, and each of the others is $CR^3$, $CR^4$, $CR^5$ or $CR^6$, respectively;
(c) two non-adjacent residues of $A^3$, $A^4$, $A^5$ and $A^6$ are each N, and each of the others is $CR^3$, $CR^4$, $CR^5$ or $CR^6$, respectively; or
(d) $A^3$ and $A^4$ together form a fused benz ring, and $A^5$ and $A^6$ together form —NH—;

wherein
each of $R^3$, $R^4$, $R^5$ and $R^6$ is hydrogen, or one or two of $R^3$, $R^4$, $R^5$ and $R^6$ is independently chloro, bromo or methyl and the others are hydrogen;

$L^1$ is —NH—CO—, —CO—NH— or —O—$CH_2$— such that —$L^1$—$Q^1$ is —NH—CO—$Q^1$, —CO—NH—$Q^1$ or —O—$CH_2$—$Q^1$ (provided that when —$L^1$—$Q^1$ is —CO—NH—$Q^1$, then $R^2$ is not —CO—NH—$Q^1$ or —CO—NH—$Q^{2B}$);

$Q^1$ is $Q^{1A}$, $Q^{1B}$ or $Q^{1C}$ wherein $Q^{1A}$ is

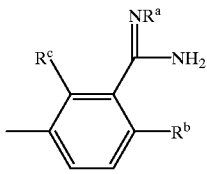

in which $R^a$ is hydrogen, $R^b$ is hydrogen and $R^c$ is hydrogen or hydroxy; or $R^a$ is hydroxy, $R^b$ is hydrogen and $R^c$ is hydrogen; or $R^a$ and $R^b$ together form a methylene or oxo group and $R^c$ is hydrogen;

$Q^{1B}$ is

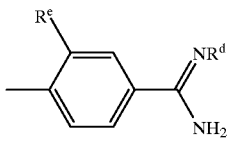

in which $R^d$ is hydrogen or hydroxy and $R^e$ is hydrogen or fluoro; and $Q^{1C}$ is

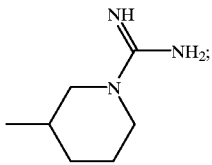

$R^2$ is a residue defined for —NH—CO—$Q^1$ or —CO—NH—$Q^1$; or $R^2$ is —$L^{2A}$—$Q^{2A}$, —$L^{2B}$—$Q^{2B}$, —$L^{2C}$—$Q^{2C}$ or —$L^{2D}$—$Q^{2D}$ wherein $L^{2A}$ is a direct bond; and $Q^{2A}$ is

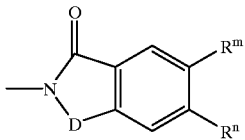

in which D is carbonyl or —CHR$^k$ in which R$^k$ is hydrogen, hydroxy, (1–6C)alkoxy or —CH$_2$—R$^j$ in which R$^j$ is carboxy, [(1–4C)alkoxy]carbonyl or carbamoyl which may bear one or two (1–2C)alkyl substituents on the nitrogen; and one of R$^m$ and R$^n$ is hydrogen and the other is amino, bromo, (1–4C)alkyl or (1–4C)alkoxy, or R$^m$ and R$^n$ together form a benz ring;

$L^{2B}$ is —NH—CO—, —CO—NH—, —O—CO—, —CH$_2$—O— or —O—CH$_2$— such that —$L^{2B}$—$Q^{2B}$ is —NH—CO—$Q^{2B}$, —CO—NH—$Q^{2B}$, —O—CO—$Q^{2B}$, —CH$_2$—O—$Q^{2B}$ or —O—CH$_2$—$Q^{2B}$; and $Q^{2B}$ is

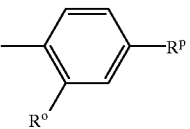

in which $R^o$ is hydrogen, halo, (1–6C)alkyl, (1–4C)alkoxy, benzyloxy or (1–4C)alkylthio; and $R^p$ is 1-hydroxyethyl, 1-hydroxy-1-methylethyl, 1-methoxy-1-methylethyl, 4-piperidinyl, 4-pyridinyl, dimethylaminosulfonyl or —J—$R^q$ in which J is a single bond, methylene, carbonyl, oxo, —S(O)$_q$— (wherein q is 0, 1 or 2), or —NR$^r$— (wherein R$^r$ is hydrogen or methyl); and $R^q$ is (1–6C)alkyl, phenyl, 3-pyridyl or 4-pyridyl;

$L^{2C}$ is —NR$^v$—CO—X—, —NR$^v$—CS—Y—, —CH$_2$—CO—NR$^w$—CH$_2$—, —O—CO—, —O—CH$_2$—, —S—CH$_2$— or —CH$_2$—NR$^x$—CH$_2$— such that —$L^{2C}$—$Q^{2C}$ is —NR$^v$—CO—X—$Q^{2C}$, —NR$^v$—CS—Y—$Q^{2C}$, —CH$_2$—CO—NR$^w$—CH$_2$—$Q^{2C}$, —O—CO—$Q^{2C}$, —O—CH$_2$—$Q^{2C}$, —S—CH$_2$—$Q^{2C}$ or —CH$_2$—NR$^x$—CH$_2$—$Q^{2C}$ in which X is —(CH$_2$)$_x$— (wherein x is 0, 1 or 2), —NR$^w$—CH$_2$—, —O—CH$_2$— or —S—CH$_2$—; Y is —NR$^w$—CH$_2$— or —O—CH$_2$—; each of $R^v$ and $R^w$ is independently hydrogen, benzyl or (1–6C)alkyl which is not branched at the α-position; and $R^x$ is hydrogen, benzyloxycarbonyl or [(1–4C)alkoxy]carbonyl; and $Q^{2C}$ is 1—(4-pyridyl)piperidin-4-yl in which the pyridyl may bear a substituent at its 2-position selected from cyano, aminomethyl, carboxy, hydroxymethyl and (1–2C)alkyl;

$L^{2D}$ is —NH—CO—such that —$L^{2D}$—$Q^{2D}$ is —NH—CO—$Q^{2D}$; and $Q^{2D}$ is selected from 4—(4-pyridinyl)benzyloxy, 9-oxo-9H-fluoren-3-yl, benzo[b]thiophen-2-yl (which may bear a chloro, methyl or methoxy substituent), benzofuran-2-yl (which may bear a chloro, methyl or methoxy substituent), 4—(4-morpholinyl)-4-oxobutyl, and 4-piperidinyl bearing a substituent at the 1-position selected from methylsulfonyl, phenylsulfonyl and —CH$_2$—R$^z$ in which R$^z$ is isopropyl, cyclopropyl, phenyl, furyl, thienyl, 2-thiazolyl, or pyridyl in which the phenyl may bear one or two substituents independently selected from halo, cyano, hydroxy, methoxy, acetoxy, benzyloxy, amino, acetylamino, nitro and 3,4-methylenedioxy, and the thienyl or furyl may bear a methyl or nitro substiutent;

or a prodrug of the compound of formula I; or a pharmaceutically acceptable salt of the compound of formula I or prodrug thereof.

In addition, there is provided the use of a factor Xa inhibiting compound of formula I (or prodrug or salt) as described herein as an active ingredient in the manufacture of a medicament for use in producing an anticoagulant or antithrombotic effect.

The present invention also provides a method of inhibiting coagulation in a mammal comprising administering to a mammal in need of treatment, a coagulation inhibiting dose of a factor Xa inhibiting compound of formula I having any of the definitions herein.

The present invention further provides a method of inhibiting factor Xa comprising administering to a mammal in need of treatment, a factor Xa inhibiting dose of a factor Xa inhibiting compound of formula I having any of the definitions herein.

Further, the present invention provides a method of treating a thromboembolic disorder comprising administering to a mammal in need of treatment, an effective dose of a factor Xa inhibiting compound of formula I having any of the definitions herein.

In addition, there is provided the use of a factor Xa inhibiting compound of formula I having any of the definitions herein for the manufacture of a medicament for treatment of a thromboembolic disorder.

As an additional feature of the invention there is provided a pharmaceutical formulation comprising in association with a pharmaceutically acceptable carrier, diluent or excipient, a prodrug of a factor Xa inhibiting compound of formula I (or of a pharmaceutically acceptable salt thereof) as provided in any of the descriptions herein.

In general, the factor Xa inhibiting compounds of formula I are believed to be novel and, thus, to constitute an additional aspect of the invention. Thus, according to the invention there is provided a novel compound of formula I (or a pharmaceutically acceptable salt thereof) according to any of the definitions herein of a compound of formula I, provided that the compound is not one which is not novel.

A pharmaceutically acceptable salt of an antithrombotic agent of the instant invention includes one which is an acid-addition salt made from a basic compound of formula I and an acid which provides a pharmaceutically acceptable anion, as well as a salt which is made from an acidic compound of formula I and a base which provides a pharmaceutically acceptable cation. Thus, a salt of a novel compound of formula I as provided herein made with an acid or base which affords a pharmaceutically acceptable counterion provides a particular aspect of the invention. Examples of such acids and bases are provided hereinbelow.

As an additional aspect of the invention there is provided a pharmaceutical formulation comprising in association with a pharmaceutically acceptable carrier, diluent or excipient, a novel compound of formula I (or a pharmaceutically acceptable salt thereof) as provided in any of the descriptions herein.

In this specification, the following definitions are used, unless otherwise described: Halo is fluoro, chloro, bromo or iodo. Alkyl, alkoxy, etc. denote both straight and branched groups; but reference to an individual radical such as "propyl" embraces only the straight chain ("normal") radical, a branched chain isomer such as "isopropyl" being specifically denoted. When two adjacent residues form a (fused) benz ring, they form a cis,cis-buta-1,3-dien-1,4-diyl divalent radical.

It will be appreciated that certain compounds of formula I (or salts or prodrugs, etc.) may exist in, and be isolated in, isomeric forms, including tautomeric forms, cis- or trans-isomers, as well as optically active, racemic, or diastereomeric forms. It is to be understood that the present invention encompasses a compound of formula I in any of the tautomeric forms or as an a mixture thereof; or as a mixture of diastereomers, as well as in the form of an individual diastereomer, and that the present invention encompasses a compound of formula I as a mixture of enantiomers, as well as in the form of an individual enantiomer, any of which mixtures or form possesses inhibitory properties against factor Xa, it being well known in the art how to prepare or isolate particular forms and how to determine inhibitory properties against factor Xa by standard tests including those described below.

In addition, a compound of formula I (or salt or prodrug, etc.) may exhibit polymorphism or may form a solvate with water or an organic solvent. The present invention also encompasses any such polymorphic form, any solvate or any mixture thereof.

Particular values are listed below for radicals, substituents, and ranges, for illustration only, and they do not exclude other defined values or other values within defined ranges for the radicals and substituents.

For an alkyl group or the alkyl portion of an alkyl containing group such as, for example alkoxy, a particular value for (1–2C)alkyl is methyl or ethyl, and more particularly is methyl; for (1–4C)alkyl is methyl, ethyl, propyl, isopropyl, butyl, isobutyl, or t-butyl, and more particularly is methyl, isopropyl, butyl or t-butyl; for (1–6C)alkyl is methyl, ethyl, propyl, butyl, pentyl or hexyl, and more particularly is methyl, butyl, or hexyl. A particular value for halo is bromo or chloro, and more particularly is chloro.

A particular compound of formula I is one of formula Ia

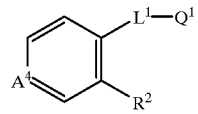

Ia wherein $A^4$, $L^1$, $Q^1$ and $R^2$ have any of the values defined herein.

A particular value for $R^2$ is, for example, (4-isopropylbenzoyl)amino, (4-t-butylbenzoyl)amino, (4-methoxybenzoyl)amino, or [1—(4-pyridyl)piperidin-4-yl]methoxycarbonylamino.

A particular value for $R^4$ or $R^5$ is, for example, hydrogen, hydroxy, acetylamino, carboxymethoxy, carboxymethyl, methoxycarbonyl or carboxy.

One particular compound of formula I as described herein is one in which $L^1$—$Q^1$ is —NH—CO—$Q^1$.

Another particular compound of formula I as described herein is one in which $L^1$—$Q^1$ is —CO—NH—$Q^1$.

A prodrug of a compound of formula I may be one formed in a conventional manner with a functional group of the compound, such as with an amino, hydroxy or carboxy group. One particular prodrug is a carbamate in which an amino (or imino) group of $Q^1$ is substituted by a [(1–4C) alkoxycarbonyl or acetoxymethoxycarbonyl group, for example as described in Examples 26–30.

A compound of formula I may be prepared-by processes which include processes known in the chemical art for the production of any known compounds of formula I or of structurally analogous compounds or by a novel process described herein. A process for the preparation of a novel compound of formula I (or a pharmaceutically acceptable salt thereof), novel processes for the preparation of a compound of formula I and novel intermediates for the manufacture of a compound of formula I as defined above provide further features of the invention and are illustrated by the following procedures in which the meanings of the generic radicals are as defined above, unless otherwise specified. It will be recognized that it may be preferred or necessary to prepare a compound of formula I in which a functional group is protected using a conventional protecting group, then to remove the protecting group to provide the compound of formula I.

Thus, there is provided a process for preparing a novel compound of formula I (or a pharmaceutically acceptable salt thereof) as provided in any of the above descriptions which is selected from any of those described in the examples, including the following.

(A) For a compound of formula I in which the linkage of R² to the ring terminates in —NH—CO—, —NR^v—CO— or —NR^v—CS—, acylating an amine of formula II,

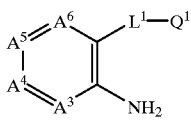

II or a corresponding amine in which the nitrogen bears the group R^v, using a corresponding acid which terminates with the group HO—CO— or HO—CS—, or an activated derivative thereof. Typical activated derivatives include the acid halides, activated esters, including 4-nitrophenyl esters and those derived from coupling reagents, as well as (when the product is a urea or thiourea) isocyanates and isothiocyanates.

(B) For a compound of formula I in which —L¹—Q¹ is —NH—CO—Q¹, acylating an amine of formula III

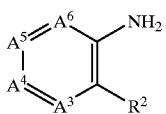

III using an acid of formula HO—CO—Q¹, or an activated derivative thereof.

(C) For a compound of formula I in which —L¹—Q¹ is —CO—NH—Q¹ and R² is of the form —NH—CO—Q², acylating an amine of formula H₂N—Q¹ using a [1,3] oxazine of formula IV,

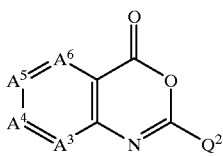

IV wherein Q² represents, for example, Q^{2B}, Q^{2C} or Q2D.

(D) For a compound of formula I in which R² is —L^{2A}—Q^{2A} and D is carbonyl, diacylating a compound of formula II using an anhydride of formula V.

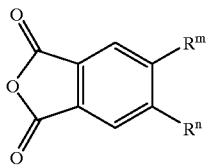

V (E) For a compound of formula I in which Q¹ is Q^{1A} and R^a is hydroxy or in which Q¹ is Q^{1B} and R^d is hydroxy, adding hydroxylamine to a corresponding nitrile to afford the compound with an amino(hydroxyimino)methyl group. Conveniently, the addition is carried out as described in Example 1, Part F.

(F) For a compound of formula I in which Q¹ is Q^{1A} and R^a, R^b and R^c are each hydrogen, or in which Q¹ is Q^{1B} and R^d is hydrogen, hydrogenolyzing the N—O bond of a corresponding compound of formula I in which R^a is hydroxy or in which R^d is hydroxy. The hydrogenolysis conveniently is carried out as described in Example 1, Part G.

(G) For a compound of formula I in which Q¹ is Q^{1A} and R^a, R^b and R^c are each hydrogen, or in which Q¹ is Q^{1B} and R^d is hydrogen, substituting the methylthio group of a corresponding compound bearing a —C(SCH₃)=NH group with an amino group by treatment with ammonia, or a solvate or salt thereof. Conveniently, the substitution is carried out using ammonium acetate as described in Example 15.

(H) For a compound of formula I in which Q¹ is Q^{1A} and R^a and R^b together form a methylene or oxo group, cyclizing a corresponding 4-aminomethyl-3-cyanophenyl or 4-aminooxo-3-cyanophenyl compound. Conveniently, the amine is generated and cyclized in situ, for example as described in Example 8, Part M or in Example 39.

(I) For a compound of formula I in which Q¹ is Q^{1A} and R^c is hydroxy, hydrogenolyzing the N—O bond of a corresponding 3-amino-1,2-benzisoxazol-7-yl compound. Conveniently, the hydrogenolysis is carried out as described in Example 31.

Whereafter, for any of the above procedures, when a functional group is protected using a protecting group, removing the protecting group.

Whereafter, for any of the above procedures, when a pharmaceutically acceptable salt of a compound of formula I is required, it is obtained by reacting the basic form of a basic compound of formula I with an acid affording a physiologically acceptable counterion or the acidic form of an acidic compound of formula I with a base affording a physiologically acceptable counterion or by any other conventional procedure.

A novel intermediate or starting material compound such as, for example, a novel compound of formula II, III or IV, etc., provides a further aspect of the invention.

As mentioned above, a compound corresponding to a compound of formula I but in which a functional group is protected may serve as an intermediate for a compound of formula I. Accordingly, such a protected intermediate for a novel compound of formula I provides a further aspect of the invention. Thus, as one particular aspect of the invention, there is provided a compound corresponding to a novel compound of formula I as defined above in which R⁴ which is hydroxy, but in which the corresponding substituent is —OP^p in place of hydroxy, wherein P^p is a phenol protecting group other than (1–4C)alkyl or benzyl. Phenol protecting groups are well known in the art, for example as described in T. W. Greene and P. G. M. Wuts, "Protecting Groups in Organic Synthesis" (1991). Further, P^p may denote a functionalized resin, for example as disclosed in H. V. Meyers, et al., *Molecular Diversity*, (1995), 1, 13–20.

As mentioned above, the invention includes a pharmaceutically acceptable salt of the factor Xa inhibiting compound defined by the above formula I. A basic compound of this invention possesses one or more functional groups sufficiently basic to react with any of a number of inorganic and organic acids affording a physiologically acceptable counterion to form a pharmaceutically acceptable salt. Acids commonly employed to form pharmaceutically acceptable acid addition salts are inorganic acids such as hydrochloric acid, hydrobromic acid, hydroiodic acid, sulfuric acid, phosphoric acid, and the like, and organic acids such as p-toluenesulfonic acid, methanesulfonic acid, oxalic acid, p-bromobenzenesulfonic acid, carbonic acid, succinic acid, citric acid, benzoic acid, acetic acid, and the like. Examples of such pharmaceutically acceptable salts thus are the sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, gamma-hydroxybutyrate, glycollate, tartrate, methanesulfonate, propanesulfonate, naphthalene-1-sulfonate, naphthalene-2-sulfonate, mandelate, and the like. Preferred pharmaceutically acceptable acid addition salts include those formed with mineral acids such as hydrochloric acid, hydrobromic acid and sulfuric acid.

For a compound of formula I which bears an acidic moiety, such as a carboxy group, a pharmaceutically acceptable salt may be made with a base which affords a pharmaceutically acceptable cation, which includes alkali metal salts (especially sodium and potassium), alkaline earth metal salts (especially calcium and magnesium), aluminum salts and ammonium salts, as well as salts made from physiologically acceptable organic bases such as triethylamine, morpholine, piperidine and triethanolamine.

If not commercially available, a necessary starting material for the preparation of a compound of formula I may be prepared by a procedure which is selected from standard techniques of organic chemistry, including aromatic and heteroaromatic substitution and transformation, from techniques which are analogous to the syntheses of known, structurally similar compounds, and techniques which are analogous to the above described procedures or procedures described in the Examples. It will be clear to one skilled in the art that a variety of sequences is available for the preparation of the starting materials. Starting materials which are novel provide another aspect of the invention.

Selective methods of substitution, protection and deprotection are well known in the art for preparation of a compound such as one of formula II, III, IV or VI discussed above.

Generally, a basic compound of the invention is isolated best in the form of an acid addition salt. A salt of a compound of formula I formed with an acid such as one of those mentioned above is useful as a pharmaceutically acceptable salt for administration of the antithrombotic agent and for preparation of a formulation of the agent. Other acid addition salts may be prepared and used in the isolation and purification of the compounds.

As noted above, the optically active isomers and diastereomers of the compounds of formula I are also considered part of this invention. Such optically active isomers may be prepared from their respective optically active precursors by the procedures described above, or by resolving the racemic mixtures. This resolution can be carried out by derivatization with a chiral reagent followed by chromatography or by repeated crystallization. Removal of the chiral auxiliary by standard methods affords substantially optically pure isomers of the compounds of the present invention or their precursors. Further details regarding resolutions can be obtained in Jacques, et al., *Enantiomers, Racemates, and Resolutions,* John Wiley & Sons, 1981.

The compounds of the invention are believed to selectively inhibit factor Xa over other proteinases and nonenzyme proteins involved in blood coagulation without appreciable interference with the body's natural clot lysing ability (the compounds have a low inhibitory effect on fibrinolysis). Further, such selectivity is believed to permit use with thrombolytic agents without substantial interference with thrombolysis and fibrinolysis.

The invention in one of its aspects provides a method of inhibiting factor Xa in mammals comprising administering to a mammal in need of treatment an effective (factor Xa inhibiting) dose of a compound of formula I.

In another of its aspects, the invention provides a method of treating a thromboembolic disorder comprising administering to a mammal in need of treatment an effective (thromboembolic disorder therapeutic and/or prophylactic amount) dose of a compound of formula I.

The invention in another of its aspects provides a method of inhibiting coagulation in a mammal comprising administering to a mammal in need of treatment an effective (coagulation inhibiting) dose of a compound of formula I.

The factor Xa inhibition, coagulation inhibition and thromboembolic disorder treatment contemplated by the present method includes both medical therapeutic and/or prophylactic treatment as appropriate.

In a further embodiment the invention relates to treatment, in a human or animal, of a condition where inhibition of factor Xa is required. The compounds of the invention are expected to be useful in mammals, including man, in treatment or prophylaxis of thrombosis and hypercoagulability in blood and tissues. Disorders in which the compounds have a potential utility are in treatment or prophylaxis of thrombosis and hypercoagulability in blood and tissues. Disorders in which the compounds have a potential utility, in treatment and/or prophylaxis, include venous thrombosis and pulmonary embolism, arterial thrombosis, such as in myocardial ischemia, myocardial infarction, unstable angina, thrombosis-based stroke and peripheral arterial thrombosis. Further, the compounds have expected utility in the treatment or prophylaxis of atherosclerotic disorders (diseases) such as coronary arterial disease, cerebral arterial disease and peripheral arterial disease. Further, the compounds are expected to be useful together with thrombolytics in myocardial infarction. Further, the compounds have expected utility in prophylaxis for reocclusion after thrombolysis, percutaneous transluminal angioplasty (PTCA) and coronary bypass operations. Further, the compounds have expected utility in prevention of rethrombosis after microsurgery. Further, the compounds are expected to be useful in anticoagulant treatment in connection with artificial organs and cardiac valves. Further, the compounds have expected utility in anticoagulant treatment in hemodialysis and disseminated intravascular coagulation. A further expected utility is in rinsing of catheters and mechanical devices used in patients in vivo, and as an anticoagulant for preservation of blood, plasma and other blood products in vitro. Still further, the compounds have expected utility in other diseases where blood coagulation could be a fundamental contributing process or a source of secondary pathology, such as cancer, including metastasis, inflammatory diseases, including arthritis, and diabetes. The anti-coagulant compound is administered orally or parenterally, e.g. by intravenous infusion (iv), intramuscular injection (im) or subcutaneously (sc).

The specific dose of a compound administered according to this invention to obtain therapeutic and/or prophylactic effects will, of course, be determined by the particular circumstances surrounding the case, including, for example, the compound administered, the rate of administration, the route of administration, and the condition being treated.

A typical daily dose for each of the above utilities is between about 0.01 mg/kg and about 1000 mg/kg. The dose regimen may vary e.g. for prophylactic use a single daily dose may be administered or multiple doses such as 3 or 5 times daily may be appropriate. In critical care situations a compound of the invention is administered by iv infusion at a rate between about 0.01 mg/kg/h and about 20 mg/kg/h and preferably between about 0.1 mg/kg/h and about 5 mg/kg/h.

The method of this invention also is practiced in conjunction with a clot lysing agent e.g. tissue plasminogen activator (t-PA), modified t-PA, streptokinase or urokinase. In cases when clot formation has occurred and an artery or vein is blocked, either partially or totally, a clot lysing agent is usually employed. A compound of the invention can be administered prior to or along with the lysing agent or subsequent to its use, and preferably further is administered along with aspirin to prevent the reoccurrence of clot formation.

The method of this invention is also practiced in conjunction with a platelet glycoprotein receptor (IIb/IIIa) antagonist, that inhibits platelet aggregation. A compound of the invention can be administered prior to or along with the IIb/IIIa antagonist or subsequent to its use to prevent the occurrence or reoccurrence of clot formation.

The method of this invention is also practiced in conjunction with aspirin. A compound of the invention can be administered prior to or along with aspirin or subsequent to its use to prevent the occurrence or reoccurrence of clot formation. As stated above, preferably a compound of the present invention is administered in conjunction with a clot lysing agent and aspirin.

This invention also provides a pharmaceutical composition for use in the above described therapeutic method. A pharmaceutical composition of the invention comprises an effective factor Xa inhibiting amount of a compound of formula I in association with a pharmaceutically acceptable carrier, excipient or diluent.

The active ingredient in such formulations comprises from 0.1 percent to 99.9 percent by weight of the formulation. By "pharmaceutically acceptable" it is meant the carrier, diluent or excipient must be compatible with the other ingredients of the formulation and not deleterious to the recipient thereof.

For oral administration the antithrombotic compound is formulated in gelatin capsules or tablets which may contain excipients such as binders, lubricants, disintegration agents and the like. For parenteral administration the antithrombotic is formulated in a pharmaceutically acceptable diluent e.g. physiological saline (0.9 percent), 5 percent dextrose, Ringer's solution and the like.

The compound of the present invention can be formulated in unit dosage formulations comprising a dose between about 0.1 mg and about 1000 mg. Preferably the compound is in the form of a pharmaceutically acceptable salt such as for example the sulfate salt, acetate salt or a phosphate salt.

An example of a unit dosage formulation comprises 5 mg of a compound of the present invention as a pharmaceutically acceptable salt in a 10 mL sterile glass ampoule. Another example of a unit dosage formulation comprises about 10 mg of a compound of the present invention as a pharmaceutically acceptable salt in 20 mL of isotonic saline contained in a sterile ampoule.

The compounds can be administered by a variety of routes including oral, rectal, transdermal, subcutaneous, intravenous, intramuscular, and intranasal. The compounds of the present invention are preferably formulated prior to administration.

The present pharmaceutical compositions are prepared by known procedures using well known and readily available ingredients. The compositions of this invention may be formulated so as to provide quick, sustained, or delayed release of the active ingredient after administration to the patient by employing procedures well known in the art. In making the compositions of the present invention, the active ingredient will usually be admixed with a carrier, or diluted by a carrier, or enclosed within a carrier which may be in the form of a capsule, sachet, paper or other container. When the carrier serves as a diluent, it may be a solid, semi-solid or liquid material which acts as a vehicle, excipient or medium for the active ingredient. Thus, the compositions can be in the form of tablets, pills, powders, lozenges, sachets, cachets, elixirs, suspensions, emulsions, solutions, syrups, aerosols, (as a solid or in a liquid medium), soft and hard gelatin capsules, suppositories, sterile injectable solutions, sterile packaged powders, and the like.

The following formulation examples are illustrative only and are not intended to limit the scope of the invention in any way. "Active ingredient," of course, means a compound according to formula I or a pharmaceutically acceptable salt or solvate thereof.

Formulation 1: Hard gelatin capsules are prepared using the following ingredients:

|  | Quantity (mg/capsule) |
| --- | --- |
| Active ingredient | 250 |
| Starch, dried | 200 |
| Magnesium stearate | 10 |
| Total | 460 mg |

Formulation 2: A tablet is prepared using the ingredients below:

|  | Quantity (mg/tablet) |
| --- | --- |
| Active ingredient | 250 |
| Cellulose, microcrystalline | 400 |
| Silicon dioxide, fumed | 10 |
| Stearic acid | 5 |
| Total | 665 mg |

The components are blended and compressed to form tablets each weighing 665 mg.

Formulation 3: An aerosol solution is prepared containing the following components:

|  | Weight |
| --- | --- |
| Active ingredient | 0.25 |
| Ethanol | 29.75 |
| Propellant 22 (Chlorodifluoromethane) | 70.00 |
| Total | 100.00 |

The active compound is mixed with ethanol and the mixture added to a portion of the propellant 22, cooled to −30° C. and transferred to a filling device. The required amount is then fed to a stainless steel container and diluted with the remainder of the propellant. The valve units are then fitted to the container.

Formulation 4: Tablets, each containing 60 mg of active ingredient, are made as follows:

| | |
|---|---|
| Active ingredient | 60 mg |
| Starch | 45 mg |
| Microcrystalline cellulose | 35 mg |
| Polyvinylpyrrolidone (as 10% solution in water) | 4 mg |
| Sodium carboxymethyl starch | 4.5 mg |
| Magnesium stearate | 0.5 mg |
| Talc | 1 mg |
| Total | 150 mg |

The active ingredient, starch and cellulose are passed through a No. 45 mesh U.S. sieve and mixed thoroughly. The aqueous solution containing polyvinylpyrrolidone is mixed with the resultant powder, and the mixture then is passed through a No. 14 mesh U.S. sieve. The granules so produced are dried at 50° C. and passed through a No. 18 mesh U.S. Sieve. The sodium carboxymethyl starch, magnesium stearate and talc, previously passed through a No. 60 mesh U.S. sieve, are then added to the granules which, after mixing, are compressed on a tablet machine to yield tablets each weighing 150 mg.

Formulation 5: Capsules, each containing 80 mg of active ingredient, are made as follows:

| | |
|---|---|
| Active ingredient | 80 mg |
| Starch | 59 mg |
| Microcrystalline cellulose | 59 mg |
| Magnesium stearate | 2 mg |
| Total | 200 mg |

The active ingredient, cellulose, starch, and magnesium stearate are blended, passed through a No. 45 mesh U.S. sieve, and filled into hard gelatin capsules in 200 mg quantities.

Formulation 6: Suppositories, each containing 225 mg of active ingredient, are made as follows:

| | |
|---|---|
| Active ingredient | 225 mg |
| Saturated fatty acid glycerides | 2,000 mg |
| Total | 2,225 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

Formulation 7: Suspensions, each containing 50 mg of active ingredient per 5 mL dose, are made as follows:

| | |
|---|---|
| Active ingredient | 50 mg |
| Sodium carboxymethyl cellulose | 50 mg |
| Syrup | 1.25 mL |
| Benzoic acid solution | 0.10 mL |
| Flavor | q.v. |
| Color | q.v. |
| Purified water to total | 5 mL |

The active ingredient is passed through a No. 45 mesh U.S. sieve and mixed with the sodium carboxymethyl cellulose and syrup to form a smooth paste. The benzoic acid solution, flavor and color are diluted with a portion of the water and added, with stirring. Sufficient water is then added to produce the required volume.

Formulation 8: An intravenous formulation may be prepared as follows:

| | |
|---|---|
| Active ingredient | 100 mg |
| Isotonic saline | 1,000 mL |

The solution of the above ingredients generally is administered intravenously to a subject at a rate of 1 mL per minute.

The ability of a compound of the present invention to be an effective and orally active factor Xa inhibitor may be evaluated in one or more of the following assays or in other standard assays known to those in the art.

The inhibition by a compound of the inhibition of a serine protease of the human blood coagulation system or of the fibrinolytic system, as well as of trypsin, is determined in vitro for the particular enzyme by measuring its inhibitor binding affinity in an assay in which the enzyme hydrolyzes a particular chromogenic substrate, for example as described in Smith, G. F.; Gifford-Moore, D.; Craft, T. J.; Chirgadze, N.; Ruterbories, K. J.; Lindstrom, T. D.; Satterwhite, J. H. Efegatran: A New Cardiovascular Anticoagulant. *New Anticoagulants for the Cardiovascular Patient;* Pifarre, R., Ed.; Hanley & Belfus, Inc.: Philadelphia, 1997; pp. 265–300. The inhibitor binding affinity is measured as apparent association constant Kass which is the hypothetical equilibrium constant for the reaction between enzyme and the test inhibitor compound (I).

$$Enzyme + I \rightleftharpoons Enzyme - I$$

$$Kass = \frac{[Enzyme - I]}{[(Enzyme) \times (I)]}$$

Conveniently, enzyme inhibition kinetics are performed in 96-well polystyrene plates and reaction rates are determined from the rate of hydrolysis of appropriate p-nitroanilide substrates at 405 nm using a Thermomax plate reader from Molecular Devices (San Francisco, Calif.). The same protocol is followed for all enzymes studied: 50 $\mu$L buffer (0.03 M Tris, 0.15 M NaCl pH 7) in each well, followed by 25 $\mu$L of inhibitor solution (in 100% methanol, or in 50% v:v aqueous methanol) and 25 $\mu$L enzyme solution; within two minutes, 150 $\mu$L aqueous solution of chromogenic substrate (0.25 mg/mL) is added to start the enzymatic reaction. The rates of chromogenic substrate hydrolysis reactions provide a linear relationship with the enzymes studied such that free enzyme can be quantitated in reaction mixtures. Data is analyzed directly as rates by the Softmax program to produce [free enzyme] calculations for tight-binding Kass determinations. For apparent Kass determinations, 1.34 nM human factor Xa is used to hydrolyze 0.18 mM BzIle-Glu-Gly-Arg-pNA; 5.9 nM human thrombin or 1.4 nM bovine trypsin is used to hydrolyze 0.2 mM BzPhe-Val-Arg-pNA; 3.4 $_1$nM human plasmin is used with 0.5 mM HD-Val-Leu-Lys-pNA; 1.2 nM human nt-PA is used with 0.81 mM HD-Ile-Pro-Arg-pNA; and 0.37 nM urokinase is used with 0.30 mM pyro-gfsGlu-Gly-Arg-pNA.

Kass is calculated for a range of concentrations of test compounds and the mean value reported in units of liter per mole. In general, a factor Xa inhibiting compound of formula I of the instant invention exhibits a Kass of 0.1 to $0.5 \times 10^6$ L/mole or much greater.

The factor Xa inhibitor preferably should spare fibrinolysis induced by urokinase, tissue plasminogen activator (t-PA) and streptokinase. This would be important to the therapeutic use of such an agent as an adjunct to streptokinase, tp-PA or urokinase thrombolytic therapy and to the use of such an agent as an endogenous fibrinolysis-sparing (with respect to t-PA and urokinase) antithrombotic agent. In addition to the lack of interference with the amidase activity of the fibrinolytic proteases, such fibrinolytic system sparing can be studied by the use of human plasma clots and their lysis by the respective fibrinolytic plasminogen activators.

Materials

Dog plasma is obtained from conscious mixed-breed hounds (either sex Butler Farms, Clyde, N.Y., U.S.A.) by venipuncture into 3.8 percent citrate. Fibrinogen is prepared from fresh dog plasma and human fibrinogen is prepared from in-date ACD human blood at the fraction I-2 according to previous procedures and specification. Smith, *Biochem. J.*, 185, 1–11 (1980; and Smith, et al., *Biochemistry*, 11, 2958–2967, (1972). Human fibrinogen (98 percent pure/plasmin free) is from American Diagnostica, Greenwich, Conn. Radiolabeling of fibrinogen I-2 preparations is performed as previously reported. Smith, et al., *Biochemistry*, 11, 2958–2967, (1972). Urokinase is purchased from Leo Pharmaceuticals, Denmark, as 2200 Ploug units/vial. Streptokinase is purchased from Hoechst-Roussel Pharmaceuticals, Somerville, N.J.

Methods—Effects on Lysis of Human Plasma Clots by t-PA

Human plasma clots are formed in micro test tubes by adding 50 $\mu$L thrombin (73 NIH unit/mL) to 100 $\mu$L human plasma which contains 0.0229 $\mu$Ci 125-iodine labeled fibrinogen. Clot lysis is studied by overlaying the clots with 50 $\mu$L of urokinase or streptokinase (50, 100, or 1000 unit/mL) and incubating for 20 hours at room temperature. After incubation the tubes are centrifuged in a Beckman Microfuge. 25 $\mu$L of supernate is added into 1.0 mL volume of 0.03 M tris/0.15 M NaCl buffer for gamma counting. Counting controls 100 percent lysis are obtained by omitting thrombin (and substituting buffer). The factor Xa inhibitors are evaluated for possible interference with fibrinolysis by including the compounds in the overlay solutions at 1, 5, and 10 $\mu$g/mL concentrations. Rough approximations of $IC_{50}$ values are estimated by linear extrapolations from data points to a value which would represent 50 percent of lysis for that particular concentration of fibrinolytic agent.

Anticoagulant Activity

Materials

Dog plasma and rat plasma are obtained from conscious mixed-breed hounds (either sex, Butler Farms, Clyde, N.Y., U.S.A.) or from anesthetized male Sprague-Dawley rats (Harlan Sprague-Dawley, Inc., Indianapolis, Ind., U.S.A:.) by venipuncture into 3.8 percent citrate. Fibrinogen is prepared from in-date ACD human blood as the fraction I-2 according to previous procedures and specifications. Smith, *Biochem. J.*, 185, 1–11 (1980); and Smith, et al., *Biochemistry*, 11, 2958–2967 (1972). Human fibrinogen is also purchased as 98 percent pure/plasmin free from American Diagnostica, Greenwich, Conn. Coagulation reagents Actin, Thromboplastin, Innovin and Human plasma are from Baxter Healthcare Corp., Dade Division, Miami, Fla. Bovine thrombin from Parke-Davis (Detroit, Michigan) is used for coagulation assays in plasma.

Methods

Anticoagulation Determinations

Coagulation assay procedures are as previously described. Smith, et al., *Thrombosis Research*, 50, 163–174 (1988). A CoAScreener coagulation instrument (American LABor, Inc.) is used for all coagulation assay measurements. The prothrombin time (PT) is measured by adding 0.05 mL saline and 0.05 mL Thromboplastin-C reagent or recombinant human tissue factor reagent (Innovin) to 0.05 mL test plasma. The activated partial thromboplastin time (APTT) is measured by incubation of 0.05 mL test plasma with 0.05 mL Actin reagent for 120 seconds followed by 0.05 mL $CaCl_2$ (0.02 M). The thrombin time (TT) is measured by adding 0.05 mL saline and 0.05 mL thrombin (10 NIH units/mL) to 0.05 mL test plasma. The compounds of formula I are added to human or animal plasma over a wide range of concentrations to determine prolongation effects on the APTT, PT, and TT assays. Linear extrapolations are performed to estimate the concentrations required to double the clotting time for each assay.

Animals

Male Sprague Dawley rats (350–425 gm, Harlan Sprague Dawley Inc., Indianapolis, Ind.) are anesthetized with xylazine (20-mg/kg, s.c.) and ketamine (120 mg/kg, s.c.) and maintained on a heated water blanket (37° C.). The jugular vein(s) is cannulated to allow for infusions.

Arterio-Venous shunt model

The left jugular vein and right carotid artery are cannulated with 20 cm lengths of polyethylene PE 60 tubing. A 6 cm center section of larger tubing (PE 190) with a cotton thread (5 cm) in the lumen, is friction fitted between the longer sections to complete the arterio-venous shunt circuit. Blood is circulated through the shunt for 15 min before the thread is carefully removed and weighed. The weight of a wet thread is subtracted from the total weight of the thread and thrombus (see J. R. Smith, *Br J Pharmacol*, 77:29, 1982).

FeCl3 Model of Arterial Injury

The carotid arteries are isolated via a midline ventral cervical incision. A thermocouple is placed under each artery and vessel temperature is recorded continuously on a strip chart recorder. A cuff of tubing (0.058 ID×0.077 OD×4 mm, Baxter Med. Grade Silicone), cut longitudinally, is placed around each carotid directly above the thermocouple. $FeCl_3$ hexahydrate is dissolved in water and the concentration (20 percent) is expressed in terms of the actual weight of $FeCl_3$ only. To injure the artery and induce thrombosis, 2.85 $\mu$L is pipetted into the cuff to bathe the artery above the thermocouple probe. Arterial occlusion is indicated by a rapid drop in temperature. The time to occlusion is reported in minutes and represents the elapsed time between application of $FeCl_3$ and the rapid drop in vessel temperature (see K. D. Kurz, *Thromb. Res.*, 60:269, 1990).

Coagulation Parameters

Plasma thrombin time (TT) and activated partial thromboplastin time (APTT) are measured with a fibrometer. Blood is sampled from a jugular catheter and collected in syringe containing sodium citrate (3.8 percent, 1 part to 9 parts blood). To measure TT, rat plasma (0.1 mL) is mixed with saline (0.1 mL) and bovine thrombin (0.1 mL, 30 U/mL in TRIS buffer; Parke Davis) at 37° C. For APTT, plasma (0.1 mL) and APTT solution (0.1 mL, Organon Teknika) are incubated for 5 minutes (37° C.) and $CaCl_2$ (0.1 mL, 0.025 M) is added to start coagulation. Assays are done in duplicate and averaged.

Index of Bioavailability

Bioavailability studies may be conducted as follows. Compounds are administered as aqueous solutions to male Fisher rats, intravenously (iv) at 5 mg/kg via tail vein injection and orally (po) to fasted animals at 20 mg/kg by gavage. Serial blood samples are obtained at 5, 30, 120, and 240 minutes postdose following intravenous administration and at 1, 2, 4, and 6 hours after oral dosing. Plasma is analyzed for drug concentration using an HPLC procedure involving C8 Bond Elute (Varion) cartridges for sample preparation and a methanol/30 nM ammonium acetate buffer (pH 4) gradient optimized for each compound. % Oral bioavailability is calculated by the following equation:

$$\% \text{ Oral bioavailability} = \frac{AUC\ po}{AUC\ iv} \times \frac{Dose\ iv}{Dose\ po} \times 100$$

where AUC is area under the curve calculated from the plasma level of compound over the time course of the experiment following oral (AUC po) and intravenous (AUC iv) dosing.

Compounds

Compound solutions are prepared fresh daily in normal saline and are injected as a bolus or are infused starting 15 minutes before and continuing throughout the experimental perturbation which is 15 minutes in the arteriovenous shunt model and 60 minutes in the $FeCl_3$ model of arterial injury and in the spontaneous thrombolysis model. Bolus injection volume is 1 mL/kg for i.v., and 5 mL/kg for p.o., and infusion volume is 3 mL/hr.

Statistics

Results are expressed as means+/−SEM. One-way analysis of variance is used to detect statistically significant differences and then Dunnett's test is applied to determine which means are different. Significance level for rejection of the null hypothesis of equal means is $P<0.05$.

Animals

Male dogs (Beagles; 18 months–2 years; 12–13 kg, Marshall Farms, North Rose, N.Y. 14516) are fasted overnight and fed Purina certified Prescription Diet (Purina Mills, St. Louis, Mo.) 240 minutes after dosing. Water is available ad libitum. The room temperature is maintained between 66–74° F.; 45–50 percent relative humidity; and lighted from 0600–1800 hours.

Pharmacokinetic Model.

Test compound is formulated immediately prior to dosing by dissolving in sterile 0.9 percent saline to a 5 mg/mL preparation. Dogs are given a single 2 mg/kg dose of test compound by oral gavage. Blood samples (4.5 mL) are taken from the cephalic vein at 0.25, 0.5, 0.75, 1, 2, 3, 4 and 6 hours after dosing. Samples are collected in citrated Vacutainer tubes and kept on ice prior to reduction to plasma by centrifugation. Plasma samples are analyzed by HPLC MS. Plasma concentration of test compound is recorded and used to calculate the pharmacokinetic parameters: elimination rate constant, Ke; total clearance, Clt; volume of distribution, $V_D$; time of maximum plasma test compound concentration, Tmax; maximum concentration of test compound of Tmax, Cmax; plasma half-life, t0.5; and area under the curve, A.U.C.; fraction of test compound absorbed, F.

Canine Model of Coronary Artery Thrombosis

Surgical preparation and instrumentation of the dogs are as described in Jackson, et al., *Circulation*, 82, 930–940 (1990). Mixed-breed hounds (aged 6–7 months, either sex, Butler Farms, Clyde, N.Y., U.S.A.) are anesthetized with sodium pentobarbital (30 mg/kg intravenously, i.v.), intubated, and ventilated with room air. Tidal volume and respiratory rates are adjusted to maintain blood $PO_2$, $PCO_2$, and pH within normal limits. Subdermal needle electrodes are inserted for the recording of a lead II ECG.

The left jugular vein and common carotid artery are isolated through a left mediolateral neck incision. Arterial blood pressure (ABP) is measured continuously with a precalibrated Millar transducer (model (MPC-500, Millar Instruments, Houston, Tex., U.S.A.) inserted into the carotid artery. The jugular vein is cannulated for blood sampling during the experiment. In addition, the femoral veins of both hindlegs are cannulated for administration of test compound.

A left thoracotomy is performed at the fifth intercostal space, and the heart is suspended in a pericardial cradle. A 1- to 2-cm segment of the left circumflex coronary artery (LCX) is isolated proximal to the first major diagonal ventricular branch. A 26-gauge needle-tipped wire anodal electrode (Teflon-coated, 30-gauge silverplated copper wire) 3–4 mm long is inserted into the LCX and placed in contact with the intimal surface of the artery (confirmed at the end of the experiment). The stimulating circuit is completed by placing the cathode in a subcutaneous (s.c.) site. An adjustable plastic occluder is placed around the LCX, over the region of the electrode. A precalibrated electromagnetic flow probe (Carolina Medical Electronics, King, N.C., U.S.A.) is placed around the LCX proximal to the anode for measurement of coronary blood flow (CBF). The occluder is adjusted to produce a 40–50 percent inhibition of the hyperemic blood flow response observed after 10-s mechanical occlusion of the LCX. All hemodynamic and ECG measurements are recorded and analyzed with a data acquisition system (model M3000, Modular Instruments, Malvern, Pa. U.S.A.).

Thrombus Formation and Compound Administration Regimens

Electrolytic injury of the intima of the LCX is produced by applying 100-$\mu$A direct current (DC) to the anode. The current is maintained for 60 min and then discontinued whether the vessel has occluded or not. Thrombus formation proceeds spontaneously until the LCX is totally occluded (determined as zero CBF and an increase in the S-T segment). Compound administration is started after the occluding thrombus is allowed to age for 1 hour. A 2-hour infusion of the compounds of the present invention at doses of 0.5 and 1 mg/kg/hour is begun simultaneously with an infusion of thrombolytic agent (e.g. tissue plasminogen activator, streptokinase, APSAC). Reperfusion is followed for 3 hour after administration of test compound. Reocclusion of coronary arteries after successful thrombolysis is defined as zero CBF which persisted for at least 30 minutes.

Hematology and Template Bleeding Time Determinations

Whole blood cell counts, hemoglobin, and hematocrit values are determined on a 40-$\mu$L sample of citrated (3.8 percent) blood (1 part citrate:9 parts blood) with a hematology analyzer (Cell-Dyn 900, Sequoia-Turner. Mount View, Calif., U.S.A.). Gingival template bleeding times are determined with a Simplate II bleeding time device (Organon Teknika Durham, N.C., U.S.A.). The device is used to make 2 horizontal incisions in the gingiva of either the upper or lower left jaw of the dog. Each incision is 3 mm wide×2 mm deep. The incisions are made, and a stopwatch is used to determine how long bleeding occurs. A cotton swab is used to soak up the blood as it oozes from the incision. Template bleeding time is the time from incision to stoppage of bleeding. Bleeding times are taken just before administration of test compound (0 min), 60 min into infusion, at conclusion of administration of the test compound (120 min), and at the end of the experiment. All data are analyzed by one-way analysis of variance (ANOVA) followed by Student-Neuman-Kuels post hoc t test to determine the level of significance. Repeated-measures ANOVA are used to determine significant differences between time points during the experiments. Values are determined to be statistically different at least at the level of $p<0.05$. All values are mean±SEM. All studies are conducted in accordance with the guiding principles of the American Physiological Society. Further details regarding the procedures are described in Jackson, et al., *J. Cardiovasc. Pharmacol.*, (1993), 21, 587–599.

The following Examples are provided to further describe the invention and are not to be construed as limitations thereof.

The abbreviations, symbols and terms used in the examples have the following meanings.

Ac=acetyl
AIBN=azobisisobutyronitrile
Anal.=elemental analysis
aq=aqueous
Bn or Bzl=benzyl
Boc=t-butyloxycarbonyl
Bu=butyl
n-BuLi=butyllithium
Calc=calculated
conc=concentrated
DCC=dicyclohexylcarbodiimide
DMAP=4-dimethylaminopyridine
DMF=dimethylformamide
DMSO=dimethylsulfoxide
EDC=1-(3-dimethylaminopropyl)-3-ethylcarbodiimide hydrochloride
eq=(molar) equivalent
Et=ethyl
EtOAc=ethyl acetate
Et$_3$N=triethylamine
Et$_2$O=diethyl ether
EtOH=ethanol
Hex hexanes
HOAt=1-hydroxy-7-azabenzotriazole
HOBT=1-hydroxybenzotriazole
HPLC=High Performance Liquid Chromatography
HRMS=high resolution mass spectrum
i-PrOH=isopropanol
IR=Infrared Spectrum
Me=methyl
MeI=methyl iodide
MeOH=methanol
MS(FAB)=fast atom bombardment mass spectrum
MS(FD)=field desorption mass spectrum
MS(IS)=ion spray mass spectrum
NBS=N-bromosuccinimide
NMR=Nuclear Magnetic Resonance
Ph=phenyl
i-Pr=isopropyl
RPHPLC=Reversed Phase High Performance Liquid Chromatography
satd=saturated
SiO$_2$=silica gel
TBS=tert-butyldimethylsilyl
TFA=trifluoroacetic acid
THF=tetrahydrofuran
TIPS=triisopropylsilyl
TLC=thin layer chromatography
tosyl=p-toluenesulfonyl
triflic acid=trifluoromethanesulfonic acid Unless otherwise stated, pH adjustments and work up are with aqueous acid or base solutions. $^1$H-NMR indicates a satisfactory NMR spectrum was obtained for the compound described. IR indicates a satisfactory infra red spectrum was obtained for the compound described.

For consistency and clarity, a number of compounds are named as substituted diamine deriviatives.

EXAMPLE 1

Preparation of N$^1$-[3-(amino(imino)methyl)benzoyl]-N$^2$-(4-isopropylbenzoyl)-4-hydroxy-1,2-benzenediamine hydrochloride

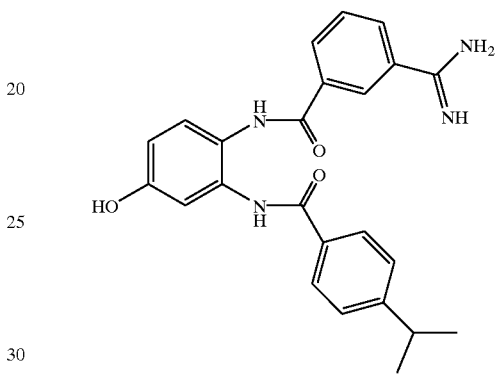

A) 2-nitro-4-(dimethyl-t-butylsiloxy)aniline

To a mixture of 4-amino-3-nitrophenol (10.07 g, 65.3 mmol) and DMF (20 mL) was added imidazole (11.15 g, 163.8 mmol) followed by t-butyldimethylsilyl chloride (11.82 g, 78.4 mmol) in several portions. After 5 h, the reaction was diluted with EtOAc (150 mL) and washed with water (5×20 mL). The organic layer was MgSO$_4$, dried, filtered, and concentrated. The residue was chromatographed (10% EtOAc/hexanes to 20% EtOAc/hexanes) to give the title compound as a solid (17.06 g, 97%); mp 80–83° C.; IR (CHCl$_3$): 3399, 2932, 1519, 1242, 866 cm$^{-1}$; NMR (300 MHz, CDCl$_3$): δ0.19 (s, 6H), 0.97 (s, 9H), 6.70 (d, 1H, J=9.0), 6.95 (d, 1H, J=3.0), 7.56 (d, 1H, J=2.7); MS(FD): 268.2.

Analysis for C$_{12}$H$_{20}$N$_2$O$_3$Si: Calculated: C, 53.70; H, 7.51; N 10.44. Found: C, 53.47; H, 7.50; N 10.31.

B) N-(3-cyanobenzoyl)-2-nitro-4-(dimethyl-t-butylsiloxy)aniline

To a mixture of 2-nitro-4-(dimethyl-t-butylsiloxy)aniline (10.01 g, 37.30 mmol) and CH$_2$Cl$_2$ (400 mL) at 0° C was added pyridine (3.4 mL, 42.0 mmol) followed by the 3-cyanobenzoyl chloride (8.65 g, 52.2 mmol). The reaction was allowed to warm to room temperature and stirred for 1 h. The reaction was diluted with CH$_2$Cl$_2$ (800 mL) and washed with sat. aq. NH$_4$Cl (2×200 mL). The organic layer was MgSO$_4$ dried, filtered, and concentrated. The residue was chromatographed (20% EtOAc/hexanes) to give the title compound as a solid (13.94 g, 94%); IR(CHCl$_3$): 2932, 1689, 1508, 1289, 863 cm$^{-1}$; NMR(300 MHz, CDCl$_3$): δ0.27 (s, 6H), 1.02 (s, 9H), 7.27 (s, 1H), 7.70 (m, 2H), 7.90 (d, J=7.8, 1H), 8.16 (d, J=1.2, 1H), 8.30 (s, 1H), 8.79 (d, J=9.3, 1H), 11.15 (br s, 1H); MS(FD): 397.0.

Analysis for C$_{20}$H$_{23}$N$_3$O$_4$Si: Calculated: C, 60.43; H, 5.83; N, 10.57. Found: C, 60.58; H, 5.79; N, 10.61.

C) N¹-(3-cyanobenzoyl)-4-(dimethyl-t-butylsiloxy)-1,2-benzenediamine

A mixture of N-(3-cyanobenzoyl)-2-nitro-4-(dimethyl-t-butylsiloxy)aniline (5.00 g, 12.6 mmol), 10% Pd/C (2.5 g), EtOH (160 mL), and THF (160 mL) was hydrogenated at 1 atm for 12 h. The reaction was filtered through diatomaceous earth with hot methanolic washes. The filtrate was concentrated and chromatographed (20% EtOAc/hexanes to 30% EtOAc/hexanes) to give the title compound as a solid (2.72 g, 59%).

D) N¹-(3-cyanobenzoyl)-N²-(4-isopropylbenzoyl)-4-(dimethyl-t-butylsiloxy)-1,2-benzenediamine To a mixture of 4-isopropyl benzoic acid (1.66 g, 10.1 mmol) and toluene (87 mL) was added pyridine (1.04 mL, 12.88 mmol) and thionyl chloride (0.96 mL, 13.15 mmol). The reaction mixture was heated to 80° C. for 3 h, cooled, and concentrated. The crude 4-isopropyl benzoyl chloride was used without further purification as described below.

To a mixture of N¹-(3-cyanobenzoyl)-4-(dimethyl-t-butylsiloxy)-1,2-benzenediamine (2.63 g, 7.17 mmol) and $CH_2Cl_2$ (45 mL) at 0° C. was added pyridine (0.65 mL, 8.0 mmol) followed by a solution of the 4-isopropyl benzoyl chloride (10.1 mmol) in $CH_2Cl_2$ (90 mL). The reaction was allowed to warm to room temperature and stirred for 10 m. The reaction was diluted with $CH_2Cl_2$ (200 mL) and washed with sat. aq. $NH_4Cl$ (2×50 mL). The organic layer was $MgSO_4$ dried filtered, and concentrated. The residue was chromatographed (10% EtOAc/hexanes to 20% EtOAc/hexanes) to give the title compound as a solid (3.04 g, 83%); IR(CHCl₃): 2962, 1656, 1610, 1513, 1473, 1295 cm⁻¹; NMR(300 MHz, CDCl₃): δ0.16 (s, 6H), 0.95 (s, 9H), 1.29 (s, 3H), 1.31 (s, 3H), 3.00 (m, 1H), 6.68 (d, 1H, J=9.0), 6.86 (s, 1H), 7.38 (d, 2H, J=8.1), 7.50 (d, 1H, J=9.0), 7.61 (m, 1H), 7.81 (d, 1H, J=6.3), 7.89 (d, 2H, J=7.1), 8.16 (d, 1H, J=9.3), 8.29 (s, 1H), 8.58 (br s, 1H), 9.40 (br s, 1H); MS(FD): 513.1.

Analysis for $C_{30}H_{35}N_3O_3Si$: Calculated: C, 70.14; H, 6.87; N, 8.18. Found: C, 70.30; H, 7.01; N, 8.35.

E) N¹-(3-cyanobenzoyl)-N²-(4-isopropylbenzoyl)-4-hydroxy-1,2-benzenediamine

To a mixture of N¹-(3-cyanobenzoyl)-N²-(4-isopropylbenzoyl)-4-(dimethyl-t-butylsiloxy)-1,2-benzenediamine (1.57 g, 3.05 mmol) THF (30 mL) at 0° C. was added a THF solution of TBAF (3.1 mL, 3.1 mmol). After 1 h, the reaction was quenched with water (35 mL) and extracted with ether (2×200 mL). The combined organic layers was $MgSO_4$ dried, filtered, and concentrated. The residue was chromatographed (1:1 EtOAc/hexanes) to give the title compound as a solid (1.10 g, 91%); IR(KBr): 3277, 1629, 1600, 1535, 1478, 1299 cm⁻¹; NMR(300 MHz, d₆-DMSO): δ10.02 (s, 1H), 9.70 (s, 1H), 9.56 (s, 1H), 8.31 (s, 1H), 8.18 (d, J=7.5, 1H), 8.01 (d, J=7.2, 1H), 7.79 (d, J=8.1, 2H), 7.70 (m, 1H), 7.34–7.21 (m, 4H), 6.63 (d, J=9.0, 1H), 2.90 (m, 1H), 1.17 (s, 3H), 1.15 (s, 3H); MS(FD): 399.1.

Analysis for $C_{24}H_{21}N_3O_3$: Calculated: C, 72.17; H, 5.30; N, 10.52. Found: C, 71.88; H, 5.32; N, 10.24.

F) N¹-[3-(amino(hydroxyimino)methyl)benzoyl]-N²-(4-isopropylbenzoyl)-4-hydroxy-1,2-benzenediamine To a mixture of N¹-(3-cyanobenzoyl)-N²-(4-isopropylbenzoyl)-4-hydroxy-1,2-benzenediamine (445 mg, 1.11 mmol) and absolute EtOH (30 mL) was added hydroxylamine hydrochloride (125 mg, 1.80 mmol) followed by triethylamine (0.3 mL, 2.15 mmol). The resulting mixture was heated to 80° C. for 2 h, cooled to room temperature, and filtered to give the title compound as a solid (238 mg, 0.55 mmol, 50%); NMR(300 MHz, d₆-DMSO): δ9.92 (s, 1H), 9.76 (s, 1H), 9.69 (s, 1H), 9.53 (s, 1H), 8.23 (s, 1H), 7.84 (m, 4H), 7.49 (m, 1H), 7.29 (m, 4H), 6.65 (d, J=9.0, 1H), 5.85 (s, 2H), 2.92 (m, 1H), 1.19 (s, 3H), 1.17 (s, 3H); MS(FD): 432.2.

Analysis for $C_{24}H_{24}N_4O_4$: Calculated: C, 66.65; H, 5.59; N, 12.96. Found: C, 65.75; H, 5.43; N, 12.42.

G) N¹-[3-(amino(imino)methyl)benzoyl]-N²-(4-isopropylbenzoyl)-4-hydroxy-1,2-benzenediamine hydrochloride A mixture of N¹-[3-(amino(hydroxyimino)methyl)benzoyl]N²-(4-isopropylbenzoyl)-4-hydroxy-1,2-benzenediamine (209 mg, 0.48 mmol), EtOH (5 mL), H₂O (2.5 mL), 1N HCl (0.5 mL, 0.5 mmol), and 10% Pd/C (217 mg) was hydrogenated at 1 atm. for 14 h. The reaction was filtered through diatomaceous earth with hot methanolic washes. The filtrate was concentrated and the residue was resubjected to the hydrogenation conditions using 10% Pd/C (189 mg). After 6 h, the reaction mixture was filtered through diatomaceous earth with hot methanolic washes. The filtrate was concentrated to give the title compound as a solid (134 mg, 62%); NMR(300 MHz, DMSO-d₆): δ10.27 (s, 1H), 9.89 (s, 1H), 9.45 (s, 2H), 9.14 (s, 2H), 8.42 (s, 1H), 8.23 (d, J=7.5, 1H), 7.94 (d, J=7.2, 1H), 7.86 (d, J=8.1, 2H), 7.73 (t, J=7.8, 1H), 7.28 (m, 4H), 6.65 (d, J=8.7, 1H), 2.90 (m, 1H), 1.19 (s, 3H), 1.17 (s, 3H); MS(FD): 399.2 (M—OH).

Analysis for $C_{24}H_{24}N_4O_3 \cdot HCl \cdot 2.5\ H_2O$:
C, 57.89; H, 6.07; N, 11.25. Found: C, 57.21; H, 5.32; N, 10.90.

EXAMPLE 2

Preparation of N¹-[3-(amino(imino)methyl)benzoyl]-N²-(4-isopropylbenzoyl)-4-carboxymethoxy-1,2-benzenediamine dihydrochloride

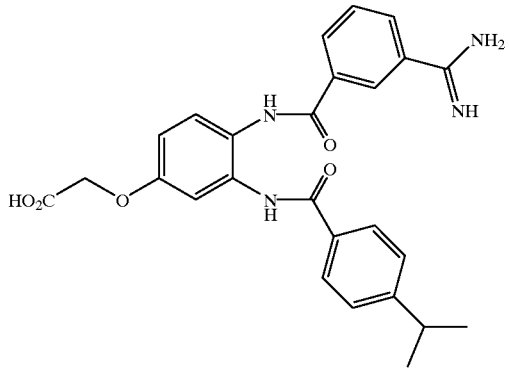

A) N¹-(3-cyanobenzoyl)-N²-(4-isopropylbenzoyl)-4-(benzyloxycarbonylmethoxy)-1,2-benzenediamine To a mixture of N¹-(3-cyanobenzoyl)-N²-(4-isopropylbenzoyl)-4-hydroxy-1,2-benzenediamine (502 mg, 1.26 mmol), acetone (15 mL), and potassium carbonate (216 mg, 1.56 mmol) was added by benzyl 2-bromoacetate (0.4 mL, 2.52 mmol). After stirring overnight, the reaction was concentrated and the residue was chromatographed (100% $CH_2Cl_2$ to 10% EtOAc/$CH_2Cl_2$) to give the title compound as a solid (532 mg, 77%); IR(CHCl₃): 2965, 1759, 1654, 1610, 1514, 1175 cm⁻¹; NMR(300 MHz, CDCl₃): δ1.28 (s, 3H), 1.30 (s, 3H), 3.00 (m, 1H), 4.50 (s, 2H), 5.22 (s, 2H), 6.71 (d, 1H, J=9.3), 6.93 (s, 1H), 7.31 (m, 7H), 7.54 (d, 1H, J=21), 7.60 (t, 1H, J=7.8), 7.78 (d, 1H, J=8.7), 7.89 (d, 2H, J=8.1), 8.19 (d, 1H, J=8.1), 8.30 (s, 1H), 8.74 (br s, 1H), 9.48 (br s, 1H); MS(FD): 547.

Analysis for $C_{33}H_{29}N_3O_5$: Calculated: C, 72.38; H, 5.34; N, 7.67. Found: C, 72.55; H, 5.32; N, 7.78.

B) $N^1$-[3-(amino(hydroxyimino)methyl)benzoyl]-$N^2$-(4-isopropylbenzoyl)-4-(benzyloxycarbonylmethoxy)-1,2-benzenediamine Using a procedure similar to Example 1F except starting with $N^1$-(3-cyanobenzoyl)-$N^2$-(4-isopropylbenzoyl)-4-(benzyloxycarbonylmethoxy)-1,2-benzenediamine (532 mg, 0.97 mmol), a residue was obtained after concentrating the reaction mixture. The residue was chromatographed (10% EtOAc/$CH_2Cl_2$ to 50% EtOAc/$CH_2Cl_2$) to give the title compound as a solid (317 mg, 56%); NMR(300 MHz, DMSO-$d_6$): d 1.17 (s, 3H), 1.19 (s, 3H), 2.92 (m, 1H), 4.88 (s, 2H), 5.20 (s, 2H), 5.89 (br s, 2H), 6.85 (d, 1H, J=9.0), 7.4 (m, 11H), 7.83 (d, 2H, J=7.5), 7.88 (d, 1H, J=8.1), 8.24 (s, 1H), 9.73 (s, 1H), 9.88 (s, 1H), 10.01 (s, 1H); MS(FD): 580.0.

Analysis for $C_{33}H_{32}N_4O_6 \cdot 0.35\ H_2O$: Calculated for: C, 67.53; H, 5.62; N, 9.55. Found: C, 68.13; H, 5.69; N, 9.49.

C) $N^1$-[3-(amino(imino)methyl)benzoyl]-$N^2$-(4-isopropylbenzoyl)-4-carboxymethoxy-1,2-benzenediamine dihydrochloride Using a procedure similar to Example 1G except starting with $N^1$-[3-(amino(hydroxyimino)methyl)benzoyl]-$N^2$-(4-isopropylbenzoyl)-4-(benzyloxy-carbonylmethoxy)-1,2-benzenediamine, the title compound was obtained as a solid (62%); NMR(300 MHz, $d_6$-DMSO): δ1.17 (s, 3H), 1.19 (s, 3H), 2.92 (m, 1H), 4.68 (s, 2H), 6.84 (d, 2H, J=9.0 Hz), 7.34 (d, 2H, J=8.4 Hz), 7.44 (d, 1H, J=8.7 Hz), 7.74 (t, 1H, J=7.8 Hz), 7.89 (d, 2H, J=7.8 Hz), 7.96 (d, 1H, J=8.4 Hz), 8.26 (d, 1H J=7.8 Hz), 8.42 (s, 1H), 9.15 (s, 2H), 9.45 (s, 2H), 10.01 (s, 1H), 10.36 (s, 1H); MS(FD): 474.

Analysis for $C_{26}H_{26}N_4O_5 \cdot 2\ HCl \cdot H_2O$: Calculated: C, 55.23; H, 5.35; N, 9.91. Found: C, 55.36; H, 5.07; N, 9.90.

EXAMPLE 3

Preparation of $N^1$-[3-(amino(imino)methyl)benzoyl]-$N^2$-(4-isopropylbenzoyl)-4-(ethoxycarbonylmethoxy)-1,2-benzenediamine hydrochloride

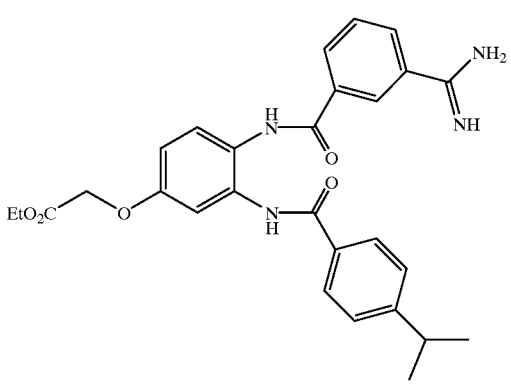

A) $N^1$-(3-cyanobenzoyl)-$N^2$-(4-isopropylbenzoyl)-4-(ethoxycarbonylmethoxy)-1,2-benzenediamine Using a procedure similar to Example 2A except starting with $N^1$-(3-cyanobenzoyl)-$N^2$-(4-isopropylbenzoyl)-4-hydroxy-1,2-benzenediamine and ethyl bromoacetate, the title compound was obtained as a solid (78%); IR($CHCl_3$): 2966, 1757, 1655, 1610, 1514 cm$^{-1}$; NMR(300 MHz, $CDCl_3$): δ1.31 (m, 9H), 3.00 (m, 1H), 4.24 (t, 2H, J=6.9 Hz), 4.35 (s, 2H), 6.59 (d, 1H, J=9.0 Hz), 6.95 (s, 1H), 7.35 (m, 3H), 7.64 (m, 1H), 7.82 (d, 1H, J=7.5 Hz), 7.92 (d, 2H, J=8.1 Hz), 8.23 (d, 1H, J=7.5 Hz), 8.32 (s, 1H), 9.06 (br s, 1H), 9.61 (br s, 1H); MS(FD): 485.2.

Analysis for $C_{28}H_{27}N_3O_5$: Calculated: C, 69.26; H, 5.60; N, 8.65. Found: C, 69.52; H, 5.71; N, 8.58.

B) $N^1$-[3-(amino(hydroxyimino)methyl)benzoyl]-$N^2$-(4-isopropylbenzoyl)-4-(ethoxycarbonylmethoxy)-1,2-benzenediamine.

Using a procedure similar to Example 1F except starting with $N^1$-(3-cyanobenzoyl)-$N^2$-(4-isopropylbenzoyl)-4-(ethoxycarbonylmethoxy)-1,2-benzenediamine (632 mg, 1.30 mmol), the title compound was obtained as a solid (60%); IR(KBr): 3345, 1753, 1647, 1521, 1178 cm$^{-1}$; NMR (300 MHz, DMSO-d): δ1.19 (m, 9H).2.89 (m, 1H), 4.17 (q, 2H, J=7.2 Hz), 4.78 (s, 2H), 5.88 (s, 2H), 6.83 (d, 1H, J=9.0 Hz), 7.49 –7.34 (m, 6H), 7.81 (d, 2H, J=8.1 Hz), 7.86 (d, 1H, J=12.9 Hz), 8.24 (s, 1H), 9.72 (s, 1H), 9.86 (s, 1H), 10.00 (s, 1H); MS(FD): 518.1.

Analysis for $C_{28}H_{30}N_4O_6$: Calculated: C, 64.85; H, 5.83; N, 10.80. Found: C, 64.59; H, 5.80; N, 10.59.

C) $N^1$-[3-(amino(imino)methyl)benzoyl]-$N^2$-(4-isopropylbenzoyl)-4-(ethoxycarbonylmethoxy)-1,2-benzenediamine hydrochloride Using a procedure similar to Example 1G except starting with $N^1$-[3-(amino(hydroxyimino)methyl)benzoyl]-$N^2$-(4-isopropylbenzoyl)-4-(ethoxycarbonylmethoxy)-1,2-benzenediamine, the title compound was obtained as a solid (65%); NMR(300 MHz, $d_6$-DMSO): 6 1.03 (t, 3H, J=7.1 Hz), 1.17 (s, 3H), 1.19 (s, 3H), 2.92 (m, 1H), 4.17 (q, 2H, J=6.9 Hz), 4.78 (s, 2H), 6.83 (d, 1H, J=9.0 Hz), 7.34 (d, 3H, J=7.8 Hz), 7.45 (d, 1H, J=8.7 Hz), 7.74 (t, 1H, J 7.8 Hz), 7.88 (d, 2H, J=7.8 Hz), 7.95 (d, 1H, J=8.4 Hz), 8.24 (d, 1H, J=7.8 Hz), 8.42 (s, 1H), 9.13 (s, 2H), 9.45 (s, 2H), 9.99 (s, 1H), 10.34 (s, 1H); MS(FD): 503.

Analysis for $C_{28}H_{30}N_4O_5 \cdot HCl \cdot H_2O$: Calculated: C, 60.38; H, 5.97; N, 10.06. Found: C, 60.64; H, 5.72; N, 9.97.

EXAMPLE 4

Preparation of $N^1$-[3-(amino(imino)methyl)benzoyl]-$N^2$-(4-t-butylbenzoyl)-1,2-benzenediamine hydrochloride

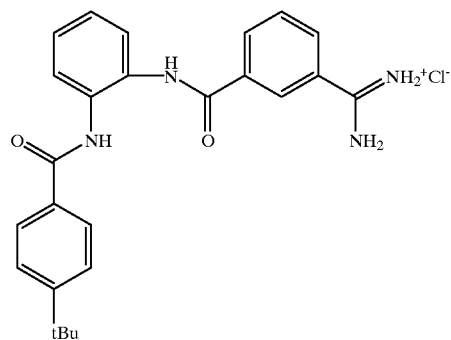

A) $N^1$-[3-cyanobenzoyl]-2-nitroaniline

Using a procedure similar to Example 1B except starting with 2-nitroaniline, the title compound was obtained as a yellow solid (98%), mp 154–155.5° C.; NMR (DMSO): δ7.47 (dt, 1H, J=9.0, 2.4 Hz), 7.69–7.83 (m, 3H), 8.03 (dd, 1H, J=9.9, 1.8 Hz), 8.13 (dt, J=9.3, 1.2 Hz), 8.25 (dt , 1H, J=9.9, 1.5 Hz), 8.39 (s, 1H), 10.92 (s, 1H).

Analysis for $C_{14}H_9N_3O$: Calculated: C, 62.92; H, 3.39; N, 15.72. Found: C, 62.86; H, 3.44; N, 16.02.

B) $N^1$-[3-cyanobenzoyl]-1,2-benzenediamine

Using a procedure similar to Example 1C except starting with $N^1$-[3-cyanobenzoyl]-2-nitroaniline, the title compound was obtained as a yellow solid (72%), mp 197–200° C.; NMR (DMSO): δ5.00 (s, 2H), 6.59 (t, 1H, J=9.3H), 6.79 (d, 1H, J=9.4 Hz), 6.98 (t, 1H, J=9.3 Hz), 7.17 (d, 1H, J=9.4 Hz), 7.73 (t, 1H, J=10.2 Hz), 8.05 (d, 1H, J=10.1 Hz), 8.27 (d, 1H, J=10.1 Hz), 8.44 (s, 1H), 9.81 (s, 1H); MS(FD): 237.

Analysis for $C_{14}H_{11}N_3O$: Calculated: C, 70.87; H, 4.67; N, 17.71. Found: C, 70.68; H, 4.58; N, 17.52.

C) $N^1$-[3-cyanobenzoyl]-$N^2$-(4-t-butylbenzoyl)-1,2-benzenediamine

Using a procedure similar to Example 1B except starting with $N^1$-[3-cyanobenzoyl]-1,2-benzenediamine and using triethylamine as base, the title compound was obtained as a white solid (730 mg, 87%); mp 174–174.5° C.; NMR (DMSO): δ1.27 (s, 9H), 7.27–7.32 (m, 2H), 7.53 (d, 2H, J=10.2 Hz), 7.61–7.64 (m, 1H), 7.86–7.72 (m, 1H), 7.75 (t, 1H, J=9.3 Hz), 7.88 (d, 2H, J=10.2 Hz), 8.06 (dd, 1H, J=7.8, 1.5 Hz), 8.23 (dd, 1H, J=9.6, 1.8 Hz), 8.36 (s, 1H), 9.90 (br s, 1H), 10.24 (br s, 1H); MS(FD+):

Analysis for $C_{25}H_{23}N_3O_2$: Calculated: C, 75.54; H, 5.83; N, 10.57. Found: C, 75.69; H, 6.14; N, 10.57.

D) $N^1$-[3-(amino(hydroxyimino)methyl)benzoyl]-$N^2$-(4-t-butylbenzoyl)-1,2-benzenediamine Using a procedure similar to Example 1F except starting $N^1$-[3-cyanobenzoyl]-$N^2$-(4-t-butylbenzoyl)-1,2-benzenediamine, the title compound was obtained as a white solid (55%), mp 201–204 ° C.; NMR(DMSO): δ1.30 (s, 9H), 5.91 (br s, 2H), 7.28–7.32 (m, 2H), 7.50–7.56 (m, 3H), 7.61–7.67 (m, 1H), 7.68–7.73 (m, 1H), 7.86–7.94 (m, 4H), 8.28 (s, 1H), 9.75 (s, 1H), 9.96 (s, 1H), 10.14 (s, 1H); MS(FD+):

Analysis for $C_{25}H_{26}N_4O_3$: Calculated: C, 69.75; H. 6.09; N 13.01. Found: C, 69.48; H, 5.91; N, 12.74.

E) $N^1$-[3-(amino(imino)methyl)benzoyl]-$N^2$-(4-t-butylbenzoyl)-1,2-benzenediamine hydrochloride Using a procedure similar to Example 1G except starting $N^1$-[3-(amino(hydroxyimino)methyl)benzoyl]-$N^2$-(4-t-butylbenzoyl)-1,2-benzenediamine, the title compound was obtained as a solid (76%); mp 196–198 ° C.; NMR (DMSO) δ1.32 (s, 9H), 7.28–7.32 (m, 2H), 7.52 (d, 2H, J=10.2 Hz), 7.62–7.67 (m, 1H), 7.67–7.71 (m, 1H), 7.77 (t, 1H, J=9.3 Hz), 7.96 (d, 2H, J=10.2 Hz), 8.00 (d, 1H, J=10.8 Hz), 8.30 (d, 1H, J=9.–3 Hz), 8.49 (s, 1H), 9.20 (s, 1H), 9.49 (s, 1H), 10.13 (s, 1H), 10.56 (s, 1H); MS(FD+): 415.

Analysis for $C_{25}H_{26}N_4O_2 \cdot HCl \cdot 0.75H_2O$: Calculated C, 64.03; H, 6.02; N, 11.95. Found: C, 64.71; H, 6.19; N, 12.16.

EXAMPLE 5

Preparation of $N^1,N^2$-bis[3-(aminoiminomethyl)benzoyl]-1,2-benzenediamine dihydrochloride A) $N^1,N^2$-bis(3-cyanobenzoyl)-1,2-benzenediamine Using a procedure similar to Example 1D, except starting with 1,2-benzenediamine and 3-cyanobenzoyl chloride with triethylamine as base, the title compound was obtained as an off-white solid (18%); IR(KBr): 3362, 2238, 1656, 1552 cm$^1$; NMR(300 MHz, DMSO-d$_6$): 7.33 (m,2H); 7.64 (m, 2H); 7.73 (t, 2H, J=9.5 Hz); 8.05 (d, 2H, J=9.3 Hz); 8.24 (d, 2H, J=9.9 Hz); 8.35 (s, 2H); 10.18 (br s, 2H); MS(FD): 366.1.

Analysis for $C_{22}H_{14}N_4O_2$: Calculated: C, 72.13; H, 3.85; N, 15.29. Found: C, 71.86; H, 3.96; N, 15.35.

B) $N^1,N^2$-bis[3-(amino(hydroxyiminomethyl))benzoyl]-1,2-benzenediamine

Using a procedure similar to Example 1F except starting with $N^1,N^2$-bis(3-cyanobenzoyl)-1,2-benzenediamine, the title compound was obtained as a white solid (92%); IR(KBr): 3324, 1658, 1514 cm$^1$; NMR(300 MHz, DMSO-d$_6$): 5.89 (br s, 4H); 7.31 (m, 2H); 7.52 (t, 2H, J=9.6 Hz); 7.68 (m, 2H); 7.85 (d, 2H, J=9.6 Hz); 7.93 (d, 2H, J=9.6 Hz); 8.27 (s, 2H); 9.74 (s, 2H); 10.08 (s, 2H); MS(FD): 432.1.

Analysis for $C_{22}H_{20}N_6O_4$: Calculated: C, 61.10; H, 4.66; N, 19.43. Found: C, 61.25; H, 4.81; N, 19.14.

C) $N^1,N^2$-bis[3-(aminoiminomethyl)benzoyl]-1,2-benzenediamine dihydrochloride Using a procedure similar to Example 1G except starting with $N^1,N^2$-bis[3-(amino(hydroxyimino)methyl)benzoyl]-1,2benzenediamine, the title compound was obtained as a tan solid (54%); IR(KBr): 1444, 1492, 1520, 1658 cm$^{-1}$; NMR (300 MHz, DMSO-d$_6$): 7.34 (m, 2H); 7.75 (m, 3H); 8.01 (d, 2H, J=9.0 Hz); 8.35 (d, 2H, J=8.7 Hz); 8.57 (s, 4H); 9.27 (s, 4H); 9.51 (s, 4H); 10.64 (s, 2H); MS(FD): 400.

Analysis for $C_{22}H_{26}N_6O_2 \cdot 2HCl$: Calculated: C, 55.82; H, 4.68; N, 17.75. Found: C, 48.36; H, 4.69; N, 14.98.

EXAMPLE 6

Preparation of $N^1$-[3-(amino(imino)methyl)benzoyl]-$N^2$-(4-isopropylbenzoyl)-4-(carboxymethyl)-1,2-benzenediamine hydrochloride A) N-(3-cyanobenzoyl)-4-(ethoxycarbonylmethyl)-2-nitroaniline Using a procedure similar to Example 1B except starting with 4-(ethoxycarbonylmethyl)-2-nitroaniline, the title compound was obtained as a solid (98%); IR(CHCl$_3$): 1340, 1516, 1694, 1733 cm$^{-1}$; NMR(300 MHz, CDCl$_3$): 1.28 (t, 3H, J=7.2 Hz); 3.70(s, 2H); 4.19 (q, 2H, J=7.2 Hz); 7.69 (m, 2H); 7.89 (d, 1H, J=8.1 Hz); 8.18 (d, 1H, J=7.8 Hz); 8.24 (s, 1H); 8.30(s, 1H); 8.92 (d, 1H, J=9.3 Hz); MS(FD): 353.

Analysis for $C_{18}H_{15}N_3O_5$: Calculated: C, 61.19; H, 4.33; N, 11.80. Found: C, 61.28; H, 4.35; N, 11.79.

B) $N^1$-(3-cyanobenzoyl)-4-(ethoxycarbonylmethyl)-1,2-benzenediamine

Using a procedure similar to Example 1C except starting with N-(3-cyanobenzoyl)-4-(ethoxycarbonylmethyl)-2-nitroaniline, the title compound was obtained as a solid (78%); IR(CHCl$_3$): 1519, 1673, 1728, 2235, 3025 cm$^{-1}$; NMR(300 MHz, DMSO-d$_6$): 1.19 (t, 3H, J=8.4 Hz); 3.50(s, 2H); 4.08 (q, 2H, J=8.4 Hz); 5.04 (s, 2H); 6.47 (d, 1H, J=9.6 Hz); 6.67 (s, 1H); 7.08 (d, 1H, J=9.6 Hz); 7.73 (t, 1H, J=9.6 Hz); 8.04 (d, 1H, J=9.6 Hz); 8.26 (d, 1H, J=9.9 Hz); 8.44 (s, 1H); 9.77 (s, 1H); MS(FD): 323.0.

Analysis for $C_{18}H_{17}N_3O_3$: Calculated: C, 66.86; H, 5.30; N, 13.00. Found: C, 68.87; H, 5.70; N, 12.75.

C) $N^1$-(3-cyanobenzoyl)-$N^2$-(4-isopropylbenzoyl)-4-(ethoxycarbonylmethyl)-1,2-benzenediamine Using a procedure similar to Example 1D except starting with N-(3-cyanobenzoyl)-4-(ethoxycarbonylmethyl)-1,2-benzenediamine, the title compound was obtained as a solid (88%); IR(CHCl$_3$): 1308, 1524, 1654, 1729, 2966 cm$^{-1}$; NMR(300 MHz, DMSO-d$_6$): 1.21 (m, 9H); 2.92 (m, 1H); 3.72 (s, 2H); 4.12 (q, 2H, J=6.9 Hz); 7.19 (d, 1H, J=8.4 Hz); 7.39 (d, 2H, J=8.4 Hz); 7.58 (d, 1H, J=8.4 Hz); 7.64 (s, 1H); 7.75 (t, 1H, J=7.5 Hz); 7.89 (d, 2H, J=8.4 Hz); 8.07 (d, 1H, J=8.1 Hz); 8.24 (d, 1H, J=7.8 Hz); 8.36 (s, 1H); MS(FD): 469.

Analysis for $C_{28}H_{27}N_3O_4$: Calculated: C, 71.63; H, 5.80; N, 8.95. Found: C, 71.69; H, 6.02; N, 8.75.

D) $N^1$-(3-cyanobenzoyl)-$N^2$-(4-isopropylbenzoyl)-4-(carboxymethyl)-1,2-benzenediamine To a mixture of $N^1$-(3-cyanobenzoyl)-$N^2$-(4-isopropylbenzoyl)-4-(ethoxycarbonyl-methyl)-1,2-benzenediamine (1.41 g, 3.00 mmol) in THF (30 mL) and MeOH (10 mL) was added 1 M LiOH (10 mL) and stirred for 2.5 h. The reaction was diluted with Et$_2$O (300 mL) and washed with 1N HCl (40 mL) and H$_{20}$ (40 mL). The organic layer was concentrated to give the title compound as a pale yellow solid (1.32 g, quant.); IR(KBr): 1326, 1515, 1625, 1672, 3326 cm$^{-1}$; NMR(300 MHz, DMSO-d$_6$): 1.19 (d, 6H, J=6.9 Hz); 2.97 (m, 1H); 3.65 (s, 2H); 7.12 (d, 1H, J=8.1 Hz); 7.35 (d, 2H, J=7.8 Hz); 7.49 (d, 1H, J=8.1 Hz); 7.54 (s, 1H); 7.71 (t, 1H, J=8.0 Hz); 7.86 (d, 2H, J=7.8 Hz); 8.02 (d, 1H, J=7.2 Hz); 8.22 (d, 1H, J=8.4 Hz); 8.34 (s, 1H); 9.96 (s, 1H); 10.27 (s, 1H); MS(FD): 441.0.

Analysis for $C_{26}H_{23}N_3O_4 \cdot 1.5 \, H_2O$: Calculated: C, 67.30; H, 5.54; N, 9.06. Found: C, 67.31; H, 5.20; N, 8.92.

E) $N^1$-[3-(amino(hydroxyimino)methyl)benzoyl]-$N^2$-(4-isopropylbenzoyl)-4-(carboxymethyl)-1,2-benzenediamine Using a procedure similar to Example 1F except starting with $N^1$-(3-cyanobenzoyl)-$N^2$-(4-isopropylbenzoyl)-4-(carboxymethyl)-1,2-benzenediamine, the title compound was obtained as a solid (21%); NMR(300 MHz, DMSO-d$_6$): 1.17 (m, 9H); 2.95 (m, 1H); 3.69 (s, 2H); 4.08 (q, 2H, J=7.2 Hz); 5.89 (s, 2H); 7.17 (d, 1H, J=8.4 Hz); 7.36 (d, 2H, J=8.1 Hz); 7.53 (m, 3H); 7.83 (m, 4H); 8.24 (s, 1H); 9.73 (s, 1H); 9.94 (s, 1H); 10.07(s, 1H); MS(FD): 502.

Analysis for $C_{28}H_{30}N_4O_5$: Calculated: C, 66.92; H, 6.02; N, 11.15. Found: C, 64.70; H, 5.74; N, 10.25.

F) $N^1$-[3-(amino(imino)methyl)benzoyl]-$N^2$-(4-isopropylbenzoyl)-4-(carboxymethyl)-1,2-benzenediamine hydrochloride Using a procedure similar to Example 1G except starting with $N^1$-[3-(amino(hydroxy-imino)methyl)benzoyl]-$N^2$-(4-isopropylbenzoyl)-4-(carboxymethyl)-1,2-benzenediamine, the title compound was obtained as a pale yellow solid (81%); NMR(300 MHz, DMSO-d$_6$): 1.16 (m, 9H); 2.91 (m, 1H); 3.68 (s, 2H); 4.07 (q, 2H, J=7.2 Hz); 7.15 (d, 1H, J=8.1 Hz); 7.33 (d, 2H, J=8.4 Hz); 7.57 (m, 3H); 7.73 (t, 1H, J=7.8 Hz); 7.91 (d, 2H, J=7.8 Hz); 7.96 (d, 1H, J=8.1 Hz); 8.26 (d, 1H, J=7.5 Hz); 8.45 (s, 1H); 9.19 (s, 2H); 9.47 (s, 2H); 10.10 (s, 1H); 10.52 (s, 1H); MS(FD): 487.0.

Analysis for $C_{28}H_{30}N_4O_4 \cdot 1.5 \, HCl \cdot 0.25 \, H_2O$: Calculated: C, 61.62; H, 5.91; N, 10.27. Found: C, 61.47; H. 5.58; N, 10.37.

EXAMPLE 7

Preparation of $N^1$-[3-(amino(imino)methyl)benzoyl]-$N^2$-(4-isopropylbenzoyl)-1,2-benzenediamine hydrochloride A) $N^1$-(t-butoxycarbonyl)-1,2-benzenediamine To a mixture of BOC$_2$O (24.3 g, 111.2 mmol), 1:1 THF:H$_2$O (500 mL) and potassium carbonate was added phenylene diamine (10 g, 92.5 mmol) and stirred for 24 h. The reaction was concentrated and extracted with EtOAc. The organic layer was MgSO$_4$ dried and concentrated. The residue was chromatographed (10% EtOAc/hexanes to 40% EtOAc/hexanes) to give the title compound as a solid (14.56 g, 76%).

B) $N^1$-(t-butoxycarbonyl)-$N^2$-(4-isopropylbenzoyl)-1,2-benzenediamine

Using a procedure similar to ID except starting with $N^1$-(t-butoxycarbonyl)-1,2-benzenediamine, the title compound was obtained as a solid (85%); NMR(300 MHz, DMSO-d6): 1.24 ((d, 6H, J=8.4 Hz), 1.44 (s, 9H), 2.98 (m, 1H), 7.17 (m,2H), 7.41 (d, 2H, J=9.9 Hz), 7.54 (d, 2H, J=9.0 Hz), 7.89 (d, 2H, J=9.6 Hz), 8.65 (s, 1H), 9.77 (s, 1H); MS(FD$^+$): 354.2

Analysis for $C_{21}H_{26}N_2O_3$: Calculated: C, 71.16; H, 7.39 N, 7.90. Found: C, 72.17; H, 7.53; N, 8.17.

C) $N^1$-(4-isopropylbenzoyl)-1,2-benzenediamine

Using a procedure similar to 8K except starting with $N^1$-(t-butoxycarbonyl)-1,2-benzenediamine, the title compound was obtained as a solid (70%); NMR(300 MHz, CDCl$_3$): 1.29 (d, 6H, J=8.4 Hz), 2.99 (m, 1H), 6.81–6.87 (m, 2H), 7.10 (d, 1H, J=9.3 Hz), 7.34 (m, 3H), 7.84 (d, 2H, J=9.9 Hz); MS(FD$^+$): 254.

Analysis for $C_{16}H_{18}N_2O$: Calculated: C, 75.56; H, 7.13; N, 11.01. Found: C, 75.81; H, 6.86; N, 10.75.

D) $N^1$-(3-cyanobenzoyl)-$N^2$-(4-isopropylbenzoyl)-1,2-benzenediamine

Using a procedure similar to 1B except starting with $N^1$-(4-isopropylbenzoyl)-1,2-benzenediamine, the title compound was obtained as a solid (53%); NMR(300 MHz, CDCl$_3$): 1.30 (d, 6H, J=8.4 Hz), 3.00 (m, 1H), 7.04 ((m, 2H), 7.34 (d, 1H, J=8.4 Hz), 7.38 (d, 1H, J=9.9 Hz), 7.55 (d, 1H, J=8.4 Hz), 7.62 (d, 1H, J=9.3 Hz), 7.83 (d, 1H, J=9.3 Hz), 7.91 (d, 2H, J=9.9 Hz), 8.23 (d, 1H, J=9.6 Hz), 8.31 (d, 2H, J=9.0 Hz), 8.83 (s, 1H), 9.78 (s, 1H); MS(FD+):383.3.

Analysis for $C_{24}H_{21}N_3O_{2-0.25} H_2O$: Calculated: C, 74.30; H, 5.59 N, 10.83. Found: C, 74.16; H, 5.55; N, 10.79.

E) $N^1$-[3-(amino(hydroxyimino)methyl)benzoyl]-$N^2$-(4-isopropylbenzoyl)-1,2-benzenediamine Using a procedure similar to 1F except starting with $N^1$-(3-cyanobenzoyl)-$N^2$-(4-isopropylbenzoyl)-1,2-benzenediamine, the title compound was obtained as a solid (40%);

Analysis for $C_{24}H_{21}N_3O_2 \cdot 0.25 \, H_2O$: Calculated: C, 74.30; H, 5.59; N, 10.83. Found: C, 74.16; H, 5.55; N, 10.79.

F) $N^1$-[3-(amino(imino)methyl)benzoyl]-$N^2$-(4-isopropylbenzoyl)-1,2-benzenediamine hydrochloride Using a procedure similar to Example 1G except starting with $N^1$-[3-(amino(hydroxyimino)methyl)benzoyl]-$N^2$-(4-isopropylbenzoyl)-1,2-benzenediamine, the title compound was obtained as a solid (63%); mp 227–9.0; MS(FD): 401.1.

Analysis for $C_{24}H_{25}N_4O_2 \cdot HCl \cdot 1.5 \, H_2O$: Calculated: C, 62.13; H, 6.08; N, 12.08. Found: C, 61.90; H, 5.72; N, 11.91.

EXAMPLE 8

Preparation of $N^1$-[(l-iminoisoindolin-6-yl)carbonyl]-$N^2$-(t-butylbenzoyl)-4-(ethoxycarbonylmethoxy)-1,2-benzenediamine trifluoroacetate A) methyl 3-bromo-4-methylbenzoate To a mixture of hexane washed 60% disp. NaH (2.28 g, 57 mmol) in DMF (250 mL), 0° C., was added 3-bromo-4-methylbenzoic acid (10.03 g, 46.6 mmol). After 30 min, the reaction was warmed to room temperature, diluted with EtOAc (1.25 L) and washed with H$_2$O (5×250 mL). The organic layer was MgSO$_4$ dried and concentrated. The residue was chromatographed (~375 g silica, 10% EtOAc/CH$_2$Cl$_2$) to give the desired product as a solid (16.68 g, 63%); IR(CHCl$_3$): 1260, 1294, 1437, 1721 cm$^{-1}$; NMR(300 MHz, CDCl$_3$): 2.46 (s, 3H); 3.92 (s, 3H); 7.31 (d, 1H, J=7.8 Hz); 7.88 (d, 1H, J=7.8 Hz); 8.21 (s, 1H); MS(FD): 228.0.

Analysis for $C_9H_9BrO_2$: Calculated: C, 47.19; H, 3.96. Found: C, 47.06; H, 3.92.

B) methyl 3-cyano-4-methylbenzoate

A mixture of copper (I) cyanide (510 mg, 5.69 mmol) and DMF (16 mL) was heated to 140 ° C. The reaction was added methyl 3-bromo-4-methylbenzoate (505 mg, 2.2 mmol) in DMF (10 mL) and heating was continued for 12 h. The reaction was cooled, diluted with EtOAc (125 mL) and washed with H$_2$O (5×25 mL). The EtOAc layer was dried over MgSO$_4$ and concentrated. The residue was chromatographed (40 g silica, 10% EtOAc/hexanes) to give the title compound as a solid (236 mg, 61%); IR(CHCl$_3$): 1128, 1269, 1300, 1725, 2231, 3024 cm$^{-1}$; NMR(300 MHz, CDCl$_3$): 2.63 (s, 3H); 3.95 (s, 3H); 7.43 (d, 1H, J=8.1 Hz); 8.14 (d, 1H, J=8.1 Hz); 8.28 (s, 1H); MS(FD): 175.1.

Analysis for $C_{10}H_9N_1O_2$: Calculated: C, 68.56; H, 5.18; N, 8.00. Found: C, 68.29; H, 5.18; N, 8.04.

C) methyl 3-cyano-4-(bromomethyl)benzoate

A mixture of methyl 3-cyano-4-methylbenzoate (1.78 g, 9.79 mmol) and NBS (1.92 g, 10.8 mmol) in $CCl_4$ (150 mL) was irradiated with a 150W tungsten lamp at 50° C. for 2 h. The reaction was cooled, filtered, and concentrated. The residue was chromatographed (250 g silica, 10% EtOAc/hexanes to 15% EtOAc/hexanes) to give the title compound (1.20 g, 48%); IR($CHCl_3$): 1291, 1302, 1439, 1728 $cm^{-1}$; NMR(300 MHz, CDCl3): 4.01 (s, 3H); 4.67 (s, 3H); 7.66 (d, 1H, J=8.1 Hz); 8.24 (d, 1H, J=8.7 Hz); 8.34 (s, 1H); MS(FD): 253.0.

Analysis for $C_{10}H_8NO_2$: Calculated: C, 47.27; H, 3.17; N, 5.51. Found: C, 47.45; H, 3.38; N, 5.53.

D) methyl 3-cyano-4-[(N,N-bis(t-butoxycarbonyl)amino) methyl]benzoate

To a mixture of hexane washed 60% disp. NaH (40 mg, 1 mmol) and DMF (8 mL) was added HN(BOC)2 (203 mg, 0.93 mmol) and stirred for 30 m. The reaction was added methyl 3-cyano-4-(bromomethyl)benzoate (202 mg, 0.80 mmol). After 3.5 h, the reaction was diluted with EtOAc (40 mL) and washed with $H_2O$ (6×5 mL). The organic layer was $MgSO_4$ dried and concentrated. The crude material was chromatographed (30 g silica, 10% EtOAc/hexanes) to give the title compound (quant.). IR($CHCl_3$): 1125, 1370, 1723, 1791, 3020 $cm^{-1}$; NMR(300 MHz, $CDCl_3$): 1.46 (s, 18H); 3.96 (s, 3H); 5.08 (s, 2H); 7.42 (d, 1H, J=8.4 Hz); 8.23 (d, 1H, J=8.4 Hz); 8.32 (s, 1H); MS(FD): 391.

Analysis for $C_{20}H_{26}N_2O_6$: Calculated: C, 61.53; H, 6.71; N, 7.17. Found: C, 61.26; H, 6.99; N, 7.13.

E) 3-cyano-4-(N,N-bis(t-butoxycarbonyl)aminomethyl) benzoic acid

To a −25° C. solution of methyl 3-cyano-4-(N,N-bis-(t-butoxycarbonyl)aminomethyl)benzoate (1.81 g, 4.64 mmol) in THF (14 mL) was added a 1:1 mixture of MeOH (4.6 mL) and 1 M LiOH (4.6 mL). After 1.25 h, the reaction was quenched with 1 N HCl (4.6 mL), diluted with Et2O (150 mL) and washed with $H_2O$ (2×30 mL). The combined aqueous layers was extracted with EtOAc (150 mL). The combined organic layers was $MgSO_4$ dried, filtered, and concentrated. The crude material was chromatographed (0.5% HOAc in 30% EtOAc/hexanes to 0.5% HOAc in 40% EtOAc/hexanes) to give the title compound (767 mg, 44%); IR($CHCl_3$): 1146, 1370, 1704, 2984, 3020 $cm^{-1}$; NMR(300 MHz, DMSO-$d_6$): 1.36 (s, 18H); 4.93 (s, 2H); 7.41 (d, 1H, J=8.4 Hz); 8.21 (d, 1H, J=8.4 Hz); 8.25 (s, 1H); MS(FD): 377.0.

Analysis for $C_{19}H_{24}N_2O_6$: Calculated: C, 60.63; H, 6.43; N, 7.44. Found: C, 60 39; H, 6.30; N, 7.36.

F) N-(t-butoxycarbonyl)-2-nitro-4-(dimethyl-t-butylsiloxy) aniline

To a mixture 2-nitro-4-(dimethyl-t-butylsiloxy)aniline (10.00 g, 37.3 mmol) in THF (85 mL) was added a solution of 1M NaHMDS/THF (75 mL, 75 mmol). After 15 minutes, a solution of di-t-butyl dicarbonate (7.33 mg, 33.6 mmol) in THF (120 mL) was added and stirred for 30 m. The reaction was concentrated, diluted with EtOAc (350 mL) and washed with 0.1N HCl (850 mL). The aqueous layer was added sat. aq. $NaHCO_3$ (85mL) and extracted with EtOAc (2×350 mL). The combined EtOAc layers was $MgSO_4$ dried, filtered, and concentrated. The crude material chromatographed(hexanes to 5% EtOAc/ hexanes) the title compound (7.99 g, 21.7 mmol, 58%). This material was used without further purification.

G) $N^1$-(t-butoxycarbonyl)-4-(dimethyl-t-butylsiloxy)-1,2-benzenediamine

Using a procedure similar to Example 1C except starting with N-(t-butoxycarbonyl)-2-nitro-4-(dimethyl-t-butylsiloxy)aniline, the title compound was obtained (48%); IR($CHCl_3$): 866, 1160, 1515, 1709, 2958 $cm^{-1}$; NMR(300 MHz, CDCl3): 0.15 (s, 6H); 0.95 (s, 9H); 1.51 (s, 9H); 6.02 (br s, 2H); 6.24 (d, 1H, J=8.3 Hz); 6.27 (s, 1H); 6.99 (d, 1H, J=8.3 Hz); MS(FD): 338.3.

Analysis for $C_{17}H_{30}N_2O_3$: Calculated: C, 60.32; H, 8.93; N, 8.28. Found: C, 60.16; H, 9.01; N, 8.26.

H) $N^1$-(t-butoxycarbonyl)-$N^2$-(t-butylbenzoyl)-4-(dimethyl-t-butylsiloxy)-1,2-benzenediamine Using a procedure similar to Example 1B except starting with $N^1$-(t-butoxycarbonyl)-4-(dimethyl-t-butylsiloxy)-1,2-benzenediamine and 4-t-butylbenzoyl chloride, the title compound was obtained (97%); IR($CHCl_3$): 858, 1271, 1514, 1668, 2962 $cm^{-1}$; NMR(300 MHz, $CDCl_3$): 0.22 (s, 6H); 0.98 (s, 9H); 1.35 (s, 9H); 1.55 (s,9H); 6.46 (s, 1H); 6.64 (d, 1H, J=8.7 Hz); 7.06 (d, 1H, J=8.4 Hz); 7.47 (d, 2H, J=8.1 Hz); 7.88 (d, 2H, J=8.7 Hz); 8.93 (br s, 1H); MS(FD): 498.3.

Analysis for $C_{28}H_{42}N_2O_4Si$: Calculated: C, 67.43; H, 8.49; N, 5.62. Found: C, 68.65; H, 8.82; N, 5.61.

I) $N^1$-(t-butoxycarbonyl)-$N^2$-(t-butylbenzoyl)-4-hydroxy-1,2-benzenediamine

Using a procedure similar to Example 1E except starting with $N^1$-(t-butoxy-carbonyl)-$N^2$-(t-butylbenzoyl)-4-(dimethyl-t-butylsiloxy)-1,2-benzenediamine, the title compound was obtained (97%); IR(KBr): 1168, 1285, 1536, 1631, 1690, 2965 $cm^{-1}$; NMR(300 MHz, $CDCl_3$): 1.36 (s, 9H); 1.53 (s,9H); 6.38 (s, 1H); 6.66 (d, 1H, J=8.4 Hz); 7.01 (d, 1H, J=8.4 Hz); 7.49 (d, 2H, J=8.4 Hz); 7.70 (s, 1H); 7.89 (d, 2H, J=8.4 Hz); MS(FD): 384.2.

Analysis for $C_{22}H_{28}N_2O_4 \cdot 0.25\ H_2O$: Calculated: C, 67.93; H, 7.39; N, 7.20. Found: C, 67.90; H, 7.37; N, 6.85.

J) $N^1$-(4-t-butoxycarbonyl)-$N^2$-(t-butylbenzoyl)-4-(ethoxycarbonylmethoxy)-1,2-benzenediamine Using a procedure similar to Example 2A except starting with $N^1$-(4-t-butoxycarbonyl)-$N^2$-(t-butylbenzoyl)-4-hydroxy-1,2-benzenediamine and ethyl bromoacetate, the title compound was obtained (76%); IR($CHCl_3$): 1159, 1529, 1705, 1755, 2968 $cm^{-1}$; NMR(300 MHz, $CDCl_3$): 1.31 (t, 3H, J=6.9 Hz); 1.36 ( s, 9H); 1.52 (s, 9H); 4.28 (q, 2H, J=6.9 Hz); 4.63 (s, 2H); 6.56 (s, 1H); 6.77 (d, 1H, J=8.7 Hz); 7.13 (d, 1H, J=8.7 Hz); 7.49 (d, 2H, J=8.4 Hz); 7.56 (s, 1H); 7.89 (d, 2H, J=8.1 Hz); 9.09 (br s, 1H); MS(FD): 470.

Analysis for $C_{26}H_{34}N_2O_6$: Calculated: C, 66.36; H, 7.28; N, 5.95. Found: C, 68.08; H, 7.84; N, 5.54.

K) $N^2$-(t-butylbenzoyl)-4-(ethoxycarbonylmethoxy)-1,2-benzenediamine

To a mixture of $N^1$-(t-butoxycarbonyl)-$N^2$-(t-butylbenzoyl)-4-(ethoxycarbonylmethoxy)-1,2-benzenediamine (878 mg, 1.87 mmol) and $CH_2C_{12}$ (20 mL) was added TFA (1.5 mL, 19.5 mmol). After 12 h, the reaction was diluted with $CH_2Cl_2$ (300 ml) and washed with sat. aq. $NaHCO_3$ (3×50 mL). The organic layer was $MgSO_4$ dried, and concentrated. The crude material was chromatographed (65 g silica, 20% EtOAc/hexanes to 50% EtOAc/hexanes) to give the title compound (98%); IR($CHCl_3$): 1176, 1512, 1668, 1755, 2968 $cm^{-1}$; NMR(300 MHz, DMSO-$d_6$): 1.22 (t, 3H, J=7.2 Hz); 1.33 (s, 9H); 4.17 (q, 2H, J=7.2 Hz); 4.62 (s, 2H); 6.64 (d, 1H, J=8.7 Hz); 6.74 (d, 1H, J=8.7 Hz); 6.95 (d, 1H, J=3.0 Hz); 7.54 (d, 2H, J=8.7 Hz); 7.91 (d, 2H, J=8.1 Hz); 9.59 (s, 1H); MS(FD): 370.

Analysis for $C_{21}H_{36}N_2O_4$: Calculated: C, 68.09; H, 7.07; N, 7.56. Found: C, 68.34; H, 7.25; N, 7.56.

L) $N^1$-[4-(N,N-(bis-t-butoxycarbonyl)aminomethyl)-3-cyanobenzoyl]-$N^2$-(t-butylbenzoyl)-4-(ethoxycarbonylmethoxy)-1,2-benzenediamine To a mixture of 4-(N,N-(bis-(t-butoxycarbonyl) aminomethyl)-3-cyanobenzoic acid (184 mg, 0.49 mmol)

and $CH_2Cl_2$ (5 mL) was added, in sequence, pyridine (44 mL, 0.54 mmol), DMF (3 drops) and oxalyl chloride (48 mL, 0.55 mmol). After 1 h, the reaction was concentrated and the residue was diluted with $CH_2Cl_2$ (2 mL). Pyridine was added, followed by the $N^2$-(t-butylbenzoyl)-4-(ethoxycarbonylmethoxy)-1,2-benzenediamine (167 mg, 0.45 mmol) in $CH_2Cl_2$ (3 mL). After 1 h, the reaction was diluted with $CH_2Cl_2$ (75 mL) and washed with sat. aq. $NH_4Cl$ (2×5 mL). The organic layer was $MgSO_4$ dried, filtered, and concentrated. The residue chromatographed (30% EtOAc/hexanes) to give the title compound (140 mg, 0.19 mmol, 39%);

NMR(300 MHz, $CDCl_3$): 1.27 (t, 3H, J=6.6 Hz); 1.37 (s, 9H); 1.46 (s, 18H); 4.25 (q, 2H, J=7.2 Hz); 4.45 (s, 2H); 5.09 (s, 2H); 6.69 (d, 1H, J=9.0 Hz); 6.97 (s, 1H); 7.46 (m, 2H); 7.54 (d, 2H, J=8.7 Hz); 7.91 (d, 2H, J=8.4 Hz); 8.15 (d, 1H, J=8.7 Hz): 8.30 (s, 1H); 8.89 (s, 1H); 9.48 (s, 1H); MS(FD): 728.6.

Analysis for $C_{40}H_{48}N_4O_9$: Calculated: C, 65.92; H, 6.64; N, 7.69. Found: C, 66.33; H, 7.03; N, 7.39.

M) $N^1$-[(1-iminoisoindolin-6-yl)carbonyl]-$N^2$-(t-butylbenzoyl)-4-(ethoxycarbonylmethoxy)-1,2-benzenediamine trifluoroacetate To a mixture of $N^1$-[4-(N,N-(bis-t-butoxycarbonyl)aminomethyl)-3-cyanobenzoyl]-$N^2$-(t-butylbenzoyl)-4-(ethoxycarbonylmethoxy)-1,2-benzenediamine (109 mg, 0.15 mmol) in $CH_2Cl_2$ (5ml) was added TFA (0.15 mL, 1.95 mmol). After 1.5 h, more TFA (60 mL, 0.78 mmol) followed by TFA (1 mL, 12.98 mmol) were added. After 15 minutes, the reaction was concentrated and the residue was dissolved in EtOH (5 mL). $Et_3N$ (42 mL, 0.30 mmol) was added. The solution was heated to reflux for 30 min. The reaction was cooled and concentrated. The residue was chromatographed with a polystyrene support (HP-20) column using $H_2O$ as the eluant to give the title compound (29 mg, 0.045 mmol, 30%); NMR(300 MHz, DMSO-$d_6$): 1.30 (m, 12H); 4.29 (q, 2H, J=7.2 Hz); 4.65 (s, 2H): 4.67 (s, 2H); 6.97 (m, 2H); 7.45 (d, 2H, J=8.4 Hz); 7.52 (d, 1H, J=8.7 Hz); 7.65 (d, 1H, J=8.1 Hz); 8.00 (d, 2H, J=8.1 Hz); 8.23 (d, 1H, J=7.8 Hz); 8.49 (s, 1H); 9.48 (s, 2H); 9.62 (s, 1H); 10.07 (s, 1H); 10.20 (s, 1H); MS(FD): 529.3.

EXAMPLE 9

Preparation of $N^1$-[(1-iminoisoindolin-6-yl)carbonyl]-$N^2$-(t-butylbenzoyl)-4-(benzyloxy)-1,2-benzenediamine trifluoroacetate A) $N^1$-(4-t-butoxycarbonyl)-$N^2$-(t-butylbenzoyl)-4-benzyloxy-1,2-benzenediamine Using a procedure similar to Example 2A except starting with $N^1$-(4-t-butoxycarbonyl)-$N^2$-(t-butylbenzoyl)-4-hydroxy-1,2-benzenediamine and benzyl bromide, the title compound was obtained (65%); IR($CHCl_3$: 1159, 1529, 1668, 1700 $cm^{-1}$;

NMR(300 MHz, DMSO-$d_6$): 1.33 (s, 9H); 1.44 (s, 9H); 5.10 (s, 2H); 6.87 (d, 1H, J=8.7 Hz); 7.41 (m, 7H); 7.57 (d, 2H, J=8.4 Hz); 7.87 (d, 2H, J=8.4 Hz); 8.51 (br s, 1H); 9.77 (s, 1H); MS(FD): 474.

Analysis for $C_{29}H_{34}N_2O_4$: Calculated: C, 73.39; H, 7.22; N, 5.90. Found: C, 74.29; H, 7.92; N, 5.48.

B) $N^2$-(t-butylbenzoyl)-4-benzyloxy-1,2-benzenediamine

Using a procedure similar to Example 8K except starting with $N^1$-(4-t-butoxycarbonyl)-$N^2$-(t-butylbenzoyl)-4-benzyloxy-1,2-benzenediamine, the title compound was obtained (72%); IR($CHCl_3$): 1270, 1511, 1609, 1667, 2967 $cm^{-1}$;

NMR(300 MHz, DMSO-$d_6$): 1.33 (s, 9H); 4.99 (s, 2H); 6.74 (m, 3H); 7.03 (s, 1H); 7.39 (m, 6H); 7.54 (d, 2H, J=8.4 Hz); 7.92 (d, 2H, J=8.7 Hz); 9.59 (s, 1H); MS(FD): 374.1

Analysis for $C_{24}H_{26}N_2O_2$: Calculated: C, 76.98; H, 7.00; N, 7.48. Found: C, 77.02; H, 6.76; N, 7.27.

C) $N^1$-[4-(N,N-(bis-t-butoxycarbonyl)aminomethyl)-3-cyanobenzoyl]-$N^2$-(t-butylbenzoyl)-4-(benzyloxy)-1,2-benzenediamine Using a procedure similar to Example 8L except starting with $N^2$-(t-butylbenzoyl)-4-benzyloxy-1,2-benzenediamine, the title compound was obtained (81%).

NMR(300 MHz, $CDCl_3$): 1.33 (s, 9H); 1.46 (s, 18H); 4.89 (s, 2H); 5.07 (s, 2H); 6.75 (d, 1H, J=9.0 Hz); 7.03 (s, 1H); 7.40 (m, 6H); 7.55 (d, 2H, J=8.4 Hz); 7.92 (d, 2H, J=8.4 Hz); 8.14 (d, 1H, J=8.4 Hz); 8.28 (s, 1H); 8.82 (s, 1H); 9.39 (s, 1H); MS(FD): 732.3.

Analysis for $C_{43}H_{48}N_4O_7$: Calculated: C, 70.47; H, 6.60; N, 7.65. Found: C, 70.52; H, 6.64; N, 7.70.

D) $N^1$-[(1-iminoisoindolin-6-yl)carbonyl]-$N^2$-(4-t-butylbenzoyl)-4-benzyloxy-1,2-benzenediamine trifluoroacetate To a mixture of $N^1$-[4-(N,N-(bis-t-butoxycarbonyl)aminomethyl)-3-cyanobenzoyl]-$N^2$-(t-butylbenzoyl)-4-benzyloxy-1,2-benzenediamine (176 mg, 0.24 mmol) and $CH_2Cl_2$ (5 mL) was added TFA (1 mL, 12.98 mmol). After 1 h, the reaction was concentrated and the residue was dissolved in EtOH (5 mL) and heated to reflux. After 1 h, the reaction was cooled and concentrated to give the title compound as a tan solid (156 mg, 0.24 mmol, 100%); IR(KBr): 1202, 1462, 1500, 1664, 1696$cm^{-1}$; NMR(300 MHz, DMSO-$d_6$): 1.26 (s, 9H); 4.85 (s, 2H); 5.12 (s, 2H); 6.96 (d, 1H, J=8.7 Hz); 7.42 (m, 9H); 7.82 (d, 2H, J=8.4 Hz); 7.87 (d, 1H, J=8.1 Hz); 8.30 (d, 1H, J=8.1 Hz); 9.37 (s, 2H); 9.75 (s, 1H); 9.89 (s, 1H); 10.13 (s, 1H); MS(FD): 533.3.

Analysis for $C_{33}H_{32}N_4O_3 \cdot CF_3COOH \cdot 0.25\ H_2O$: Calculated: C, 64.56; H, 5.19; N, 8.60. Found: C, 64.28; H, 5.58; N, 7.60.

EXAMPLE 10

Preparation of $N^1$-[(1-iminoisoindolin-6-yl)carbonyl]-$N^2$-(t-butylbenzoyl)-4-(hydroxy)-1,2-benzenediamine trifluoroacetate A) $N^1$-[4-(N,N-(bis-t-butoxycarbonyl)aminomethyl)-3-cyanobenzoyl]-$N^2$-(t-butylbenzoyl)-4-(hydroxy)-1,2-benzenediamine Using a procedure similar to Example 1C except starting with $N^1$-[4-(N,N-(bis-t-butoxycarbonyl)aminomethyl)-3-cyanobenzoyl]-$N^2$-(t-butylbenzoyl)-4-(benzyloxy)-1,2-benzenediamine, the title compound was obtained (92%); IR($CHCl_3$): 1233, 1370, 1649, 1749, 2970 $cm^{-1}$; NMR(300 MHz, $CDCl_3$): 5.08 (s, 2H); 6.39 (d, 1H, J=6.9 Hz); 7.16 (d, 1H, J=6.9 Hz); 7.21 (s, 1H); 7.35 (d, 1H, J=8.7 Hz); 7.54 (d, 2H, J=8.1 Hz); 7.88 (d, 2H, J=8.1 Hz); 8.22 (d, 1H, J=8.7 Hz); 8.37 (s, 1H); 9.44 (s, 1H); 9.52 (s, 1H); MS(FD): 542.1 (loss of BOC).

Analysis for $C_{36}H_{42}N_4O_7$: Calculated: C, 67.27; H, 6.59; N, 8.72. Found: C, 67.50; H, 6.67; N, 8.55.

B) $N^1$-[(1-iminoisoindolin-6-yl)carbonyl]-$N^2$-(t-butylbenzoyl)-4-hydroxy-1,2-benzenediamine trifluoroacetate Using a procedure similar to Example 9 except starting with $N^1$-[4-(N,N-(bis-t-butoxycarbonyl)aminomethyl)-3-cyanobenzoyl]-$N^2$-(t-butylbenzoyl)-4-hydroxy-1,2-benzenediamine, the title compound was obtained as a tan solid (quant.); IR(KBr): 1135, 1202, 1512, 1670 $cm^{-1}$; NMR(300 MHz, DMSO-$d_6$): 1.24 (s, 9H); 4.84 (s, 2H); 6.66 (d, 1H, J=8.7 Hz); 7.17 (s, 1H); 7.29 (d, 1H, J=8.7 Hz); 7.46 (d, 2H, J=8.1 Hz); 7.79 (d, 2H, J=8.1 Hz); 7.85 (d, 1H, J=8.1 Hz); 8.27 (d, 1H, J=7.8 Hz); 8.79 (s, 1H); 9.33 (s, 1H); 9.78 (s, 1H); 10.05 (s, 1H); 10.51 (s, 1H) ; MS(FD): 443.2.

Analysis for $C_{26}H_{26}N_4O_3.CF_3COOH.2H_2O$ Calculated: C, 56.76; H, 5.27; N, 9.45. Found: C, 56.71; H, 4.91; N, 8.67.

EXAMPLE 11

Preparation of 2-(4-t-butylbenzoylamino)-N-[3-(amino(imino)methyl)phenyl]benzamide hydrochloride A) 2-nitro-N-(3-cyanophenyl)benzamide Using a procedure similar to Example 1D except starting with 2-nitrobenzoic and 3-cyanoaniline, the title compound was obtained as a solid (92%); IR(KBr): 1344, 1524, 1645, 1666, 2229, 3232 cm$^{-1}$; NMR(300 MHz, CDCl$_3$): 7.49 (m, 2H); 7.71 (m, 3H); 7.81 (m, 2H); 7.99 (s, 1H); 8.18 d, 1H, J=8.1 Hz); MS(FD): 267.1.

Analysis for $C_{14}H_9N_3O_3$: Calculated: C, 62.92; H, 3.40; N, 15.72. Found: C, 62.74; H, 3.52; N, 15.71.

B) 2-amino-N-(3-cyanophenyl)benzamide

Using a procedure similar to Example 1C except starting with 2-nitro-N-(3-cyanophenyl)benzamide, the title compound was obtained as a solid (97%); IR(CHCl$_3$): 1527, 1583, 1614, 1668, 2234 cm$^{-1}$; NMR(300 MHz, CDCl$^3$): 6.76 (d, 1H, J=6.9 Hz); 7.32 (d, 1H, J=7.5 Hz); 7.48 (m, 4H); 7.76 (d, 1H, J=7.8 Hz); 7.88 (br s, 1H); 8.05 (s, 1H); MS(FD): 237.1.

Analysis for $C_{14}H_{11}N_3O.0.33H_2O$: Calculated: C, 69.30; H, 4.82; N, 17.32. Found: C, 69.61; H, 4.87; N, 17.16.

C) 2-(4-t-butylbenzoylamino)-N-(3-cyanophenyl)benzamide

Using a procedure similar to Example 1B except starting with 2-amino-N-(3-cyanophenyl)benzamide and 4-t-butylbenzoyl chloride, the title compound was obtained as a white solid (92%); MP: 194–6° C.; IR(KBr): 757, 1584, 1647, 2969, 3256 cm$^{-1}$; NMR(300 MHz, CDCl$_3$): 1.40 (s, 9H); 6.90 (t, 1H, J=7.2 Hz); 7.31 (m, 1H); 7.49–7.55 (m, 3H); 7.60 (d, 2H, J=7.5 Hz); 7.95 (d, 3H, J=8.4 Hz); 8.36 (s, 1H); 8.46 (d, 1H, J=8.4 Hz); 9.19 (s, 1H); 11.42 (s, 1H); MS(FD): 397.1.

Analysis for $C_{25}H_{23}N_3O_2.0.25H_2O$ Calculated: C, 74.70; H, 5.89; N, 10.45. Found: C, 74.84; H, 6.07; N, 9.60.

D) 2-(4-t-butylbenzoylamino)-N-[3-(amino(hydroxyimino)methyl)phenyl]benzamide

Using a procedure similar to Example 1F except starting with 2-(4-t-butylbenzoylamino)-N-(3-cyanophenyl)benzamide, the title compound was obtained as a white solid (42%);

NMR(300 MHz, CDCl$_3$): 1.34 (s, 9H); 5.02 (br s, 2H); 7.08 (t, 1H, J=2.1 Hz); 7.35–7.45 (m, 2H); 7.49 (d, 2H, J=6.9 Hz); 7.69 (d, 1H, J=6.0 Hz); 7.74 (d, 1H, J=8.3 Hz); 7.84 (s, 1H); 7.92 (d, 2H, J=8.1 Hz); 8.70 (d, 2H, J=8.4 Hz); 8.83 (s, 1H); 11.66 (s, 1H); MS(FD): 430.2.

Analysis for $C_{25}H_{26}N_4O_3.H_2O$: Calculated: C, 66.95; H, 6.29; N, 12.49. Found: C, 67.34; H, 5.88; N, 12.31.

E) 2-(4-t-butylbenzoylamino)-N-[3-(amino(imino)methyl)phenyl]benzamide hydrochloride Using a procedure similar to Example 1G except starting with 2-(4-t-butylbenzoyl-amino)-N-3-(amino(hydroxyimino)methyl)phenyl]benzamide, the title compound was obtained as a tan solid (66%); IR(CHCl$_3$): 1528, 1656, 1676, 2968 cm$^{-1}$;

NMR(300 MHz, DMSO-d$_6$): 1.29 (s, 9H); 7.30 (t, 1H, J=7.2 Hz); 7.57 (m, 5H); 7.83 (d, 2H, J=7.8 Hz); 7.89 (d, 1H, J=7.5 Hz); 7.94 (d, 1H, J=8.1); 8.17 (s, 1H); 8.36 (d, 1H, J=8.1 Hz); 9.01 (s, 2H); 9.35 (s, 2H); 10.85 (s, 1H); 11.42 (s, 1H); MS(FD): 415.3.

Analysis for $C_{25}H_{27}N_4O_2.HCl.1.5H_2O$ Calculated: C, 62.82; H, 6.33; N, 11.72. Found: C, 62.36; H, 6.36; N, 11.60.

EXAMPLE 12

Preparation of 2-[3-(amino(imino)methyl)benzoylamino]-N-(4-methoxyphenyl)benzamide A) 2-amino-N-(4-methoxyphenyl)benzamide A mixture of isatoic anhydride (4.894 g, 30 mmol), 4-methoxyaniline (3.695 g, 30 mmol) and toluene (60 mL) was heated to reflux for 5 h. After cooling, the reaction was filtered. The solid was triturated with CH$_2$Cl$_2$ (500 mL). This supernatant was combined with the above filtrate and concentrate. The residue was dissolved in CH$_2$Cl$_2$, decolorized with activated charcoal and crystallized from CH$_2$Cl$_2$/hexanes to give the title compound as a white solid (5.3 g, 73%); mp 116–7 C; MS(FD): 242.

Analysis for $C_{14}H_{14}N_2O_2$: Calculated: C, 69.41; H, 5.83; N, 11.56. Found: C, 69.16; H, 5.91; N, 11.31.

B) 2-(3-cyanobenzoylamino)-N-(4-methoxyphenyl)benzamide

Using a procedure similar to Example 1B except starting with 2-amino-N-(4-methoxyphenyl)benzamide, the title compound was obtained as a white solid (77%); mp 190–2 C; 3.74 (s, 3H), 6.94 (d, 2H, J=12.3 Hz), 7.33 (dd, 1H, J=8.2, 8.2 Hz), 7.60 (2H, J=12.3 Hz), 7.62 (m, 1H), 7.80 (dd, 1H, J=10.2, 8.2 Hz), 7.90 (d, 1H, J=8.2 Hz), 8.10 (d, 1H, J=8.2 Hz), 8.20 (d, 1H, J=8.2 Hz), 8.30 (s, 1H), 8.35 (1H, J=8.2 Hz), 10.43 (s, 1H), 11.75 ((s, 1H); MS(FD): 371.

Analysis for $C_{22}H_{17}N_3O_3.H_2O$: Calculated: C, 67.86; H, 4.92; N, 10.79. Found: C, 68.10; H, 4.88; N, 10.85.

C) 2-[3-(amino(hydroxyimino)methyl)benzoylamino]-N-(4-methoxyphenyl)benzamide

Using a procedure similar to Example 1F except starting with 2-(3-cyanobenzoylamino)-N-(4-methoxyphenyl)benzamide, the title compound was obtained as a white solid (98% ); mp 204–7 C; MS(FD): 404 (M+H).

Analysis for $C_{22}H_{20}N_4O_4$: Calculated: C, 65.34; H, 4.99; N, 13.85. Found: C, 66.00; H, 4.96; N, 13.54.

D) 2-[3-(amino(imino)methyl)benzoylamino]-N-(4-methoxyphenyl)benzamide

Using a procedure similar to Example 1G except starting with 2-[3-(amino(hydroxyimino)methyl)benzoylamino]-N-(4-methoxyphenyl)benzamide, the title compound was obtained as a light yellow solid (54%); mp 163–7 C; MS(FD): 388.1.

Analysis for $C_{22}H_{21}N_4O_3.HCl.2.5\ H_2O$: Calculated: C, 56.23; H, 5.58; N, 11.92. Found: C, 55.91; H, 5.07; N, 11.71.

EXAMPLE 13

Preparation of 3-(4-t-butylbenzoylamino)-N-[3-(amino(imino)methyl)phenyl]thiophene-2-carboxamide hydrochloride A) methyl 3-(4-t-butylbenzoylamino)thiophene-2-carboxylate To a mixture of methyl 3-aminothiophene-2-carboxylic acid (5.0 g, 35.0 mmol), pyridine(2.82 mL, 35.0 mmol), and dry methylene chloride (160 mL) at 0 C was added 4-tert-butylbenzoyl chloride(6.21 mL, 31.8 mmol) and stirred for 1 h. The reaction was concentrated, dissolved in ethyl acetate, washed with water (4x) and brine, MgSO$_4$ dried and concentrated. The residue was chromatographed (2% ethyl acetate/hexanes to 5% ethyl acetate/hexanes) to afford the title compound as a solid (9.67 g, 96% yield); NMR(CDCl$_3$) $\delta$1.36(s, 9H), 3.93(s, 3H), 7.54(d, J=8.4 Hz, 2H), 7.54(d, J=5.4 Hz, 1H), 7.95(d, J=8.4 Hz, 2H), 8.30(d, J=5.4 Hz, 1H), 11.16(s, 1H); MS(FD): 317.

Analysis for $C_{17}H_{19}NO_8S$: Calculated: C, 64.33; H, 6.03; N, 4.42. Found: C, 64.39; H, 5.98; N, 4.46.

B) 3-(4-t-butylbenzoylamino)thiophene-2-carboxylic acid

A mixture of methyl 3-(4-t-butylbenzoylamino)thiophene-2-carboxylate (9.67 g, 30 mmol), dioxane (75 mL) and 2 M sodium hydroxide (75 mL) was stirred for 16 h. The reaction was acidified to pH 2 with 5 M hydrochloric acid. The mixture was diluted with ethyl acetate and the aqueous layer was extracted with ethyl acetate (3 times). The combined organic layers was magnesium sulfate dried, filtered, and concentrated to afford the title compound as a solid (8.09 g, 89%); NMR(CDCl$_3$) d 1.36(s, 9H), 7.54(d, 2H, J=8.4 Hz), 7.61(d, 1H, J=5.1 Hz), 7.92(d, 2H, J=8.4 Hz), 8.34(d, 1H, J=5.1 Hz), 11.04(s, 1H); MS(FD): 303.

Analysis for $C_{16}H_{17}NO_8S$: Calculated: C, 63.34; H, 5.93; N, 4.62. Found: C, 63.56; H, 5.93; N, 4.32.

C) 2-(4-t-butylphenyl)-4H-thieno[3,2-d][1,3]oxazin-4-one

To a mixture of 3-(4-t-butylbenzoylamino)thiophene-2-carboxylic acid (8.09 g, 27 mmol) and methylene chloride (135 mL) was added oxalyl chloride (11.8 mL, 135 mmol). The mixture was heated until bubbling began. The reaction was stirred for 2 h without heating. The reaction was concentrated and the residue was dissolved in methylene chloride (135 mL). To this solution was added pyridine (2.2 mL, 27 mmol) and stirred at room temperature for 1 h. The reaction mixture was concentrated and partitioned between ethyl acetate and water. The organic layer was washed with water (4 times) and brine, MgSO$_4$ dried and concentrated. The residue was chromatographed (10% ethyl acetate/hexanes) to afford the title compound as a solid (7.44 g, 96%); NMR(CDCl$_3$) d 1.37(s, 9H), 7.35(d, J=5.1 Hz, 1H), 7.52(d, J=8.4 Hz, 2H), 7.91(d, J=5.1 Hz, 1H), 8.22(d, J=8.4 Hz, 2H); MS(FD): 285.

Analysis for $C_{16}H_{15}NO_2S$: Calculated: C, 67.34; H, 5.30; N, 4.91. Found: C, 67.51; H, 5.56; N, 4.76.

D) 3-(4-t-butylbenzoylamino)-N-(3-cyanophenyl)thiophene-2-carboxamide

To a mixture of 2-(4-t-butylphenyl)-4H-thieno[3,2-d]-[1,3]oxazin-4-one (400 mg, 1.4 mmol), 3-aminobenzonitrile (165 mg, 1.4 mmol) and THF (5 mL) was added 0.5 M potassium hexamethyldisilazide in toluene (3.08 mL, 1.54 mmol) and stirred for 15 min. The reaction was added NH$_4$Cl and ethyl acetate. The organic layer was washed with water (3×) and brine, MgSO$_4$ dried and concentrated. The residue was chromatographed (20% THF/hexanes) to give the title compound as a solid (580 mg, 51%); 1.37 (s, 9H), 7.47 (m, 4H), 7.57 (d, 2H, J=8.4 HZ); 7.68 (m, 1H), 7.98 (d, 2H, J=8.4 Hz); 8.20 (s, 1H); 8.42 (d, 1H, J=5.7 Hz); 11.80 (s, 1H); MS(FD): 403.

Analysis for $C_{23}H_{21}N_3O_2S$: Calculated: C, 68.46; H, 5.25; N, 10.41. Found: C, 67.83; H, 5.14; N, 10.08.

E) 3-(4-t-butylbenzoylamino)-N-[3-(amino(imino)methyl)phenyl]thiophene-2-carboxamide hydrochloride Into a mixture of 3-(4-t-butylbenzoylamino)-N-(3-cyanophenyl)thiophene-2-carboxamide (400 mg, 0.993 mmol), pyridine (10 mL), and triethylamine (1 mL) was bubbled hydrogen sulfide gas for 10 min. The solution was allowed to stand overnight. The solvent was concentrated and the residue was dissolved in ethyl acetate and washed with water (2×) and saturated sodium bicarbonate. The organic layer was MgSO$_4$ dried, filtered, and concentrated. The residue was dissolved in a mixture of 1:1 iodomethane:methanol (10 mL) and refluxed for 30 min. The reaction was concentrated and the residue was vacuum dried for 1 h. This residue was dissolved in a minimum amount of dry methanol and treated with ammonium acetate (230 mg, 2.98 mmol). The solution was heated to 65 degrees for 1 h, cooled to room temperature. The solution was triturated with diethyl ether and the solid was filtered off. The solid was dissolved in 10 mL of 1:1 tetrahydrofuran/water and treated with di-tert-butyl dicarbonate (1.08 g, 4.96 mmol) and potassium carbonate(822 mg, 5.96 mmol). After being stirred vigorously for 30 minutes, the solution was partitioned between with ethyl acetate and water. The aqueous layer was extracted with ethyl acetate (2×). The combined organic phase was MgSO$_4$ dried and concentrated. The residue was chromatographed (30% EtOAc/CH$_2$Cl$_2$) to give 3-(4-t-butylbenzoylamino)-N-[3-(N-t-butoxycarbonylamino(N-t-butoxycarbonylimino)methyl)phenyl]thiophene-2-carboxamide. This material was dissolved in trifluoroacetic acid (2 mL) and stirred for 1 h. The reaction was concentrated and the residue was dissolved in ethyl acetate. To this solution was added 1 M hydrochloric acid in ether, and the resulting mixture was sonicated for 5 min. The resulting solid was filtered, dissolved in water, and lyophilized to afford the title compound as a powder (170 mg, 37% yield); NMR(DMSO-d) δ1.38(s, 9H), 7.56 (m, 1H), 7.63 (m, 3H), 7.83 (d, 2H, J=8.29 Hz), 7.96 (d, 1H, J=5.27 Hz), 8.05 (m, 1H), 8.16 (m, 2H); MS(FD): 421.

Analysis for $C_{23}H_{24}N_4O_2S \cdot HCl \cdot 0.8 H_2O$: Calculated: C, 58.61; H, 5.69; N, 11.89. Found: C, 58.31; H, 5.40; N, 11.84.

EXAMPLE 14

Preparation of N$^1$-[3-[amino(hydroxyimino)methyl]benzoyl]]-N$^2$-(4-methoxybenzoyl)-1,2-benzenediamine

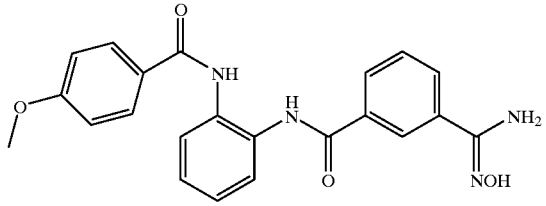

A) N-(4-methoxybenzoyl)-2-nitroaniline

Using a procedure similar to Example 1B except starting with 2-nitroaniline and p-anisoyl chloride, the title compound was obtained as a solid (98%); MS(FD): 272.0.

Analysis for $C_{14}H_{12}N_2O_4$: Calculated: C, 61.76; H, 4.44; N, 10.29. Found: C, 61.87; H, 4.61; N, 9.99.

B) N$^1$-(4-methoxybenzoyl)-1,2-benzenediamine

Using a procedure similar to Example 1C except starting with N-(4-methoxybenzoyl)-2-nitroaniline in ethyl acetate, the title compound was obtained as a white solid (99%); MS(FD): 242.

Analysis for $C_{14}H_{14}N_2O_2$: Calculated: C, 69.41; H, 5.82; N, 11.56. Found C, 69.63; H, 5.87; N, 11.39.

C) N$^1$-(3-cyanobenzoyl)-N$^2$-(4-methyoxybenzoyl)-1,2-benzenediamine

Using a procedure similar to Example 1B except starting with N$^1$-(4-methoxybenzoyl)-1,2-benzenediamine, the title compound was obtained as a solid (95%).

Analysis for $C_{22}H_{17}N_3O_3 \cdot 0.5H_2O$: Calculated: C, 69.46; H, 4.77; N, 11.05. Found: C, 69.53; H, 4.57; N, 10.82.

D) N$^1$-[3-(amino(hydroxyimino)methyl]benzoyl]]-N$^2$-(4-methoxybenzoyl)-1,2-benzenediamine Using a procedure similar to Example 1F except starting with N$^1$-(3-cyanobenzoyl)-N$^2$-(4-methyoxybenzoyl)-1,2-benzenediamine, the title compound was obtained as a solid (18%); MS(FD): 404.

Analysis for $C_{22}H_{20}N_4O_4$: Calculated: C, 65.34; H, 4.98; N, 13.85. Found: C, 65.29; H, 5.06; N, 13.83.

EXAMPLE 15

Preparation of N$^1$-[3-(aminoiminomethyl)benzoyl]]-N$^2$-(4-methoxybenzoyl)]-1,2-benzenediamine hydrochloride

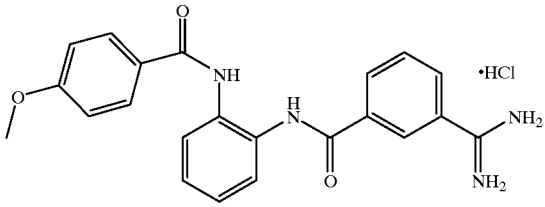

A solution of N$^1$-(3-cyanobenzoyl)-N$^2$-(4-methoxybenzoyl)-1,2-benzenediamine (0.5 g, 1.35 mmol) in triethylamine (5 mL) and pyridine (50 mL) was bubbled with hydrogen sulfide for 5 min. The reaction was stoppered and allowed to stand for 48 h. The reaction was concentrated and the residue was dissolved in ethyl acetate and washed twice with brine. The organic phase was MgSO$_4$ dried, filtered, and concentrated. The residue was dissolved in acetone (100 mL) and iodomethane (25 mL, 641.7 mmol) was added. The reaction was heated to reflux for 2 h, cooled, and concentrated. The residue was then dissolved in methanol (100 mL) and ammonium acetate (0.15 g, 5.4 mmol) was added. This solution was heated to reflux for 12 h, cooled and concentrated. The resulting residue was dissolved in THF (20 mL) and di-t-butyl dicarbonate (0.87 g, 4 mmol) was added, followed by a solution of K$_2$CO$_3$ (0.93 g, 6.75 mmol) in water (10 mL). After 2 h, the reaction was concentrated. The residue was dissolved in a minimal amount of chloroform and chromatographed (30% ethyl acetate/hexanes to ethyl acetate) to give the title compound as the free base. This material was dissolved in trifluoroacetic acid, stirred for 2 h, and concentrated. To the residue was added 1N HCl, and the mixture was stirred vigorously, filtered and vacuum dried to give the title compound as a white solid (220 mg, 42%); MS(FD): 389.1 (MH$^+$).

Analysis for C$_{22}$H$_{20}$N$_4$O$_3$.HCl: Calculated: C, 62.19; H, 4.98; N, 13.19; Cl, 8.34. Found C, 61.92; H, 5.09; N, 13.30; Cl, 8.22.

EXAMPLE 16

Preparation of N$^1$-[4-[amino(hydroxyimino)methyl] benzoyl]-N$^2$-(4-methoxybenzoyl)]-1,2-benzenediamine

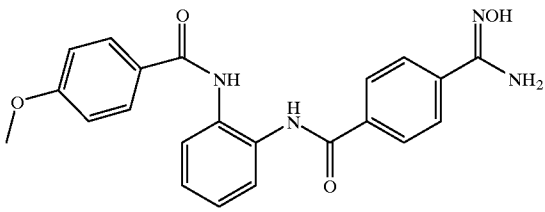

A) N$^1$-(4-cyanobenzoyl)-N$^2$-(4-methyoxybenzoyl)-1,2-benzenediamine

Using a procedure similar to Example 1B except starting with N$^1$-(4-methoxybenzoyl)-1,2-benzenediamine and 4-cyanobenzoyl chloride, the title compound was obtained as a solid (59%); MS(FD): 371.0.

Analysis for C$_{22}$H$_{17}$N$_3$O$_3$: Calculated: C, 71.15; H, 4.61; N, 11.31. Found C, 70.94; H, 4.85; N, 11.05.

B) N$^1$-[4-[amino(hydroxyimino)methyl]benzoyl]-N$^2$-(4-methoxybenzoyl)-1,2-benzenediamine Using a procedure similar to Example 1F except starting with N$^1$-(4-cyanobenzoyl)-N$^2$-(4-methyoxybenzoyl)-1,2-benzenediamine, the title compound was obtained as a solid (19%); MS(FD): 404.1.

Analysis for C$_{22}$H$_{20}$N$_4$O$_4$: Calculated: C, 65.34; H, 4.99; N, 13.85. Found C, 64.87; H, 4.97; N, 13.31.

EXAMPLE 17

Preparation of N$^1$-[4-(aminoiminomethyl)benzoyl]-N$^2$-(4-methoxybenzoyl)-1,2-benzenediamine hydrochloride

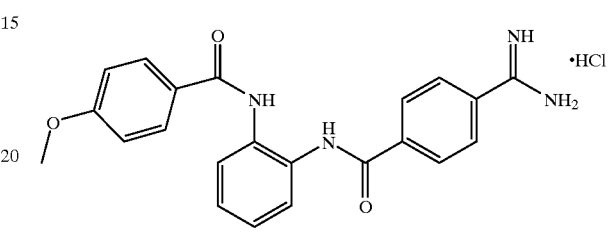

Using a procedure similar to Example 1G except starting with N$^1$-[4-[amino(hydroxyimino)methyl]benzoyl]-N$^2$-(4-methoxybenzoyl)-1,2-benzenediamine, the title compound was obtained as a solid (26%); MS(FD): 389.1 (MH$^+$).

Analysis for C$_{22}$H$_{20}$N$_4$O$_3$.1.1HCl.0.5H$_2$O: Calculated: C, 60.39; H, 5.09; N, 12.80. Found: C, 60.30; H, 4.90; N, 12.48.

EXAMPLE 18

Preparation of N$^1$-[2-fluoro-4-(aminoiminomethyl) benzoyl]-N$^2$-(4-methoxybenzoyl)-1,2-benzenediamine hydrochloride

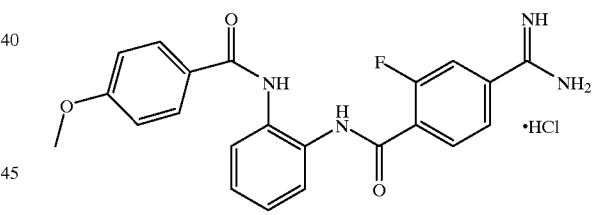

A) N$^1$-(2-fluoro-4-cyanobenzoyl)-N$^2$-(4-methyoxybenzoyl)-1,2-benzenediamine

To a solution of N$^1$-(4-methoxybenzoyl)-1,2-benzenediamine (0.5 g, 1.8 mmol), 2-fluoro-4-cyanobenzoic acid (0.3 g, 1.8 mmol) and N,N-diisopropylethylamine (0.23 g, 1.8 mmol) in DMF (5 mL) was added EDC (0.42 g, 2.2 mmol). After 48 h, 2-fluoro-4-cyanobenzoic acid (0.3 g, 1.8 mmol) and EDC (0.35 g, 1.8 mmol) were added. After an additional 24 h, the reaction was concentrated; and the residue was dissolved in ethyl acetate, washed with 1 N citric acid, brine, satd aq NaHCO$_3$ and brine. The organic layer was MgSO$_4$ dried, crystallized, filtered with ether wash, and dried under vacuum to give the title compound as a white solid 280 mg (40%); MS(FD): 389.1

Analysis for C$_{22}$H$_{16}$FN$_3$O$_3$: Calculated: C, 67.86; H, 4.14; N, 10.79. Found C, 68.07; H, 4.20; N, 10.66.

B) N$^1$-[2-fluoro-4-(aminoiminomethyl)benzoyl]-N$^2$-(4-methoxybenzoyl)-1,2-benzenediamine hydrochloride Using a procedure similar to Example 15 except starting with N$^1$-(2-fluoro-4-cyanobenzoyl)-N$^2$-(4- methyoxybenzoyl)-1,2-benzenediamine, the title compound as obtained as a solid (12%); MS(IS): 407.1 (MH+).

Analysis for $C_{22}H_{19}FN_4O_3 \cdot HCl$: Calculated: C, 59.67; H, 4.55; N, 12.65. Found C, 59.45; H, 4.63; N, 12.39.

EXAMPLE 19

Preparation of 5-benzyloxycarbonyl-$N^1$-[3-[amino(hydroxyimino)methyl]benzoyl]-$N^2$-(4-t-butylbenzoyl)-1,2-benzenediamine

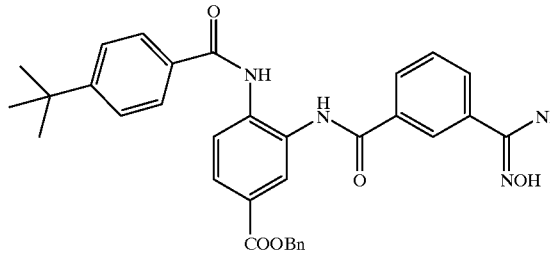

A) 5-methoxycarbonyl-$N^1$-(3-cyanobenzoyl)-1,2-benzenediamine

To a solution of 4-methoxycarbonyl-1,2-benzenediamine (8 g, 48 mmol) and pyridine (4 mL, 48 mmol) in acetonitrile (300 mL) at 0° C. was added 3-cyanobenzoyl chloride (8 g, 48 mmol). After 12 h, the reaction was concentrated and the residue was suspended with vigorous stirring in ethyl acetate (500 mL) and 1 M citric acid (200 mL). The solid was filtered, washed with diethyl ether and vacuum dried to give the title compound as an off-white solid (8 g, 56%); MS(FD): 295.1 (M+).

Analysis for $C_{16}H_{13}N_3O_3$: Calculated: C, 65.08; H, 4.44; N, 14.23. Found: C, 65.33; H, 4.54; N, 14.39.

B) 5-methoxycarbonyl-$N^1$-(3-cyanobenzoyl)-$N^2$-(4-t-butylbenzoyl)]-1,2-benzenediamine Using a procedure similar to Example 1B except starting with 4-t-butylbenzoyl chloride and 5-methoxycarbonyl-$N^1$-(3-cyanobenzoyl)]-1,2-benzenediamine, the title compound was obtained as a solid (2.32 g, 60%); MS(FD): 455.2.

Analysis for $C_{27}H_{25}N_3O_4$: Calculated: C, 71.19; H, 5.53; N, 9.22. Found: C, 71.31; H, 5.82; N, 9.35.

C) 5-benzyloxycarbonyl-$N^1$-(3-cyanobenzoyl)-$N^2$-(4-t-butylbenzoyl)-1,2-benzenediamine To a solution of 5-methoxycarbonyl-$N^1$-(3-cyanobenzoyl)]-$N^2$-(4-t-butylbenzoyl)-1,2-benzenediamine (2.6 g, 5.7 mmol) in THF (80 mL) was added methanol (27 mL), followed by a solution of $LiOH \cdot H_2O$ (1 g, 22.8 mmol) in water (27 mL). After 12 h, the pH was adjusted to 3 with conc HCl and the mixture was concentrated. The residue was partitioned between ethyl acetate and water. The organic layer was washed with 1 N HCl, brine (2×), $MgSO_4$ dried, and concentrated. To the residue dissolved in DMF (20 mL) was added benzyl bromide (1.06 g, 6.2 mmol), followed by $K_2CO_3$ (1.6 g, 11.4 mmol). After 3 h, the reaction was concentrated and the residue was dissolved in ethyl acetate and washed with satd aq $NaHCO_3$ followed by brine. The organic layer was $MgSO_4$ dried and 5 g of silica gel was added. This mixture was concentrated and chromatographed (20% ethyl acetate/hexanes to 60% ethyl acetate/hexanes) to give the title compound as a white solid (1.2 g, 40%); MS(FD): 531.0.

Analysis for $C_{33}H_{29}N_3O_4$: Calculated: C, 74.56; H, 5.50; N, 7.90. Found: C, 74.32; H, 5.64; N, 7.63.

D) 5-benzyloxycarbonyl-$N^1$-[3-[amino(hydroxyimino)methyl]benzoyl]-$N^2$-(4-t-butylbenzoyl)-1,2-benzenediamine Using a procedure similar to Example 1F except starting with 5-benzyloxycarbonyl-$N^1$-(3-cyanobenzoyl)-$N^2$-(4-t-butylbenzoyl)-1,2-benzenediamine, the title compound was obtained as a solid (47%); MS(FD): 564 (M+)

Analysis for $C_{33}H_{32}N_4O_5$: Calculated: C, 69.10; H, 5.80; N, 9.76. Found: C, 69.52; H, 5.84; N, 9.42.

EXAMPLE 20

Preparation of 5-carboxy-$N^1$-[3-(aminoiminomethyl)benzoyl]]-$N^2$-(4-t-butylbenzoyl)-1,2-benzenediamine hydrochloride

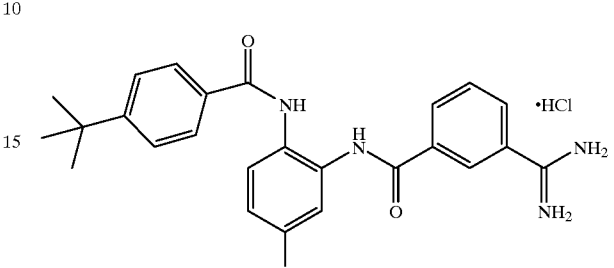

Using a procedure similar to Example 1G, except starting with 5-benzyloxycarbonyl-$N^1$-[3-[amino(hydroxyimino)methyl]benzoyl]-$N_2$-(4-t-butylbenzoyl)-1,2-benzenediamine, the title compound was obtained as a solid (330 mg, 83%).

Analysis for $C_{26}H_{26}N_4O_4 \cdot 1.1HCl \cdot 0.5H_2O$: Calculated: C, 61.52; H, 5.58; N, 11.03; Cl, 7.68. Found: C, 61.15; H, 5.49; N, 11.09; Cl, 7.90.

EXAMPLE 21

Preparation of 4-benzyloxycarbonyl-$N^1$-[3-[amino(hydroxyimino)methyl]benzoyl]]-$N^2$-(4-t-butylbenzoyl)-1,2-benzenediamine

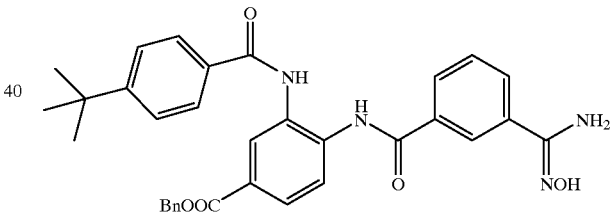

A) 4-methoxycarbonyl-$N^2$-(4-t-butylbenzoyl)-1,2-benzenediamine

Using a procedure similar to Example 1B except starting with 4-methoxycarbonyl-1,2-benzenediamine and 4-t-butylbenzoyl chloride, the title compound was obtained as a solid (10.8 g, 65%); MS(FD): 326.2.

Analysis for $C_{19}H_{22}N_2O_3$: Calculated: C, 69.92; H, 6.79; N, 8.58. Found: C, 70.02; H, 6.91; N, 8.61.

B) 4-methoxycarbonyl-$N^1$-(3-cyanobenzoyl)-$N^2$-(4-t-butylbenzoyl)]-1,2-benzenediamine Using a procedure similar to Example 1B except starting with 3-cyanobenzoyl chloride and 4-methoxycarbonyl-$N^2$-(4-t-butylbenzoyl)-1,2-benzenediamine, the title compound was obtained as a solid (3.4 g, 81%); MS(FD): 455.3.

Analysis for $C_{27}H_{25}N_3O_4$: Calculated: C, 71.19; H, 5.53; N, 9.22. Found: C, 71.08; H, 5.59; N, 9.34.

C) 4-benzyloxycarbonyl-$N^1$-(3-cyanobenzoyl)-$N^2$-(4-t-butylbenzoyl)-1,2-benzenediamine Using a procedure similar to Example 19 except starting from 4-methoxycarbonyl-$N^1$-(3-cyanobenzoyl)-$N^2$-(4-t-butylbenzoyl)1,2-benzenediamine, the title compound was obtained as a solid (3.3 g, 65%); MS(FD): 531.0.

Analysis for C₃₃H₂₉N₃O₄: Calculated: C, 74.56; H, 5.50; N, 7.90. Found: C, 74.42; H, 5.73; N, 7.73.

D) 4-benzyloxycarbonyl-N¹-[3-[amino(hydroxyimino) methyl]-benzoyl]-N²-(4-t-butylbenzoyl)-1,2-benzenediamine Using a procedure similar to Example 1F except starting from 4-benzyloxycarbonyl-N¹-(3-cyanobenzoyl)-N²-(4-t-butylbenzoyl)-1,2-benzenediamine, the title compound was obtained as a solid (1.62 g, 76%); MS(FD): 564.

Analysis for C₃₃H₃₂N₄O₅: Calculated: C, 70.70; H, 5.71; N, 9.92. Found: C, 70.25; H, 5.62; N, 9.81.

EXAMPLE 22

Preparation of 4-carboxy-N¹-[4-(aminoiminomethyl)benzoyl]-N²-(4-t-butylbenzoyl)-1,2-benzenediamine hydrochloride

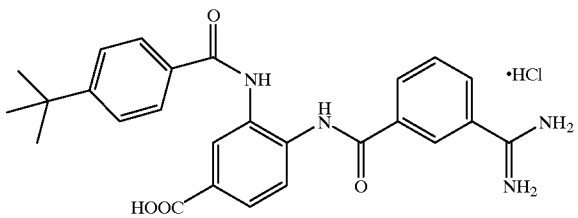

Using a procedure similar to Example 1G except starting from 4-benzyloxycarbonyl-N¹-[3-[amino(hydroxyimino) methyl]benzoyl]-N²-(4-t-butylbenzoyl)-1,2-benzenediamine, the title compound was obtained as a solid (394 mg, 90%); MS(FD): 459.

Analysis for C₂₆H₂₆N₄O₄·1.15HCl·1H₂O: Calculated: C, 60.24; H, 5.67; N, 10.80; Cl, 7.86. Found: C, 60.43; H, 5.46; N, 10.84; Cl, 7.84.

EXAMPLE 23

Preparation of 4-methoxycarbonyl-N¹-[3-[amino (hydroxyimino)methyl]benzoyl]-N²-(4-t-butylbenzoyl)-1,2-benzenediamine

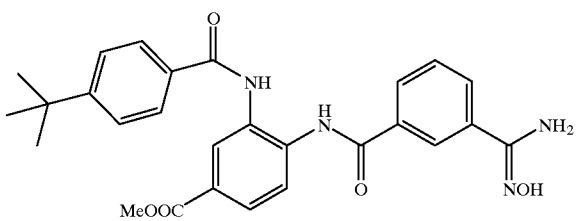

Using a procedure similar to Example 1F except starting from 4-methoxycarbonyl-N¹-(3-cyanobenzoyl)-N²-(4-t-butylbenzoyl)-1,2-benzenediamine, the title compound was obtained as a solid (1.6 g, 75%); MS(FD): 488.

Analysis for C₂₇H₂₈N₄O₅: Calculated: C, 66.38; H, 5.78; N, 11.47. Found: C, 66.42; H, 5.91; N, 11.43.

EXAMPLE 24

Preparation of 4-methoxycarbonyl-N¹-[3-(aminoiminomethyl)benzoyl]-N²-(4-t-butylbenzoyl)-1,2-benzenediamine hydrochloride

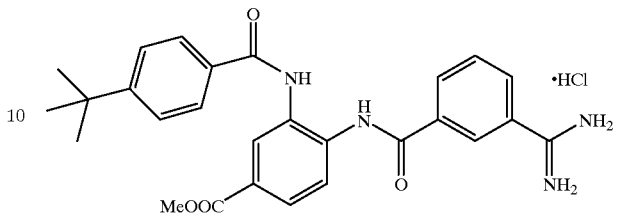

Using a procedure similar to Example 1G except starting from 4-methoxycarbonyl-N¹-[3-[amino(hydroxyimino) methyl]benzoyl]-N²-(4-t-butylbenzoyl)-1,2-benzenediamine, the title compound was obtained as a solid (0.95 g, 57%); MS(FD): 473.

EXAMPLE 25

Preparation of 5-methoxycarbonyl-N¹-[3-[amino (hydroxyimino)methyl]benzoyl]-N²-(4-t-butylbenzoyl)-1,2-benzenediamine

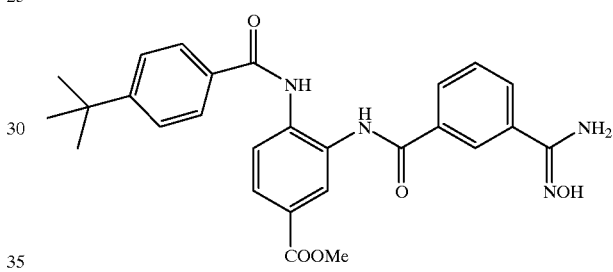

Using a procedure similar to Example 1F except starting from 5-methoxycarbonyl-N¹-(3-cyanobenzoyl)-N²-(4-t-butylbenzoyl)-1,2-benzenediamine, the title compound was obtained as a solid (0.60 g, 56%); MS(FD): 489.2 (MH⁺).

Analysis for C₂₇H₂₇N₄O₅: Calculated: C, 66.38; H, 5.78; N, 11.47. Found: C, 66.10; H, 5.80; N, 11.19.

EXAMPLE 26

Preparation of 4-methoxycarbonyl-N¹-[3-[(ethoxycarbonylamino)iminomethyl]benzoyl]-N²-(4-t-butylbenzoyl)-1,2-benzenediamine

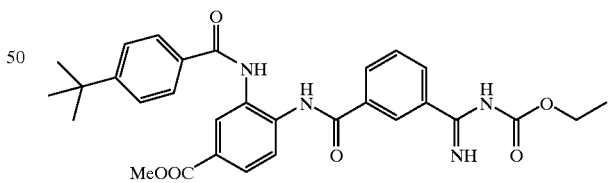

To a solution of 4-methoxycarbonyl-N¹-[4-(aminoiminomethyl)benzoyl]]-N²-(4-t-butylbenzoyl)-1,2-benzenediamine hydrochloride (250 mg, 0.49 mmol) and K₂CO₃ (200 mg, 1.5 mmol) in THF (10 mL) and water (10 mL) was added a solution of ethyl chloroformate (0.07 mL, 0.74 mmol) in THF (5 mL). After 1 h, the reaction was concentrated and the residue was dissolved in ethyl acetate. The organic solution was washed with satd aq NH₄Cl (2×), water, satd aq NaHCO₃, water, brine, MgSO₄ dried, and concentrated. The residue was chromatographed (50% ethyl acetate/hexanes to 75% ethyl acetate/hexanes) to give the title compound as a solid (150 mg, 56%); FD-MS(FD): 544.

EXAMPLE 27

Preparation of 4-methoxycarbonyl-N¹-[3-[(acetoxymethoxycarbonyl)amino]iminomethyl]benzoyl]-N²-(4-t-butylbenzoyl)-1,2-benzenediamine

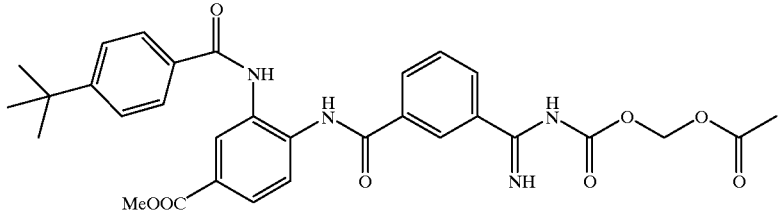

Using a procedure similar to Example 26 except starting from 4-methoxycarbonyl-N¹-[4-(aminoiminomethyl)benzoyl]-N²-(4-t-butylbenzoyl)-1,2-benzenediamine hydrochloride and acetoxymethyl 4-nitrophenyl carbonate, the title compound was obtained as a solid (54%); MS(FD): 589.

Analysis for $C_{31}H_{32}N_4O_8$: Calculated: C, 63.26; H, 5.48; N, 9.52. Found: C, 63.13; H, 5.57; N, 9.32.

EXAMPLE 28

Preparation of N¹-[3-[(methoxycarbonylamino)iminomethyl]benzoyl]]-N²-(4-methoxybenzoyl)-1,2-benzenediamine

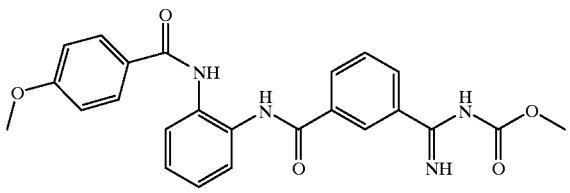

Using a procedure similar to Example 26 except starting from methyl chloroformate and N¹-[3-(aminoiminomethyl)benzoyl]-N₂-(4-methoxybenzoyl)-1,2-benzenediamine hydrochloride, the title compound was obtained as a solid (74%); MS(FD): 446.

Analysis for $C_{24}H_{22}N_4O_5$: Calculated: C, 64.56; H, 4.96; N, 12.55. Found: C, 64.43; H, 5.16; N, 12.07.

EXAMPLE 29

Preparation of N¹-[3-[(ethoxycarbonylamino)iminomethyl]benzoyl]-N²-(4-methoxybenzoyl)-1,2-benzenediamine

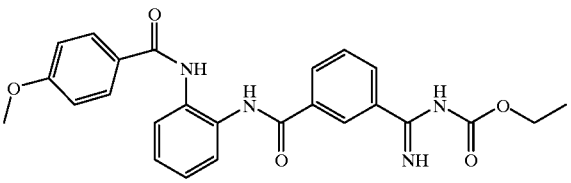

Using a procedure similar to Example 26 except starting from N¹-[3-(aminoiminomethyl)benzoyl]-N²-(4-methoxybenzoyl)-1,2-benzenediamine hydrochloride, the title compound was obtained as a solid (57%); MS(FD): 460.1.

Analysis for $C_{25}H_{24}N_4O_5 \cdot 0.9H_2O$: Calculated: C, 62.99; H, 5.46; N, 11.75. Found: C, 63.10; H, 5.33; N, 11.63.

EXAMPLE 30

Preparation of N¹-[3-[(1,1-dimethylethoxycarbonylamino)iminomethyl]benzoyl]-N²-(4-methoxybenzoyl)-1,2-benzenediamine

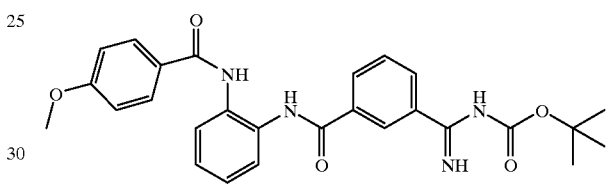

Using a procedure similar to Example 26 except starting from N¹-[3-(aminoiminomethyl)benzoyl]-N²-(4-methoxybenzoyl)-1,2-benzenediamine hydrochloride, the title compound was obtained as a solid (43%); MS(FD): 489.

Analysis for $C_{27}H_{28}N_4O_5$: Calculated: C, 66.38; H, 5.78; N, 11.47. Found: C, 66.17; H, 5.79; N, 11.33.

EXAMPLE 31

Preparation of N¹-[2-hydroxy-3-(aminoiminomethyl)benzoyl]-N²-(4-methoxybenzoyl)-1,2-benzenediamine hydrochloride

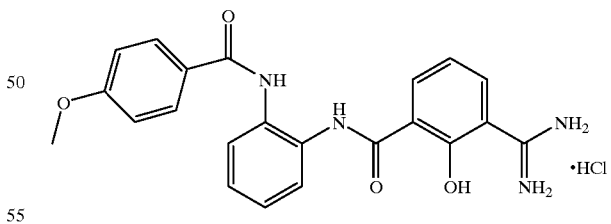

A) N¹-(2-fluoro-3-cyanobenzoyl)-N₂-(4-methyoxybenzoyl)-1,2-benzenediamine

Using a procedure similar to Example 1B except starting from 2-fluoro-3-cyanobenzoic acid and N¹-(4-methoxybenzoyl)-N²-benzenediamine, the title compound was obtained as a solid (74%); MS(FD): 389.1.

B) N¹-[(3-amino-1,2-benzisoxazol-7-yl)carbonyl]-N²-(4-methoxybenzoyl)-1,2-benzenediamine To a suspension of potassium t-butoxide (92 mg, 0.82 mmol) in DMF (5 mL) was added acetone oxime hydrochloride (60 mg, 0.82 mmol). After 1 h, N¹-(2-fluoro-3- cyanobenzoyl)-N²-(4-methoxybenzoyl)-1,2-benzenediamine (290 mg, 0.74 mmol) was added. After another 2 h, potassium t-butoxide (92 mg, 0.82 mmol) and acetone oxime hydrochloride (60 mg, 0.82 mmol) were added. After 12 h, the reaction was concentrated and the residue was dissolved in ethyl acetate and washed with water (2×), brine, MgSO₄ dried, and concentrated. The resulting solid was dissolved in ethanol (35 mL), 5% HCl (35 mL) was added, and the mixture was refluxed for 1 h. The reaction was cooled, concentrated to 2 mL, diluted with ethyl acetate (250 mL), and neutralized with satd aq NaHCO₃. The organic layer was washed with satd aq NaHCO₃ (2×) and brine, MgSO₄ dried, concentrated and crystallized to give the title compound as an off-white solid (106 mg, 35%); MS(FD): 402.1.

Analysis for $C_{22}H_{18}N_4O_4$: Calculated: C, 65.66; H, 4.51; N, 13.92. Found: C, 65.41; H, 4.61; N, 13.73.

C) $N^1$-[2-hydroxy-3-(aminoiminomethyl)benzoyl]-$N^2$-(4-methoxybenzoyl)-1,2-benzenediamine hydrochloride Using a procedure similar to Example 1C, except starting from $N^1$-[(3-amino-1,2-benzisoxazol-7-yl)carbonyl]-$N^2$-(4-methoxybenzoyl)-1,2-benzenediamine, the title compound was obtained as a solid (20 mg, 32%); MS(IS): 405.1 (MH⁺).

Analysis for $C_{22}H_{20}N_4O_{44}\cdot1.1HCl\cdot1.4H_2O$: Calculated: C, 56.25; H, 5.13; N, 11.92; Cl, 8.30. Found: C, 56.39; H, 4.63; N, 11.66; Cl, 8.38.

EXAMPLE 32

Preparation of N-[3-(aminoiminomethyl)benzoyl]-2-[(4-methoxyphenoxy)methyl]aniline hydrochloride

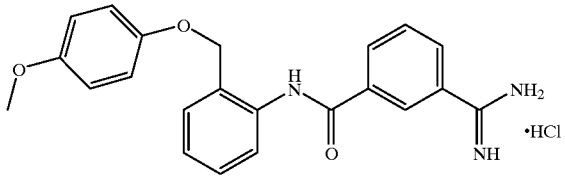

A) 2-[(4-methoxyphenoxy)methyl]nitrobenzene

To a suspension of potassium t-butoxide (5.7 g, 51 mmol) in THF (200 mL) was added 4-methoxyphenol (6.3 g, 51 mmol). After 10 min, 2-nitrobenzyl bromide (10 g, 46 mmol) was added. After 48 h, the reaction was concentrated and the residue was dissolved in ethyl acetate, washed with 1 N citric acid (2×), brine, satd aq NaHCO₃ (2×), water, and brine. The organic layer was MgSO₄ dried, concentrated, triturated with ether, filtered and vacuum dried to give the title compound as an off-white solid (8.4 g, 71%); MS(FD): 259.

Analysis for $C_{14}H_{13}NO_4$: Calculated: C, 64.86; H, 5.05; N, 5.40. Found: C, 64.62; H, 5.05; N, 5.43.

B) 2-[(4-methoxyphenoxy)methyl]aniline

Using a procedure similar to Example 1C except starting from from 2-[(4-methoxyphenoxy)methyl]nitrobenzene, the title compound was obtained as a solid (2.0 g, 59%); MS(FD): 229.1.

Analysis for $C_{14}H_{15}NO_2$: Calculated: C, 73.34; H, 6.59; N, 6.11. Found: C, 73.38; H, 6.46; N, 6.19.

C) N-(3-cyanobenzoyl)-2-[(4-methoxyphenoxy)methyl]aniline

Using a procedure similar to Example 1B except starting from 2-[(4-methoxyphenoxy)methyl]aniline and 3-cyanobenzoyl chloride, the title compound was obtained as a solid (0.50 g, 36%); MS(FD): 359.

Analysis for $C_{22}H_{18}N_2O_3$: Calculated: C, 73.73; H, 5.06; N, 7.82. Found: C, 73.99; H, 5.21; N, 7.87.

D) N-[3-(aminoiminomethyl)benzoyl]-2-[(4-methoxyphenoxy)methyl]-aniline hydrochloride Using a procedure similar to Example 15 except starting from 1-[N-(3-cyanobenzoyl)]-2-[(4-methoxyphenyloxy)methyl]aniline, the title compound was obtained as a solid (18%); MS(IS): 376.1 (MH⁺).

Analysis for $C_{22}H_{21}N_3O_3\cdot1.1HCl\cdot0.3H_2O$: Calculated: C, 62.78; H, 5.44; N, 9.98; Cl, 9.26. Found: C, 62.99; H, 5.23; N, 10.05; Cl, 9.21.

EXAMPLE 33

Preparation of $N^1$-[3-(aminoiminomethyl)benzoyl]-$N^2$-[(4-methoxybenzyl)oxy]-aniline hydrochloride

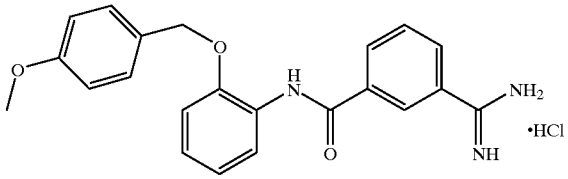

A) N-(3-cyanobenzoyl)-2-hydroxyaniline

Using a procedure similar to Example 1B except starting from 2-hydroxyaniline, the title compound was obtained as a solid (70%); MS(FD): 238.

Analysis for $C_{14}H_{10}N_2O_2$: Calculated: C, 70.58; H, 4.23; N, 11.76. Found: C, 70.83; H, 3.99; N, 11.46.

B) N-(3-cyanobenzoyl)-2-[(4-methoxybenzyl)oxy]aniline

Using a procedure similar to Example 32A except starting from 4-methoxybenzyl chloride and $N^1$-(3-cyanobenzoyl)-2-hydroxyaniline and using $K_2CO_3$/DMF in place of potassium t-butoxide/THF, the title compound was obtained as a solid (27%); MS(FD): 359.

Analysis for $C_{22}H_{18}N_2O_3$: Calculated: C, 73.73; H, 5.06; N, 7.82. Found: C, 73.44; H, 4.98; N, 7.64.

C) N-[3-(aminoiminomethyl)benzoyl]-2-[(4-methoxybenzyl)oxy]aniline hydrochloride Using a procedure similar to Example 15, except starting from $N^1$-(3-cyanobenzoyl)-$N^2$-[(4-methoxybenzyl)oxy]aniline, the title compound was obtained as a solid (10%); MS(IS): 376.1 (MH⁺).

Analysis for $C_{22}H_{21}N_3O_3\cdot1.2HCl\cdot H_2O$: Calculated: C, 60.44; H, 5.58; N, 9.61; Cl, 9.73. Found: C, 60.22; H, 5.22; N, 9.91; Cl, 9.96.

EXAMPLE 34

Preparation of 2-[3-(aminoiminomethyl)benzyloxy]-N-(4-methoxybenzoyl)aniline hydrochloride

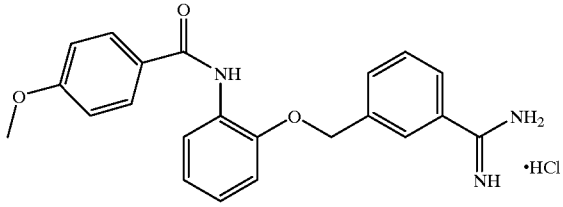

A) 2-(3-cyanobenzyloxy)-N-(4-methoxybenzoyl) aniline

Using a procedure similar to Example 33A and 33B except starting from 2-hydroxyaniline, p-anisoyl chloride and 3-cyanobenzyl bromide, the title compound was obtained as a solid (700 mg, 48%); MS(FD): 358.1.

Analysis for $C_{22}H_{18}N_2O_3$: Calculated: C, 73.73; H, 5.06; N, 7.82. Found: C, 73.67; H, 5.27; N, 7.61.

B) 2-[3-(aminoiminomethyl)benzyloxy]-N-(4-methoxybenzoyl)aniline hydrochloride

Using a procedure similar to Example 15, except starting from 2-(3-cyanobenzyloxy)-N-(4-methoxybenzoyl)aniline, the title compound was obtained as a solid (10%); MS(IS): 376.2 (MH+).

Analysis for $C_{22}H_{21}N_3O_3 \cdot 1.1HCl \cdot 0.5H_2O$: Calculated: C, 62.24; H, 5.48; N, 9.89; Cl, 9.19. Found: C, 62.33; H, 5.32; N, 9.97; Cl, 9.02.

EXAMPLE 35

Preparation of $N^1$-[[1-(amino(imino)methyl))piperidin-3-yl]carbonyl]-$N^2$-(t-butylbenzoyl)-1,2-benzenediamine trifluoroacetate

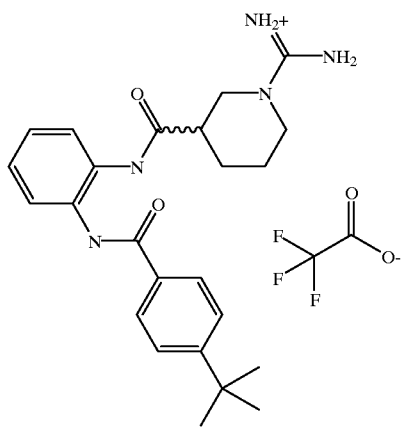

A) 1-(benzyloxycarbonylamino(benzyloxycarbonylimino)methyl)piperidine-3-carboxylic acid To a solution of nipecotic acid (1.66 g, 12.8 mmol) in 2 N NaOH (12.8 mL, 25.6 mmol) and dioxane (30 mL) was added 1,3-bis(benzyloxycarbonyl)-2-methyl-2-thiopseudourea (4.6 g, 12.8 mmol). After 48 h, the reaction mixture was added to $H_2O$ (200 mL) and $Et_2O$ (200 mL). The aqueous layer was separated and extracted with $Et_2O$ (2×200 mL). The aqueous layer was acidified to pH 2.0 with 3 N HCl and extracted with EtOAc (500 mL). The organic layer was $MgSO_4$ dried and concentrated to give the title compound (4.0 g, 71%): TLC $R_f$=0.65 (1:15: 135 Acetic Acid:Methanol:Chloroform); NMR (CDCl$_3$) δ1.55–1.92 (m, 6H), 2.00–2.15 (m, 1H), 2.70–2.80 (m, 1H), 3.20–3.35 (q, 1H), 3.38–3.45 (m, 1H), 3.75–4.10 (m, 1H), 5.10 (s, 2H), 5.22 (s, 2H), 7.30–7.40 (m, 10H); FD-MS 440 (MH+).

Analysis for $C_{23}H_{25}N_3O_6$: Calculated: C, 62.86; H, 5.73; N, 9.56. Found: C, 62.64; H, 5.79; N, 9.38.

B) $N^1$-[[1-(benzyloxycarbonylamino(benzyloxycarbonylimino)methyl)piperidin-3-yl]carbonyl]-$N^2$-(t-butylbenzoyl)-1,2-benzenediamine To a solution of 1-(benzyloxycarbonylamino(benzyloxycarbonylimino)methyl)piperidine-3-carboxylic acid (1.2 g, 2.7 mmol) in $CH_2Cl_2$ (30 mL) was added 2-(4-t-butylbenzoylamino)aniline (obtained from 4-t-butylbenzoyl chloride and 2-nitroaniline using procedures similar to those of Example 1-B and 1-C)(0.730 g, 2.7 mmol), DCC (0.556 g, 2.7 mmol), and HOAt (0.367 g, 2.7 mmol). The reaction was stirred for 24 h. The resultant precipitate was filtered and the filtrate was concentrated. The residue was dissolved in EtOAc (250ml) and washed with 1N NaHCO$_3$, water, and 1.5 N citric acid. The organic layer was MgSO$_4$ dried and concentrated to give the title compound as an amorphous solid (2.4 g, 100%).

C) $N^1$-[[1-(amino(imino)methyl))piperidin-3-yl]carbonyl]-$N^2$-(t-butylbenzoyl)-1,2-benzenediamine trifluoroacetate A mixture of $N^1$-[[1-(benzyloxycarbonylamino(benzyloxycarbonylimino)methyl)piperidin-3-yl]carbonyl]-$N^2$-(t-butylbenzoyl)-1,2-benzenediamine (2.4 g), ethanol (60 mL), water (25 mL), 1 N HCl (5.0 mL, 5.0 mmol), and 5% Pd/C catalyst (1.5 g) was hydrogenated at 1 atm. After the reaction was completed, the catalyst was filtered through diatomaceous earth. The filtrate was concentrated and vacuum dried overnight. The residue was dissolved in 0.1% TFA, filtered through a Millipore 0.5 mm filter, and chromatographed on a 5×25 cm column Vydac $C_{18}$ resin (5% $CH_3CN/H_2O$ to 50% $CH_3CN/H_2O$) to give the title compound as a white solid (0.550 g, 37%); MS(FAB): 422 (MH+).

Analysis for $C_{26}H_{35}F_3N_5O_4 \cdot H_2O$: Calculated: C, 56.41; H, 5.83; N, 12.65. Found: C, 56.41; H, 5.94; N, 12.27.

EXAMPLE 36

Preparation of $N^1$-[[1-(amino(imino)methyl))piperidin-3-yl]carbonyl]-$N^2$-(4-t-butylbenzoyl)-4-methoxycarbonyl-1,2-benzenediamine hydrochloride

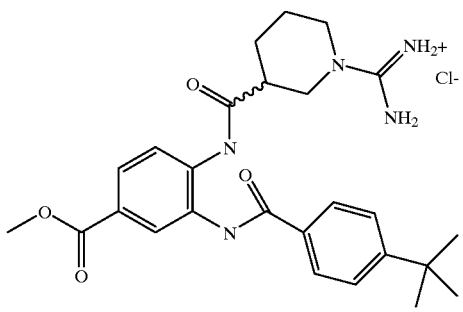

A) 4-methoxycarbonyl-N2-(4-t-butylbenzoyl)-1,2-benzenediamine

Using a procedure similar to Example 19A except starting with 4-tert-butylbenzoyl chloride and crystallization of the crude product from 1:1:1 $CH_2Cl_2$:$Et_2O$:hexane, gave the title compound as a solid (76%); TLC: $R_f$=0.65 (ethyl acetate:hexane 1:1); MS(FAB): 327 (MH+).

Analysis for $C_{19}H_{22}N_2O_3$: Calculated: C, 69.92; H, 6.79; N, 8.58. Found: C, 69.69; H, 6.63; N, 8.5.

B) $N^1$-[[1-(benzyloxycarbonylamino(benzyloxycarbonylimino)methyl)piperidin-3-yl]carbonyl]-$N^2$-(4-t-butylbenzoyl)-4-methoxycarbonyl-1,2-benzenediamine Using a procedure similar to Example 35B except starting with 4-methoxycarbonyl-$N^2$-(4-t-butylbenzoyl)-1,2-benzenediamine and using chromatography (CHCl$_3$ to 30% EtOAc/CHCl$_3$), the title compound was obtained as an amorphous solid (1.54 g,.44%); TLC: $R_f$=0.29 (8:2 chloroform:ethyl acetate); MS(FD): 748 (MH+).

Analysis for $C_{42}H_{45}N_5O_8$: Calculated: C, 67.46; H, 6.07; N, 9.36. Found: C, 67.47; H, 5.98; N, 9.10.

C) $N^1$-[[1-(amino(imino)methyl))piperidin-3-yl]carbonyl]-$N_2$-(4-t-butylbenzoyl)-4-methoxycarbonyl-1,2-benzenediamine hydrochloride Using a procedure similar to Example 35 except starting with $N^1$-[[1-(benzyloxycarbonylamino(benzyloxycarbonylimino)methyl)piperidin-3-yl]carbonyl]-$N^2$-(4-t-butylbenzoyl)-4-methoxycarbonyl-1,2-benzenediamine hydrochloride followed by precipitation with ether, the title compound was obtained as a white solid (78%): MS(FAB): 480 (MH+).

Analysis for $C_{26}H_{33}N_5O_4 \cdot HCl \cdot 2.5H_2O$: Calculated: C, 55.65; H, 6.83; N, 12.48. Found: C, 55.76; H, 6.75; N, 12.34.

EXAMPLE 37

Preparation of $N^1$-[[1-(amino(imino)methyl))piperidin-3-yl]carbonyl]-$N^2$-(4-t-butylbenzoyl)-4-carboxy-1,2-benzenediamine hydrochloride

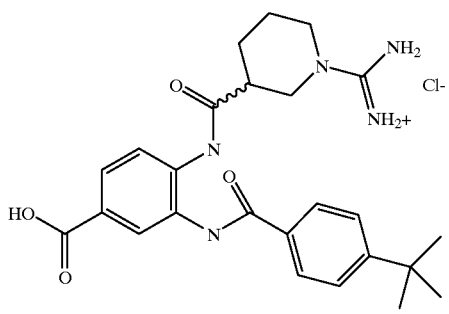

A) $N^1$-[[1-(benzyloxycarbonylamino(benzyloxycarbonylimino)methyl)piperidin-3-yl]carbonyl]-$N^2$-(4-t-butylbenzoyl)-4-carboxy-1,2-benzenediamine To a solution of $N^1$-[[1-(benzyloxycarbonylamino(benzyloxycarbonylimino)methyl)piperidin-3-yl]carbonyl]-$N^2$-(4-t-butylbenzoyl)-4-methoxycarbonyl-1,2-benzenediamine (0.7 g, 0.94 mmol), $CH_3OH$ (10 mL), dioxane (10 mL), and water (6 mL) was added 1 N NaOH (3.7 mL, 3.7 mmol). The reaction was stirred for 48 h and was concentrated. The residue was partitioned between $H_2O$ (100 mL) and $Et_2O$ (100 mL). The aqueous layer was extracted with $Et_2O$ (100 mL), acidified to pH 2.5 with 5 N HCl and extracted with EtOAc (3×200 mL). The combined EtOAc layers were washed with water, $MgSO_4$ dried, concentrated and crystallized at 0° C. overnight to give the title compound as a solid (0.63 g, 92%); TLC: $R_f$=0.38 (1:15: 135 acetic acid:methanol:chloroform); NMR ($CDCl_3$) δ1.35 (s,9H), 1.50–2.05 (m, 8H), 3.20–3.40 (m, 1N), 3.60–4.05 (m, 3H), 5.05 (s, 4H), 7.20–7.35 (m, 12H), 7.40–7.50 (m, 2H), 7.55–7.65 (m, 1H), 7.90–8.00 (m, 2H), 8.05–8.15 (m, 1H); MS(FAB): 734 (MH+).

B) $N^1$-[[1-(amino(imino)methyl))piperidin-3-yl]carbonyl]-$N^2$-(4-t-butylbenzoyl)-4-carboxy-1,2-benzenediamine hydrochloride Using a procedure similar to Example 35, except starting with $N^1$-[[1-(benzyloxycarbonylamino(benzyloxycarbonylimino)methyl)piperidin- 3-yl] carbonyl]-$N^2$-(4-t-butylbenzoyl)-4-carboxy-1,2-benzenediamine, the title compound was obtained as a white solid (79%); MS(FAB): 466 (MH+).

Analysis for $C_{25}H_{31}N_5O_4 \cdot HCl \cdot 1.5H_2O$: Calculated: C, 56.76; H, 6.67 N, 13.24. Found: C, 56.84; H, 6.29; N, 13.52.

EXAMPLE 38

Preparation of $N^1$-[3-(amino(imino)methyl)benzoyl]-$N^2$-(4-ethoxybenzoyl)-1,2-benzenediamine A) $N^1$-(3-cyanobenzoyl)-1,2-benzenediamine Using a procedure similar to 1B except starting with 1,2-phenylenediamine and triethylamine as base, the title compound was obtained as a white solid (45%); mp: 197–200° C.; NMR(300 MHz, DMSO-$d_6$): δ4.98 (s, 2H), 6.56 (t, 1H) 6.74 (d, 1H), 6.96 (t, 1H), 7.13 (d, 1H), 7.71 (t, 1H), 8.02 (d, 1H), 8.25 (d, 1H), 8.42 (s, 1H), 9.80 (s, 1H); MS(FD): 237.

Analysis for $C_{14}H_{11}N_3O$: Calculated: C, 70.87; H, 4.67; N, 17.71. Found: C, 70.68; H, 4.58; N, 17.52.

B) $N^1$-(3-cyanobenzoyl)-$N^2$-(4-ethoxybenzoyl)-1,2-benzenediamine

Using a procedure similar to 1B except starting with $N^1$-(3-cyanobenzoyl)-1,2-benzenediamine, 4-ethoxybenzoyl chloride and triethylamine as base, the title compound was obtained as a white solid (39%); mp: 168–9° C.; IR(KBr): 1645, 1672, 2231, 3377 cm$^{-1}$; MS(FD): 385 (M+).

NMR(300 MHz, DMSO-$d_6$): δ1.31 (t, 3H); 4.07 (quartet, 2H); 7.03 (d, 2H); 7.30 (m, 2H); 7.60 (m, 2H); 7.72 (t, 1H); 7.91 (d, 2H); 8.04 (d, 2H); 8.21 (d, 1H); 8.35 (s, 1H)

Analysis for $C_{23}H_{19}N_3O_3$ Calculated: C, 71.68; H, 4.97; N, 10.90. Found: C, 69.54; H, 4.71; N, 10.65.

C) $N^1$-[3-(amino(hydroxyimino)methyl)benzoyl]-$N^2$-(4-ethoxybenzoyl)-1,2-benzenediamine Using a procedure similar to 1F except starting with $N^2$-(3-cyanobenzoyl)-$N^2$-(4-ethoxybenzoyl)-1,2-benzenediamine, the title compound was obtained (100%) as a white solid; mp 180–182° C.; NMR(300 MHz, DMSO-$d_6$): δ1.31 (t, 3H); 4.07 (quartet, 2H); 7.01 (d, 2H); 7.30 (m, 2H); 7.50 (t, 1H); 7.60 (m, 2H); 7.84 (d, 1H); 7.90 (m, 3H); 8.25 (s, 1H); 9.73 (s, 1H); 9.89 (s, 1H); 10.12 (s, 1H)

Analysis for $C_{23}H_{22}N_4O_4$ Calculated: C, 66.02; H, 5.30; N, 13.39. Found: C, 65.39; H, 5.73; N, 12.63.

D) $N^1$-[3-(amino(imino)methyl)benzoyl]-$N^2$-(4-ethoxybenzoyl)-1,2-benzenediamine Using a procedure similar to 1G except starting with $N^1$-[3-(amino(hydroxyimino)methyl)benzoyl]-$N^2$-(4-ethoxybenzoyl)-1,2-benzenediamine, the title compound was obtained as a white solid (21%); mp 163–5° C.; NMR (300 MHz, DMSO-$d_6$): 1.31 (t, 3H); 4.07 (quintet, 2H); 7.01 (d, 2H); 7.20 (m, 2H); 7.60 (m, 2H); 7.65 (t, 1H); 8.00 (m, 3H); 8.29 (d, 1H); 8.54 (s, 1H); 9.33 (s, 1H); 9.54 (s, 1H); 10.14 (s, 1H); 10.72 (s, 1H); MS(FD): 402. Calculated: C, 62.94; H, 5.28; N, 12.76. Found: C, 45.54; H, 3.85; N, 8.92.

EXAMPLE 39

Preparation of $N^1$-(3-Amino-1,2-benzisoxazol-5-ylcarbonyl)-$N^2$-(4-methoxybenzoyl)-1,2-benzenediamine

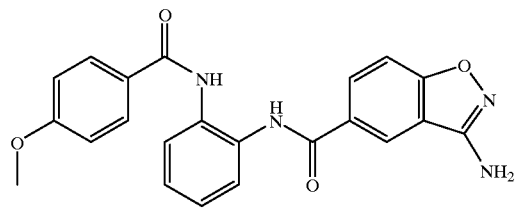

A) $N^1$-(3-Bromo-4-fluorobenzoyl)-$N^2$-(4-methoxybenzoyl)-1,2-benzenediamine

By methods substantially equivalent to those described in Example 18, except without the use of N,N-diisopropylethylamine, $N^1$-(3-bromo-4-fluorobenzoyl)-$N_2$-(4-methoxybenzoyl)-1,2-benzenediamine (2.4 g, 69%) was prepared from $N^1$-(4-methoxybenzoyl)]-1,2-benzenediamine and 3-bromo-4-fluorobenzoic acid.

$^1$H NMR

FAB-MS, m/e 443.1 (MH+)

Anal. for $C_{21}H_{16}BrFN_2O_3$ Calc: C, 56.90; H, 3.64; N, 6.32. Found: C, 56.98; H, 3.55; N, 6.40.

B) N¹-(3-Cyano-4-fluorobenzoyl)-N²-(4-methoxybenzoyl)-1,2-benzenediamine

CuCN (606 mg, 6.77 mmol) was dissolved in NMP (25 mL) and the solution was heated to 200° C. for 45 min. To this stirring solution was added N¹-(3-bromo-4-fluorobenzoyl)-N₂-(4-methoxybenzoyl)-1,2-benzenediamine (700 mg, 2.26 mmol) and stirring continued for 20 h. The solution was then cooled to room temperature, diluted with ethyl acetate and washed once with 1 N ammonium hydroxide, twice with 1 N HCl and once with brine. The organic phase was then dried with $MgSO_4$, filtered and concentrated in vacuo. The residue was chromatographed with 10% ethyl acetate/dichloromethane to give 270 mg (44%) of off-white solid.

¹H NMR

FD-MS, m/e 389.1 (M⁺)

Anal. for $C_{22}H_{16}N_3O_3 \cdot 0.9H_2O$ Calc: C, 68.35; H, 4.64; N, 10.86. Found: C, 68.63; H, 4.58; N, 10.16.

C) N¹-(3-Amino-1,2-benzisoxazol-5-ylcarbonyl)-N²-(4-methoxybenzoyl)-1,2-benzenediamine To a stirring solution of acetone oxime (94 mg, 1.28 mmol) in DMF (2 mL) was added a 1 M solution of potassium t-butoxide (1.28 mL, 1.28 mmol) in THF. After 30 min, N¹-(3-cyano-4-fluorobenzoyl)-N²-(4-methoxybenzoyl)-1,2-benzenediamine (100 mg, 0.26 mmol) was added and stirring continued for 72 h. The solvents were removed in vacuo and the residue was dissolved in methanol (20 mL). To this stirring solution was added water (15 mL) and conc HCl (3 mL), and the solution was heated to reflux. After 2 h, the solvents were removed in vacuo and the residue was dissolved in methanol. Silica gel was added and then the solvents were removed in vacuo. This dry pack was loaded onto a silica gel column and eluted with 1:1 ethyl acetate/dichloromethane. The product containing fractions were combined and concentrated to give 48 mg (46%) of white solid.

¹H NMR

FD-MS, m/e 402.1 (M⁺)

Anal. for $C_{22}H_{18}N_4O_4 \cdot 0.9H_2O$ Calc: C, 63.13; H, 4.77; N, 13.38. Found: C, 63.24; H, 4.52; N, 12.31.

Using procedures analogous to those above and standard procedures of organic chemistry, also were prepared the following compounds:

4-Acetylamino-N¹-[3-(amino(imino)methyl)benzoyl]-N²-(4-t-butylbenzoyl)-1,2-benzenediamine;

4-Acetylamino-N¹-[3-(amino(imino)methyl)benzoyl]-N²-[1-(4-pyridyl)piperidin-4-yl]methoxycarbonyl-1,2-benzenediamine.

What is claimed is:

1. A method of inhibiting factor Xa in a mammal comprising administering to a mammal in need of treatment, a factor Xa inhibiting amount of a compound of formula I

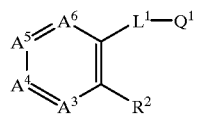

I wherein

A³, A⁴, A⁵ and A⁶, together with the two carbons to which they are attached, complete a substituted benzene in which A³ is CR³, A⁴ is CR⁴, A⁵ is CR⁵, and A⁶ is CR⁶; wherein R³ is hydrogen, hydroxy, [(1–2C)alkyl]carbonyloxy (which may bear an ω-carboxy substituent), benzoyloxy (which may bear one or more halo, hydroxy methoxy or methyl substitutents), methyl or methoxy;

one of R⁴ and R⁵ is hydrogen, methyl, halo, trifluoromethyl, nitro, amino(imino)methyl, amino (hydroxyimino)methyl, $R^fO$—, $R^fO_2C$—, $R^fO_2C$—$CH_2$—, $R^fO_2C$—$CH_2$—O—, 3-methoxycarbonyl-1-oxopropyl, $R^gNH$— or bis(methylsulfonyl)amino;

the other of R⁴ and R⁵ is hydrogen, halo or methyl; and R⁶ is hydrogen, hydroxy, [(1–2C)alkyl]carbonyloxy (which may bear an ω-carboxy substituent), benzoyloxy (which may bear one or more halo, hydroxy methoxy or methyl substitutents), methyl or methoxy;

in which $R^f$ is hydrogen, (1–4C)alkyl or benzyl; $R^g$ is hydrogen, acetyl, trifluoroacetyl, phenylalanyl, 2-(t-butoxycarbonylamino)-4-methylsulfinyl-1-oxobutyl or $R^hSO_2$—; and $R^h$ is (1–4C)alkyl, trifluoromethyl, phenyl, 3,5-dimethylisoxazol-4-yl or dimethylamino; or two adjacent residues selected from R³, R⁴, R⁵ and R⁶ together form a benz ring; and the other two are each hydrogen;

L¹ is —NH—CO—, —CO—NH— or —O—CH₂— such that —L¹—Q¹ is —NH—CO—Q¹, —CO—NH—Q¹ or —O—CH₂—Q¹ (provided that when —L¹—Q¹ is —CO—NH—Q¹, then R² is not —CO—NH—Q¹ or —CO—NH—Q²ᴮ);

Q¹ is $Q^{1A}$, $Q^{1B}$ or $Q^{1C}$ wherein $Q^{1A}$ is

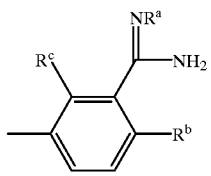

in which $R^a$ is hydrogen, $R^b$ is hydrogen and $R^c$ is hydrogen or hydroxy; or $R^a$ is hydroxy, $R^b$ is hydrogen and $R^c$ is hydrogen; or $R^a$ and $R^b$ together form a methylene or oxo group and $R^c$ is hydrogen;

$Q^{1B}$ is

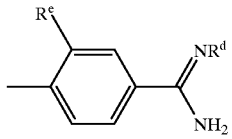

in which $R^d$ is hydrogen or hydroxy and $R^e$ is hydrogen or fluoro; and $Q^{1C}$ is

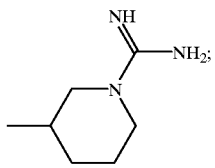

R² is a residue defined for —NH—CO—Q¹ or —CO—NH—Q¹; or

R² is —L²ᴬ—Q²ᴬ, —L²ᴮ—Q²ᴮ, —L²ᶜ—Q²ᶜ or —L²ᴰ—Q²ᴰ wherein $L^{2A}$ is a direct bond; and
$Q^{2A}$ is

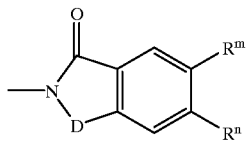

in which D is carbonyl or —CHR$^k$— in which R$^k$ is hydrogen, hydroxy, (1–6C)alkoxy or —CH$_2$—R$^j$ in which R$^j$ is carboxy, [(1–4C)alkoxy]carbonyl or carbamoyl which may bear one or two (1–2C)alkyl substituents on the nitrogen; and one of R$^m$ and R$^n$ is hydrogen and the other is amino, bromo, (1–4C)alkyl or (1–4C)alkoxy, or R$^m$ and R$^n$ together form a benz ring;

$L^{2B}$ is —NH—CO—, —CO—NH—, —O—CO—, —CH$_2$—O— or —O—CH$_2$— such that —L$^{2B}$—Q$^{2B}$ is —NH—CO—Q$^{2B}$, —CO—NH—Q$^{2B}$, —O—CO—Q$^{2B}$, —CH$_2$—O—Q$^{2B}$ or —O—CH$_2$—Q$^{2B}$; and $Q^{2B}$ is

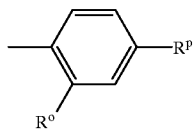

in which R$^o$ is hydrogen, halo, (1–6C)alkyl, (1–4C)alkoxy, benzyloxy or (1–4C)alkylthio; and R$^p$ is 1-hydroxyethyl, 1-hydroxy-1-methylethyl, 1-methoxy-1-methylethyl, 4-piperidinyl, 4-pyridinyl, dimethylaminosulfonyl or —J—R$^q$ in which J is a single bond, methylene, carbonyl, oxo, —S(O)q— (wherein q is 0, 1 or 2), or —NR$^r$— (wherein R$^r$ is hydrogen or methyl); and R$^q$ is (1–6C)alkyl, phenyl, 3-pyridyl or 4-pyridyl;

$L^{2C}$ is —NR$^v$—CO—X—, —NR$^v$—CS—Y—, —CH$_2$—CO—NR$^w$—CH$_2$—, —O—CO—, —O—CH$_2$—, —S—CH$_2$— or —CH$_2$—NR$^x$—CH$_2$— such that —L$^{2C}$—Q$^{2C}$ is —NR$^v$—CO—X—Q$^{2C}$, —NR$^v$—CS—Y—Q$^{2C}$, —CH$_2$—CO—NR$^w$—CH$_2$—Q$^{2C}$, —O—CO—Q$^{2C}$, —O—CH$_2$—Q$^{2C}$, —S—CH$_2$—Q$^{2C}$ or —CH$_2$—NR$^x$—CH$_2$—Q$^{2C}$ in which X is —(CH$_2$)$_x$— (wherein x is 0, 1 or 2), —NR$^w$—CH$_2$—, —O—CH$_2$— or —S—CH$_2$—; Y is —NR$^w$—CH$_2$— or —O—CH$_2$—; each of R$^v$ and R$^w$ is independently hydrogen, benzyl or (1–6C)alkyl which is not branched at the α-position; and R$^x$ is hydrogen, benzyloxycarbonyl or [(1–4C)alkoxy]carbonyl; and $Q^{2C}$ is 1-(4-pyridyl)piperidin-4-yl in which the pyridyl may bear a substituent at its 2-position selected from cyano, aminomethyl, carboxy, hydroxymethyl and (1–2C)alkyl;

$L^{2D}$ is —NH—CO— such that —L$^{2D}$—Q$^{2D}$ is —NH—CO—Q$^{2D}$; and $Q^{2D}$ is selected from 4-(4-pyridinyl)benzyloxy, 9-oxo-9H-fluoren-3-yl, benzo[b]thiophen-2-yl (which may bear a chloro, methyl or methoxy substituent), benzofuran-2-yl (which may bear a chloro, methyl or methoxy substituent), 4-(4-morpholinyl)-4-oxobutyl, and 4-piperidinyl bearing a substituent at the 1-position selected from methylsulfonyl, phenylsulfonyl and —CH$_2$—R$^z$ in which R$^z$ is isopropyl, cyclopropyl, phenyl, furyl, thienyl, 2-thiazolyl, or pyridyl in which the phenyl may bear one or two substituents independently selected from halo, cyano, hydroxy, methoxy, acetoxy, benzyloxy, amino, acetylamino, nitro and 3,4-methylenedioxy, and the thienyl or furyl may bear a methyl or nitro substiutent;

or a prodrug of the compound of formula I;

or a pharmaceutically acceptable salt of the compound of formula I or prodrug thereof.

2. The method of claim 1 wherein for an alkyl group or the alkyl portion of an alkyl containing group, (1–2C) alkyl is methyl or ethyl; (1–4C) alkyl is methyl, ethyl, propyl, isopropyl, butyl, isobutyl, or t-butyl; (1–6C) alkyl is methyl, ethyl, propyl, butyl, pentyl or hexyl; and halo is bromo or chloro.

3. The method of claim 2 wherein for an alkyl group or the alkyl portion of an alkyl containing group, (1–2C)alkyl is methyl; (1–4C)alkyl is methyl, isopropyl, butyl or t-butyl; (1–6C)alkyl is methyl, butyl or hexyl; and halo is chloro.

4. The method of claim 3 wherein R$^2$ is selected from —L$^{2A}$—Q$^{2A}$, —NH—CO—Q$^{2B}$, —NR$^v$—CO—X—Q$^{2C}$, —NR$^v$—CS—Y—Q$^{2C}$, and —NH—CO—Q$^{2D}$.

5. The method of claim 3 wherein the compound of formula I is one in which each of A$^3$, A$^5$ and A$^6$ is CH.

6. The method of claim 3 wherein R$^2$ is (4-isopropylbenzoyl)amino, (4-t-butylbenzoyl)amino, (4-methoxybenzoyl)amino, or [1-(4-pyridyl)piperidin-4-yl]methoxycarbonylamino.

7. The method of claim 3 wherein R$^4$ or R$^5$ is hydrogen, hydroxy, acetylamino, carboxymethoxy, carboxymethyl, methoxycarbonyl or carboxy.

8. A compound of formula I

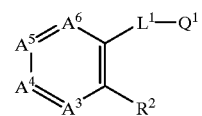

I wherein
A$^3$, A$^4$, A$^5$ and A$^6$, together with the two carbons to which they are attached, complete a substituted benzene in which A$^3$ is CR$^3$, A$^4$ is CR$^4$, A$^5$ is CR$^5$, and A$^6$ is CR$^6$;

wherein
R$^3$ is hydrogen, hydroxy, [(1–2C)alkyl]carbonyloxy (which may bear an ω-carboxy substituent), benzoyloxy (which may bear one or more halo, hydroxy methoxy or methyl substitutents), methyl or methoxy;

one of R$^4$ and R$^5$ is hydrogen, methyl, halo, trifluoromethyl, nitro, amino(imino)methyl, amino (hydroxyimino)methyl, R$^f$O—, R$^f$O$_2$C—, R$^f$O$_2$C—CH$_2$—, R$^f$O$_2$C—CH$_2$—O—, 3-methoxycarbonyl-1-oxopropyl, R$^g$NH— or bis(methylsulfonyl)amino;

the other of R$^4$ and R$^5$ is hydrogen, halo or methyl; and

R$^6$ is hydrogen, hydroxy, [(1–2C)alkyl]carbonyloxy (which may bear an ω-carboxy substituent), benzoyloxy (which may bear one or more halo, hydroxy methoxy or methyl substitutents), methyl or methoxy;

in which R$^f$ is hydrogen, (1–4C)alkyl or benzyl; R$^g$ is hydrogen, acetyl, trifluoroacetyl, phenylalanyl, 2-(t-butoxycarbonylamino)-4-methylsulfinyl-1-oxobutyl or R$^h$SO$_2$—; and R$^h$ is (1–4C)alkyl, trifluoromethyl, phenyl, 3,5-dimethylisoxazol-4-yl or dimethylamino; or two adjacent residues selected from R$^3$, R$^4$, R$^5$ and R$^6$ together form a benz ring; and the other two are each hydrogen;

L¹ is —NH—CO—, —CO—NH— or —O—CH₂— such that —L¹—Q¹ is —NH—CO—Q¹, —CO—NH—Q¹ or —O—CH₂—Q¹ (provided that when —L¹—Q¹ is —CO—NH—Q¹, then R² is not —CO—NH—Q¹ or —CO—NH—Q²ᴮ);

Q¹ is Q¹ᴬ, Q¹ᴮ or Q¹ᶜ wherein

Q¹ᴬ is

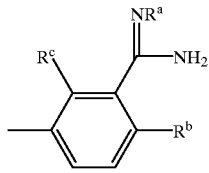

in which Rᵃ is hydrogen, Rᵇ is hydrogen and Rᶜ is hydrogen or hydroxy; or Rᵃ is hydroxy, Rᵇ is hydrogen and Rᶜ is hydrogen; or Rᵃ and Rᵇ together form a methylene or oxo group and Rᶜ is hydrogen;

Q¹ᴮ is

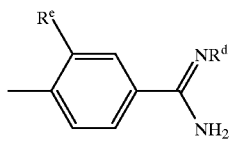

in which Rᵈ is hydrogen or hydroxy and Rᵉ is hydrogen or fluoro; and

Q¹ᶜ is

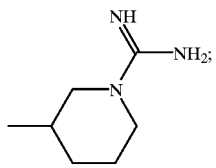

R² is a residue defined for —NH—CO—Q¹ or —CO—NH—Q¹; or

R² is —L²ᴬ—Q²ᴬ, —L²ᴮ—Q²ᴮ, —L²ᶜ—Q²ᶜ or —L²ᴰ—Q²ᴰ wherein

L²ᴬ is a direct bond; and

Q²ᴬ is

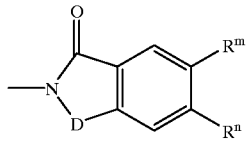

in which D is carbonyl or —CHRᵏ— in which Rᵏ is hydrogen, hydroxy, (1–6C)alkoxy or —CH₂—Rʲ in which Rʲ is carboxy, [(1–4C)alkoxy]carbonyl or carbamoyl which may bear one or two (1–2C)alkyl substituents on the nitrogen; and one of Rᵐ and Rⁿ is hydrogen and the other is amino, bromo, (1–4C)alkyl or (1–4C)alkoxy, or Rᵐ and Rⁿ together form a benz ring;

L²ᴮ is —NH—CO—, —CO—NH—, —O—CO—, —CH₂—O— or —O—CH₂— such that —L²ᴮ—Q²ᴮ is —NH—CO—Q²ᴮ, —CO—NH—Q²ᴮ, —O—CO—Q²ᴮ, —CH₂—O—Q²ᴮ or —O—CH₂—Q²ᴮ; and Q²ᴮ is

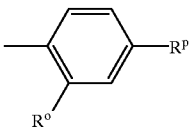

in which Rᵒ is hydrogen, halo, (1–6C)alkyl, (1–4C)alkoxy, benzyloxy or (1–4C)alkylthio; and Rᵖ is 1-hydroxyethyl, 1-hydroxy-1-methylethyl, 1-methoxy-1-methylethyl, 4-piperidinyl, 4-pyridinyl, dimethylaminosulfonyl or —J—Rᵠ in which J is a single bond, methylene, carbonyl, oxo, —S(O)q— (wherein q is 0, 1 or 2), or —NRʳ— (wherein Rʳ is hydrogen or methyl); and Rᵠ is (1–6C)alkyl, phenyl, 3-pyridyl or 4-pyridyl;

L²ᶜ is —NRᵛ—CO—X—, —NRᵛ—CS—Y—, —CH₂—CO—NRʷ—CH₂—, —O—CO—, —O—CH₂—, —S—CH₂— or —CH₂—NRˣ—CH₂— such that —L²ᶜ—Q²ᶜ is —NRᵛ—CO—X—Q²ᶜ, —NRᵛ—CS—Y—Q²ᶜ, —CH₂—CO—NRʷ—CH₂—Q²ᶜ, —O—CO—Q²ᶜ, —O—CH₂Q²ᶜ, —S—CH₂—Q²ᶜ or —CH₂—NRˣ—CH₂—Q²ᶜ in which X is —(CH₂)ₓ— (wherein x is 0, 1 or 2), —NRʷ—CH₂—, —O—CH₂— or —S—CH₂—; Y is —NRʷ—CH₂— or —O—CH₂—; each of Rᵛ and Rʷ is independently hydrogen, benzyl or (1–6C)alkyl which is not branched at the α-position; and Rˣ is hydrogen, benzyloxycarbonyl or [(1–4C)alkoxy]carbonyl; and Q²ᶜ is 1-(4-pyridyl)piperidin-4-yl in which the pyridyl may bear a substituent at its 2-position selected from cyano, aminomethyl, carboxy, hydroxymethyl and (1–2C)alkyl;

L²ᴰ is —NH—CO— such that —L²ᴰ—Q²ᴰ is —NH—CO—Q²ᴰ; and

Q²ᴰ is selected from 4-(4-pyridinyl)benzyloxy, 9-oxo-9H-fluoren-3-yl, benzo[b]thiophen-2-yl (which may bear a chloro, methyl or methoxy substituent), benzofuran-2-yl (which may bear a chloro, methyl or methoxy substituent), 4-(4-morpholinyl)-4-oxobutyl, and 4-piperidinyl bearing a substituent at the 1-position selected from methylsulfonyl, phenylsulfonyl and —CH₂—Rᶻ in which Rᶻ is isopropyl, cyclopropyl, phenyl, furyl, thienyl, 2-thiazolyl, or pyridyl in which the phenyl may bear one or two substituents independently selected from halo, cyano, hydroxy, methoxy, acetoxy, benzyloxy, amino, acetylamino, nitro and 3,4-methylenedioxy, and the thienyl or furyl may bear a methyl or nitro substiutent;

provided that the compound of formula I is not one in which

A³, A⁴, A⁵ and A⁶, together with the two carbons to which they are attached, complete a substituted benzene in which A³ is CR³, A⁴ is CR⁴, A⁵ is CR⁵, and A⁶ is CR⁶;

wherein

R³ is hydrogen;

R⁴ is hydrogen;

R⁵ is amino(imino)methyl; and

R⁶ is hydrogen;

L¹ is —NH—CO— such that —L¹—Q¹ is —NH—CO—Q¹;

Q¹ is Q¹ᴮ wherein Q¹ᴮ is

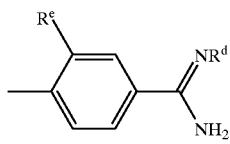

in which R$^d$ is hydrogen and R$^e$ is hydrogen; and
R² is —L²ᴮ—Q²ᴮ wherein
L²ᴮ is —O—CO— such that —L²ᴮ—Q²ᴮ is —O—CO—Q²ᴮ; and
Q²ᴮ is

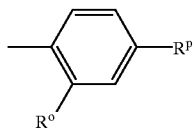

in which R$^o$ is hydrogen and R$^p$ is —J—R$^q$ in which J is a single bond, methylene, carbonyl, oxo, —S(O)q— (wherein q is 0) or NR$^r$ (wherein R$^r$ is hydrogen or methyl) and R$^q$ is (1–6C)alkyl;

or a prodrug of the compound of formula I;

or a pharmaceutically acceptable salt of the compound of formula I or prodrug thereof.

9. The compound of claim 8 wherein for an alkyl group or the alkyl portion of an alkyl containing group, (1–2C)alkyl is methyl or ethyl; (1–4C)alkyl is methyl, ethyl, propyl, isopropyl, butyl, isobutyl, or t-butyl; (1–6C)alkyl is methyl, ethyl, propyl, butyl, pentyl or hexyl; and halo is bromo or chloro.

10. The compound of claim 9 wherein for an alkyl group or the alkyl portion of an alkyl containing group, (1–2C)alkyl is methyl; (1–4C)alkyl is methyl, isopropyl, butyl or t-butyl; (1–6C)alkyl is methyl, butyl or hexyl; and halo is chloro.

11. The compound of claim 10 wherein R² is selected from —L²ᴬ—Q²ᴬ, —NH—CO—Q²ᴮ, —NR$^v$—CO—X—Q²ᶜ, —NR$^v$—CS—Y—Q²ᶜ, and —NH—CO—Q²ᴰ.

12. The compound of claim 10 wherein the compound of formula I is one in which each of A³, A⁵ and A⁶ is CH.

13. The compound of claim 12 wherein R² is (4-isopropylbenzoyl)amino, (4-t-butylbenzoyl)amino, (4-methoxybenzoyl)amino, or [1-(4-pyridyl)piperidin-4-yl]methoxycarbonylamino.

14. The compound of claim 12 wherein R⁴ or R⁵ is hydrogen, hydroxy, acetylamino, carboxymethoxy, carboxymethyl, methoxycarbonyl or carboxy.

15. A prodrug of claim 10 which is a carbamate in which an amino (or imino) group of Q¹ is substituted by a [(1–4C)alkoxy]-carbonyl or acetoxymethoxycarbonyl group.

16. A pharmaceutical composition comprising a compound of formula I, or prodrug or pharmaceutically acceptable salt thereof, as claimed in claim 10 in association with a pharmaceutically acceptable carrier, excipient or diluent.

17. A process for preparing a compound of formula I (or a pharmaceutically acceptable salt thereof) as provided in claim 10 which comprises (A) for a compound of formula I in which the linkage of R² to the ring terminates in —NH—CO—, —NR$^v$—CO— or —NR$^v$—CS—, acylating an amine of formula II,

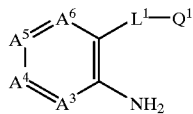

or a corresponding amine in which the nitrogen bears the group R$^v$, using a corresponding acid which terminates with the group HO—CO— or HO—CS—, or an activated derivative thereof;

(B) for a compound of formula I in which —L¹—Q¹ is —NH—CO—Q¹, acylating an amine of formula III

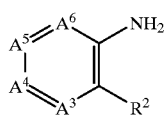

using an acid of formula HO—CO—Q¹, or an activated derivative thereof;

(C) for a compound of formula I in which —L¹—Q¹ is —CO—NH—Q¹ and R² is of the form —NH—CO—Q², acylating an amine of formula H₂N—Q¹ using a [1,3]oxazine of formula IV,

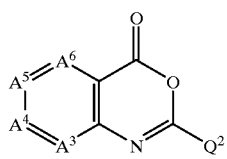

wherein Q² represents Q²ᴮ, Q²ᶜ or Q²ᴰ;

(D) for a compound of formula I in which R² is —L²ᴬ—Q²ᴬ and D is carbonyl, diacylating a compound of formula II using an anhydride of formula V;

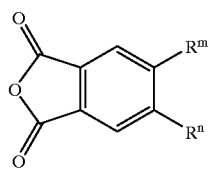

(E) for a compound of formula I in which Q¹ is Q¹ᴬ and R$^a$ is hydroxy or in which Q¹ is Q¹ᴮ and R$^d$ is hydroxy, adding hydroxylamine to a corresponding nitrile to afford the compound with an amino(hydroxyimino)methyl group;

(F) for a compound of formula I in which Q¹ is Q¹ᴬ and R$^a$, R$^b$ and R$^c$ are each hydrogen, or in which Q¹ is Q¹ᴮ and R$^d$ is hydrogen, hydrogenolyzing the N—O bond of a corresponding compound of formula I in which R$^a$ is hydroxy or in which R$^d$ is hydroxy;

(G) for a compound of formula I in which Q¹ is Q¹ᴬ and R$^a$, R$^b$ and R$^c$ are each hydrogen, or in which Q¹ is Q¹ᴮ and R$^d$ is hydrogen, substituting the methylthio group of a corresponding compound bearing a —C(SCH₃)=NH group with an amino group by treatment with ammonia, or a solvate or salt thereof;

(H) for a compound of formula I in which Q¹ is Q¹ᴬ and R$^a$ and R$^b$ together form a methylene or oxo group, cyclizing a corresponding 4-aminomethyl-3-cyanophenyl or 4-aminooxo-3-cyanophenyl compound; or (I) for a compound of formula I in which $Q^1$ is $Q^{1A}$ and $R^c$ is hydroxy, hydrogenolyzing the N—O bond of a corresponding 3-amino-1,2-benzisoxazol-7-yl compound;

whereafter, for any of the above procedures, when a functional group is protected using a protecting group, removing the protecting group; and whereafter, for any of the above procedures, when a pharmaceutically acceptable salt of a compound of formula I is required, it is obtained by reacting the basic form of a basic compound of formula I with an acid affording a physiologically acceptable counterion or the acidic form of an acidic compound of formula I with a base affording a physiologically acceptable counterion or by any other conventional procedure; and wherein, unless otherwise specified, $L^1$, $Q^1$, $R^2$, $A^3$, $A^4$, $A^5$ and $A^6$ have any of the values defined in claim 10.

18. The method of claim 4 wherein the compound of formula I is one in which each of $A^3$, $A^5$ and $A^6$ is CH.

19. The method of claim 5 wherein $R^2$ is (4-isopropylbenzoyl)amino, (4-t-butylbenzoyl)amino, (4-methoxybenzoyl)amino, or [1-(4-pyridyl)piperidin-4-yl]methoxycarbonylamino.

20. The method of claim 4 wherein $R^4$ or $R^5$ is hydrogen, hydroxy, acetylamino, carboxymethoxy, carboxymethyl, methoxycarbonyl or carboxy.

21. The method of claim 5 wherein $R^4$ is hydrogen, hydroxy, acetylamino, carboxymethoxy, carboxymethyl, methoxycarbonyl or carboxy.

22. The method of claim 6 wherein $R^4$ or $R^5$ is hydrogen, hydroxy, acetylamino, carboxymethoxy, carboxymethyl, methoxycarbonyl or carboxy.

23. The compound of claim 11 wherein the compound of formula I is one in which each of $A^3$, $A^5$ and $A^6$ is CH.

24. The compound of claim 12 wherein $R^2$ is (4-isopropylbenzoyl)amino, (4-t-butylbenzoyl)amino, (4-methoxybenzoyl)amino, or [1-(4-pyridyl)piperidin-4-yl]methoxycarbonylamino.

25. The compound of claim 11 wherein $R^4$ or $R^5$ is hydrogen, hydroxy, acetylamino, carboxymethoxy, carboxymethyl, methoxycarbonyl or carboxy.

26. The compound of claim 12 wherein $R^4$ is hydrogen, hydroxy, acetylamino, carboxymethoxy, carboxymethyl, methoxycarbonyl or carboxy.

27. The compound of claim 13 wherein $R^4$ or $R^5$ is hydrogen, hydroxy, acetylamino, carboxymethoxy, carboxymethyl, methoxycarbonyl or carboxy.

28. The method of any of claims 1–7 or 18–22 wherein $L^1$—$Q^1$ is —NH—CO—$Q^1$.

29. The method of any of claims 1–7 or 18–22 wherein $L^1$—$Q^1$ is —CO—NH—$Q^1$.

30. The compound of any of claim 8–14 or 23–27 wherein $L^1$—$Q^1$ is —NH—CO—$Q^1$.

31. The compound of any of claims 8–14 or 23–27 wherein $L^1$—$Q^1$ is —CO—NH—$Q^1$.

* * * * *